US008057408B2

(12) United States Patent
Cain et al.

(10) Patent No.: US 8,057,408 B2
(45) Date of Patent: Nov. 15, 2011

(54) PULSED CAVITATIONAL ULTRASOUND THERAPY

(75) Inventors: Charles A. Cain, Ann Arbor, MI (US); Zhen Xu, Ann Arbor, MI (US); J. Brian Fowlkes, Ann Arbor, MI (US); Timothy L. Hall, Ann Arbor, MI (US); William W. Roberts, Saline, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 473 days.

(21) Appl. No.: 12/121,001

(22) Filed: May 15, 2008

(65) Prior Publication Data

US 2008/0319356 A1 Dec. 25, 2008

Related U.S. Application Data

(63) Continuation-in-part of application No. 11/523,201, filed on Sep. 19, 2006, now abandoned.

(60) Provisional application No. 60/786,322, filed on Mar. 27, 2006, provisional application No. 60/719,703, filed on Sep. 22, 2005, provisional application No. 60/753,376, filed on Dec. 22, 2005, provisional application No. 60/938,806, filed on May 18, 2007.

(51) Int. Cl.
*A61H 1/00* (2006.01)

(52) U.S. Cl. .......................................................... 601/2

(58) Field of Classification Search .................. 600/439; 601/2
See application file for complete search history.

(56) References Cited

U.S. PATENT DOCUMENTS

| 4,117,446 A | 9/1978 | Alais |
| 4,269,174 A | 5/1981 | Adair |
| 4,351,038 A | 9/1982 | Alais |
| 4,483,345 A | 11/1984 | Miwa |
| 4,549,533 A | 10/1985 | Cain et al. |
| 4,550,606 A | 11/1985 | Drost |
| 4,622,972 A | 11/1986 | Giebeler, Jr. |
| 4,689,986 A | 9/1987 | Carson et al. |

(Continued)

FOREIGN PATENT DOCUMENTS

EP 0017382 A1 10/1980

(Continued)

OTHER PUBLICATIONS

Z. Xu, A. Ludomirsky, L. Y. Eun, T. L. Hall, B.C. Tran, J.B. Fowlkes, and C.A. Cain, "Controlled ultrasound tissue erosion," *IEEE Trans Ultrasonics Ferroelectrics Freq Control*, vol. 51, pp. 726-736, 2004.

(Continued)

*Primary Examiner* — Tse Chen
*Assistant Examiner* — Hien Nguyen
(74) *Attorney, Agent, or Firm* — ShayGlenn LLP

(57) ABSTRACT

Therapy methods using pulsed cavitational ultrasound therapy can include the subprocesses of initiation, maintenance, therapy, and feedback of the histotripsy process, which involves the creation and maintenance of ensembles of microbubbles and the use of feedback in order to optimize the process based on observed spatial-temporal bubble cloud dynamics. The methods provide for the subdivision or erosion of tissue, liquification of tissue, and/or the enhanced delivery of therapeutic agents. Various feedback mechanisms allow variation of ultrasound parameters and provide control over the pulsed cavitational process, permitting the process to be tuned for a number of applications. Such applications can include specific tissue erosion, bulk tissue homogenization, and delivery of therapeutic agents across barriers.

19 Claims, 26 Drawing Sheets

U.S. PATENT DOCUMENTS

| | | |
|---|---|---|
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,888,746 A | 12/1989 | Wurster et al. |
| 4,890,267 A | 12/1989 | Rudolph |
| 4,922,917 A | 5/1990 | Dory |
| 4,938,217 A | 7/1990 | Lele |
| 4,991,151 A | 2/1991 | Dory |
| 4,995,012 A | 2/1991 | Dory |
| RE33,590 E | 5/1991 | Dory |
| 5,065,751 A | 11/1991 | Wolf |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,209,221 A | 5/1993 | Riedlinger |
| 5,215,680 A | 6/1993 | D'Arrigo |
| 5,219,401 A | 6/1993 | Cathignol et al. |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,409,002 A | 4/1995 | Pell |
| 5,431,621 A | 7/1995 | Dory |
| 5,435,311 A | 7/1995 | Umemura et al. |
| 5,469,852 A | 11/1995 | Nakamura et al. |
| 5,474,071 A | 12/1995 | Chapelon et al. |
| 5,474,531 A | 12/1995 | Carter |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A * | 12/1996 | Zhong et al. ............. 601/4 |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,676,692 A | 10/1997 | Sanghvi et al. |
| 5,678,554 A | 10/1997 | Hossack et al. |
| 5,694,936 A | 12/1997 | Fujimoto et al. |
| 5,695,460 A | 12/1997 | Siegel et al. |
| 5,717,657 A * | 2/1998 | Ruffa ............. 367/131 |
| 5,724,972 A | 3/1998 | Petrofsky |
| 5,743,863 A | 4/1998 | Chapelon |
| 5,759,162 A | 6/1998 | Oppelt et al. |
| 5,769,790 A | 6/1998 | Watkins et al. |
| 5,797,848 A | 8/1998 | Marian et al. |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,932,807 A | 8/1999 | Mallart |
| 5,947,904 A | 9/1999 | Hossack et al. |
| 6,001,069 A | 12/1999 | Tachibana et al. |
| 6,022,309 A | 2/2000 | Celliers et al. |
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,128,958 A | 10/2000 | Cain |
| 6,143,018 A | 11/2000 | Beuthan et al. |
| 6,176,842 B1 | 1/2001 | Tachibana et al. |
| 6,309,355 B1 * | 10/2001 | Cain et al. ............. 600/439 |
| 6,321,109 B2 | 11/2001 | Ben-Haim et al. |
| 6,344,489 B1 * | 2/2002 | Spears ............. 516/10 |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,543,272 B1 | 4/2003 | Vitek |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,770,031 B2 | 8/2004 | Hynynen et al. |
| 6,790,180 B2 | 9/2004 | Vitek |
| 6,852,082 B2 | 2/2005 | Strickberger et al. |
| 6,869,439 B2 | 3/2005 | White et al. |
| 6,890,332 B2 | 5/2005 | Truckai et al. |
| 6,929,609 B2 | 8/2005 | Asafusa |
| 7,004,282 B2 | 2/2006 | Manna et al. |
| 7,128,711 B2 | 10/2006 | Medan et al. |
| 7,175,596 B2 | 2/2007 | Vitek et al. |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,442,168 B2 | 10/2008 | Novak et al. |
| 2001/0039420 A1 * | 11/2001 | Burbank et al. ............. 606/45 |
| 2002/0045890 A1 | 4/2002 | Celliers et al. |
| 2002/0099356 A1 * | 7/2002 | Unger et al. ............. 604/501 |
| 2003/0092982 A1 * | 5/2003 | Eppstein ............. 600/411 |
| 2003/0157025 A1 | 8/2003 | Unger et al. |
| 2004/0127815 A1 * | 7/2004 | Marchitto et al. ............. 600/573 |
| 2004/0138563 A1 | 7/2004 | Moehring et al. |
| 2004/0236248 A1 * | 11/2004 | Svedman ............. 600/573 |
| 2004/0243021 A1 * | 12/2004 | Murphy et al. ............. 600/549 |
| 2005/0038339 A1 | 2/2005 | Chauhan et al. |
| 2006/0060991 A1 | 3/2006 | Holsteyns et al. |
| 2007/0010805 A1 | 1/2007 | Fedewa et al. |
| 2007/0016039 A1 | 1/2007 | Vortman et al. |
| 2007/0065420 A1 | 3/2007 | Johnson |
| 2007/0083120 A1 | 4/2007 | Cain et al. |
| 2007/0161902 A1 | 7/2007 | Dan |

| | | | |
|---|---|---|---|
| 2009/0177085 | A1 | 7/2009 | Maxwell et al. |
| 2010/0069797 | A1 | 3/2010 | Cain et al. |
| 2011/0040190 | A1 | 2/2011 | Jahnke et al. |

FOREIGN PATENT DOCUMENTS

| | | |
|---|---|---|
| EP | 0320303 A2 | 6/1989 |
| EP | 0332871 A2 | 9/1989 |
| EP | 0384831 A2 | 8/1990 |
| GB | 2099582 A | 12/1982 |
| WO | WO94/06355 A1 | 3/1994 |

OTHER PUBLICATIONS

Z. Xu, J. B. Fowlkes, E. D. Rothman, A. M. Levin, and C.A. Cain, "Controlled Ultrasound Tissue Erosion: the role of dynamic interaction between insonation and microbubble activity," *Journal of the Acoustical Society of America,* vol. 117, pp. 424-435, 2005.

Z. Xu, J. B. Fowlkes, A. Ludomirsky, and C. A. Cain, "Investigation of intensity threshold for ultrasound tissue erosion," *Ultrasound in Med. & Biol.,* vol. 31, pp. 1673-1682, 2005.

J. E. Parsons, C. A. Cain, G.D. Abrams, and J. B. Fowlkes, "Pulsed cavitational ultrasound therapy for controlled tissue homogenization," *Ultrasound in Med. & Biol.,* vol. 32, pp. 115-129, 2006.

W. W. Roberts, T. J. Hall, K. Ives, J.S. Wolf Jr., J. B. Fowlkes, and C. A. Cain, "Pulsed cavitational ultrasound: a noninvasive technology for controlled tissue ablation (histotripsy) in the rabbit kidney," *Journal of Urology,* vol. 175, pp. 734-738, 2006.

Z. Xu, J. B. Fowlkes, and C. A. Cain, "A new strategy to enhance cavitational tissue erosion by using a high intensity initiating sequence," *IEEE Trans Ultrasonics Ferroelectrics Freq Control,* vol. 53, pp. 1412-1424, 2006.

Z. Xu, J. B. Fowlkes, and C. A. Cain, "Optical and acoustic monitoring of bubble cloud dynamics at a tissue-fluid interface in ultrasound tissue erosion", *Journal of the Acoustical Society of America,* vol. 121, pp. 2421-2430, 2007.

Z. Xu, T.L. Hall, J. B. Fowlkes, and C. A. Cain, "Effects of acoustic parameters on bubble cloud dynamics in ultrasound tissue erosion (histotripsy)", *Journal of the Acoustical Society of America,* vol. 122, pp. 229-236, 2007.

International Search Report and Written Opinion filed in PCT/US2009/031857 dated Aug. 28, 2009.

Cain, Charles A.; Histrotripsy: controlled mechanical sub-division of soft tissues by high intensity pulsed ultrasound (conference presentation); International Symposium on Therapeutic Ultrasound; pp. T005; 2005.

Hall et al.; Ultrasound imaging feedback of tissue liquefaction in ultrasound surgery; Ultrasonics Symposium; IEEE; vol. 3; pp. 1732-1734; Sep. 18-21, 2005.

Xu et al.; High Speed Imaging of Bubble Clouds Generated in Pulsed Ultrasound Cavitational Therapy'Histotripsy; IEEE Trans Ultrason Ferroelectr Freq Control; ; vol. 54; No. 10; pp. 2091R2101; Oct. 2007.

Hall et al.; U.S. Appl. No. 12/868,768 entitled "Micromanipulator Control Arm for Therapeutic and Imaging Ultrasound Transducers," filed Aug. 26, 2010.

Cain et al.; U.S. Appl. No. 12/868,775 entitled "Devices and Methods for Using Controlled Bubble Cloud Cavitation in Fractionating Urinary Stones," filed Aug. 26, 2010.

Cain et al.; U.S. Appl. No. 12/887,705 entitled "Gel phantoms for testing cavitational ultrasound (histotripsy) transducers," filed Sep. 22, 2010.

* cited by examiner

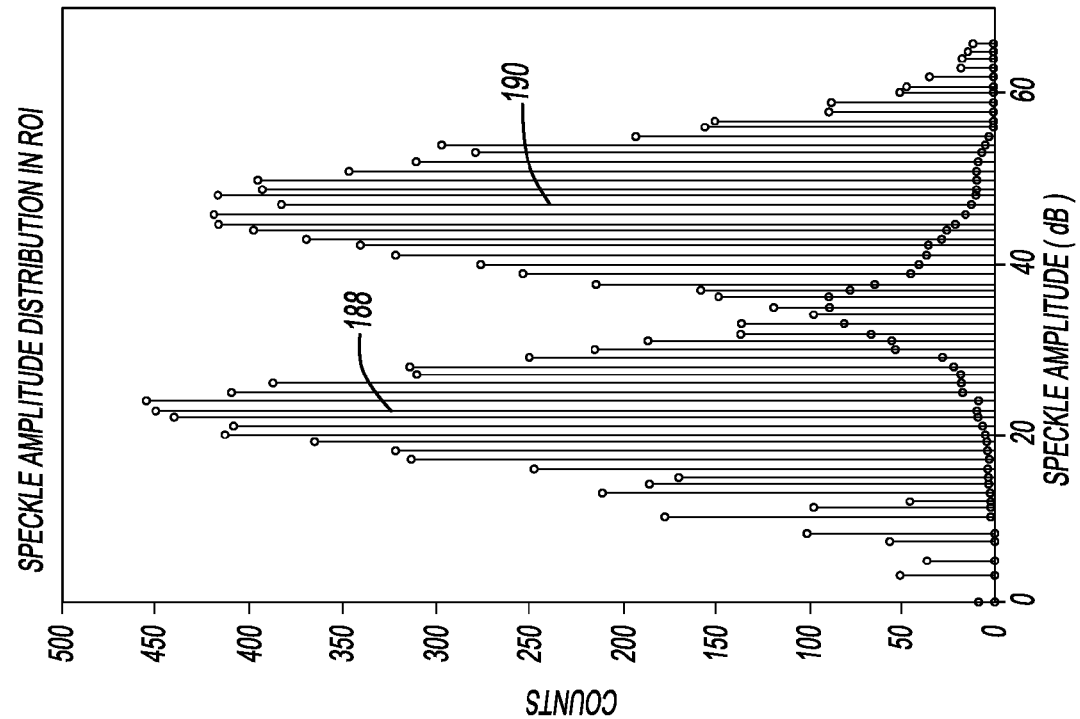
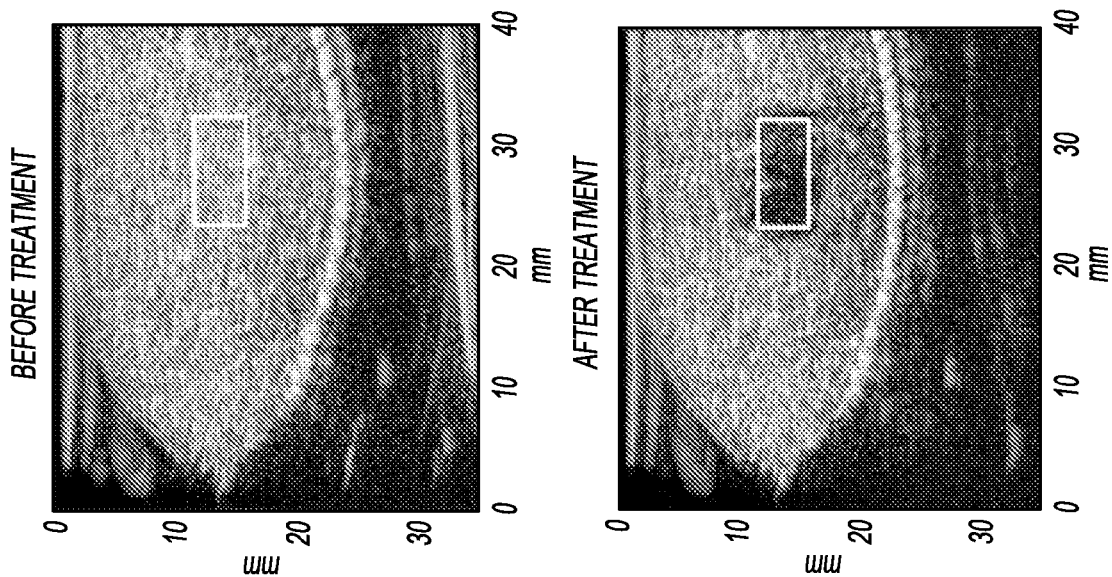
Fig-24

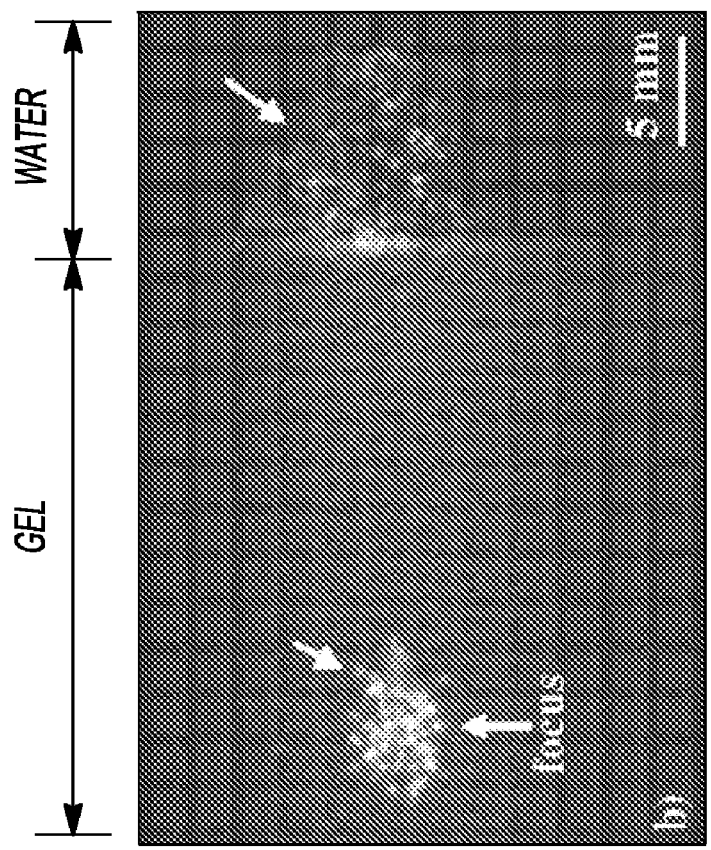
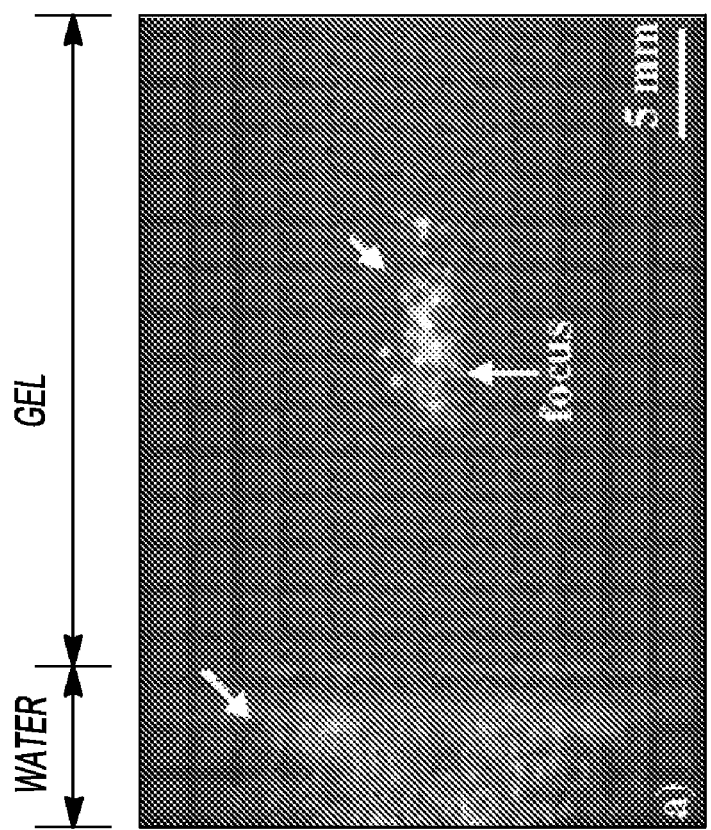
Fig-38

PULSED CAVITATIONAL ULTRASOUND THERAPY

CROSS-REFERENCE TO RELATED APPLICATIONS

This application is a continuation-in-part of U.S. patent application Ser. No. 11/523,201 filed on Sep. 19, 2006, which claims the benefit of U.S. Provisional Patent Application No. 60/786,322, filed Mar. 27, 2006, U.S. Provisional Patent Application No. 60/719,703, filed Sep. 22, 2005, and U.S. Provisional Patent Application No. 60/753,376, filed Dec. 22, 2005. The present application further claims the benefit of U.S. Provisional Patent Application No. 60/938,806, filed May 18, 2007. The disclosures of the above applications are incorporated herein by reference.

GOVERNMENT RIGHTS

This invention was made with government support under RR014450, HL077629, and DK042290, awarded by the National Institutes of Health. The government has certain rights in the invention.

INTRODUCTION

The present teachings relate to ultrasound therapy and, more particularly, relate to methods and apparatus for the controlled use of cavitation during ultrasound procedures.

Treatment relating to tissue defects, various medical conditions, and delivery of therapeutic agents often involves invasive therapies. Such invasive therapies include general surgical techniques, endoscopic techniques, and perfusions and aspirations, each of which can involve one or more incisions or punctures. Several negative effects can be associated with invasive therapies, including the risk of infection, internal adhesion formation and cosmetic issues related to skin surface scarring, and the need for pain management during and after the procedure. In fact, invasive surgical therapies can require post-operative treatment, including additional invasive procedures, to manage the effects of the original surgical intervention, in addition to any follow-up treatment the invasive therapy was intended to address.

Invasive therapies are often used for tissue removal or ablation, such as in the resection of tumors, for bulk tissue fractionization, and for delivery of therapeutic agents including drugs, for example via a cannula.

Tissue ablation is often used in treatment of tumors. For example, an estimated 36,160 renal tumors will be diagnosed in 2005, the majority of which will be found incidentally. Incidental detection accounted for approximately 10% of renal tumors found prior to 1970, 60% in 1990, and presumably an even greater percentage today. This trend, largely a result of widespread use of cross-sectional imaging, has resulted in the diagnosis of increasing numbers of small size, earlier stage renal masses. However, the optimal treatment for small renal masses has yet to be definitively established and continues to evolve. Radical nephrectomy, the traditional method of treatment, has largely been supplanted by laparoscopic and open surgical nephron-sparing techniques. However, these methods are all invasive therapies.

Efforts to further reduce morbidity have resulted in the incorporation of percutaneous ablative techniques (radiofrequency ablation and cryotherapy) into the clinical armamentarium. These minimally invasive methods deliver energy via percutaneous probes to induce thermal effects that cause cellular injury and death in the targeted region. However, inhomogeneous tissue heating/cooling, variable blood perfusion resulting in heat sink effects, and changing tissue characteristics during treatment, are factors that are difficult to predict or control and ultimately may limit these thermal ablative modalities. Development of noninvasive thermal ablative technology (High Intensity Focused Ultrasound—HIFU) has progressed. Unfortunately, this technology may also be limited by the inability to precisely control the margin of thermal injury as well as the lengthy time required to closely pack hundreds of lesions necessary to ablate a clinically useful volume of tissue.

Furthermore, therapies that deliver therapeutic agents, including pharmaceutical compositions and various drugs, to a site in need to treatment can still be frustrated due to natural barriers in spite of local delivery. Single injections and/or continuous administration via a cannula pump can deliver a therapeutic agent to a localized site, however, one or more barriers may still prevent optimal efficacy. For example, barriers such as the blood-brain-barrier, cell membranes, endothelial barriers, and skin barriers that compartmentalize one tissue or organ volume from another can prevent or reduce the action of a therapeutic agent.

Ultrasound has been used to enhance drug uptake or delivery, although the mechanisms of observed effects, which are often modest at best, are poorly understood. Many experiments or devices use acoustic parameters that are arrived at by trial and error approaches with no rational basis for optimization.

Older ultrasound drug delivery approaches almost always try to avoid cavitation except when it can be carefully controlled and localized, e.g., at the end of small vibrating needles and probes. The primary reason for avoiding cavitation is that it is very unpredictable due to significant variations in cavitation thresholds which are usually depend on the quantity and quality of small gas bubbles and other cavitation nuclei in different tissues. This makes it impossible to obtain reliable results with predictable dose-effect relationships, and make it very difficult to predict the degree of enhanced transport of deliverable substances. Moreover, prior art methods of assisted drug delivery do not allow easy assessment or feedback of when the process is operating effectively, and often do not provide any feedback which can be used to optimize the process.

To overcome the negative effects associated with invasive therapy methods, noninvasive ultrasound surgery has been used as an alternative. However, use of ultrasound based therapies has been problematic due the phenomenon of acoustic cavitation. Acoustic cavitation is a term used to define the interaction of an acoustic field, such as an ultrasound field, with bodies containing gas and/or vapor. This term is used in reference to the production of small gas bubbles, or microbubbles, in the liquid. Specifically, when an acoustic field is propagated into a fluid, the stress induced by the negative pressure produced can cause the liquid to rupture, forming a void in the fluid which will contain vapor and/or gas. Acoustic cavitation also refers to the oscillation and/or collapse of microbubbles in response to the applied stress of the acoustic field.

Methods have been developed to initiate and maintain cavitation for use in therapy. For example, Cain et al. (U.S. Pat. No. 6,309,355), which is hereby incorporated by reference, describes apparatus and methods that use cavitation induced by an ultrasound beam to create a controlled surgical lesion in a selected therapy volume of a patient.

However, previous invasive methods of tissue removal or ablation, bulk tissue fractionization, and delivery of therapeutic agents, and even noninvasive methods, do not allow easy assessment or feedback of when the process is operating effectively, and often do not provide any feedback which can be used to optimize the process. Consequently, more effective methods and techniques for pulsed cavitational ultrasound therapies are desirable and would enable beneficial noninvasive alternatives to many present methods in the surgical field. In particular, monitoring and receiving feedback of pulsed cavitational ultrasound therapies during the procedure would inform a clinician whether the treatment procedure is progressing adequately according to plan and when it can be ended. As such, the ability to monitor and adjust the ultrasound therapy concomitant with treatment would provide significant advantages over prior ultrasound therapies.

SUMMARY

The present disclosure provides methods for controlled mechanical subdivision of soft tissue that can include actuating a transducer to output an initiation pulse sequence. Formation of a bubble cloud is detected in the soft tissue, and the presence of the bubble cloud nuclei contributes to fractionation of the soft tissue and predisposes the tissue for further fractionation. A transducer is actuated to output a bubble cloud sustaining sequence and the cessation of the bubble cloud is detected.

Various embodiments further comprise reactuating the transducer to output the bubble cloud sustaining sequence prior to the cessation of the bubble cloud.

In some embodiments, detecting formation of a bubble cloud in the soft tissue comprises employing an ultrasound imaging device to detect and monitor the bubble cloud. The ultrasound imaging device can also be used to detect and monitor the bubble cloud while simultaneously actuating the transducer.

Other various embodiments can include methods using optical feedback, acoustic feedback, or resultant backscatter signal to detect cessation of the bubble cloud. In further embodiments, a transducer imager detecting reflection of at least one initiation pulse sequence and the bubble cloud sustaining sequence is used to detect cessation of the bubble cloud.

Various embodiments can also include methods where detecting cessation of the bubble cloud comprises detecting an optical attenuation of the bubble cloud.

In other various embodiments, methods can include actuating the transducer to output a bubble cloud sustaining sequence without thermally degrading the soft tissue.

Methods of the present disclosure can include embodiments where detecting formation of a bubble cloud in the soft tissue is completed simultaneously with the actuating of the transducer to out put an initiation pulse sequence.

Other various embodiments can include methods where detecting cessation of the bubble cloud is completed simultaneously with the actuating of the transducer to output a bubble cloud sustaining sequence.

In some embodiments, the bubble cloud partially fractionates the soft tissue by fractionating only portions of a cell.

Various embodiments can further include methods where detecting cessation of the bubble cloud comprises detecting cessation of the bubble cloud and outputting a signal representative of attenuation of the bubble cloud, the methods further including receiving and monitoring the signal and adjusting the bubble cloud sustaining sequence in response to the signal.

In some embodiments, the initiation pulse sequence, sustaining sequence, and therapy pulse sequence comprise a single output from the transducer.

According to the principles of the present teachings, a non-invasive, non-thermal technology that utilizes pulsed, focused ultrasound energy to induce mechanical cavitation of tissue is provided. This process enables precise, non-thermal, subdivision (i.e., mechanical disruption) of tissue within a target volume.

The present teachings further provide new ultrasound methods and related devices and systems, to provide for ultrasound enhanced drug delivery. Delivery here relates to enhanced uptake or transport of a drug, molecule, nano-particle, or substance across drug-resistant barriers in cells, organs, or the body in general. Mechanical disruption in the context of drug delivery means momentarily (or otherwise) breaking down membrane, skin, endothelial, cardiovascular, blood-brain barrier and other barriers to transport of useful substances from one compartment into another within the body.

The present technology affords multiple benefits over those methods known in the art. These benefits can include: cavitation is easily seen in ultrasound images allowing localization of the beams with respect to ultrasonic images of the target volume; cavitation is a nonlinear process sensitive to many acoustic parameters allowing numerous opportunities to optimize acoustic inputs for different therapy results; cavitation produces results non-thermally by mechanically subdividing tissue so that the process can progress at time average intensities much below those which produce any appreciable heating of either the therapy volume, or more importantly, the intervening tissues; mechanically disrupted tissue results in changes which can be readily seen in ultrasound images allowing for robust ways of verifying the therapeutic outcome desired, perhaps in real time (with feedback) during the exposures; and finally, no complex, expensive, (often clinically impractical) noninvasive temperature measurement schemes are ever needed.

The pulsed cavitational ultrasound therapy (i.e., the histotripsy process) coupled with the ability to monitor and adjust the process based on feedback provides a significant advantage over previous methods. The present disclosure provides methods to optimize this process based on observed spatial-temporal bubble cloud dynamics, and allows the process to be optimized in real time during tissue erosion or the delivery or enhanced transport of therapeutic agents.

Further areas of applicability and advantages will become apparent from the following description. It should be understood that the description and specific examples, while exemplifying embodiments of the technology, are intended for purposes of illustration only and are not intended to limit the scope of the present technology.

DRAWINGS

The drawing described herein are for illustration purposes only and are not intended to limit the scope of the present teachings in any way.

FIG. 1 is a schematic illustration of an exemplary apparatus for performing pulsed cavitational ultrasound therapy constructed in accordance with the teachings of the present disclosure;

FIG. 2 graphically illustrates the steps of initiation detection in sequence;

FIG. 3 graphically illustrates the steps of initiation and extinction detection in sequence;

FIG. 4 illustrates waveforms of acoustic backscatter corresponding to the data in FIG. 3, FIG. 5 graphically illustrates different acoustic backscatter signals and corresponding tissue effects generated by the same ultrasound exposure in three treatments;

FIG. 6 graphically illustrates the waveforms of therapeutic ultrasound pulses as recorded by a membrane hydrophone;

FIG. 7 graphically illustrates the initiation delay time as a function of spatial-peak pulse-average intensity ($I_{SPPA}$);

FIG. 8 graphically illustrates the initiation delay time vs. intensity and gas concentration;

FIG. 9 is a schematic illustration of another exemplary apparatus for performing pulsed cavitational ultrasound therapy constructed in accordance with the teachings of the present disclosure;

FIG. 10 graphically illustrates the voltage trace of the photodiode response to a laser pulse;

FIG. 11 graphically illustrates an example of light attenuation caused by formation of the bubble cloud as the photodiode voltage output;

FIG. 12 graphically illustrates the process of detecting initiation of the variable backscatter using different initiation threshold coefficients and different moving window sizes;

FIG. 13 graphically illustrates the number of treatments when erosion was observed but no initiation was detected is plotted as functions of the initiation threshold coefficient m and the moving window size k;

FIG. 14 graphically illustrates the number of treatments when no erosion was observed but initiation was detected is plotted as functions of m and k;

FIG. 15 graphically illustrates the initiation delay time plotted as functions of k and m using the backscatter data set from FIG. 13;

Figure 19:
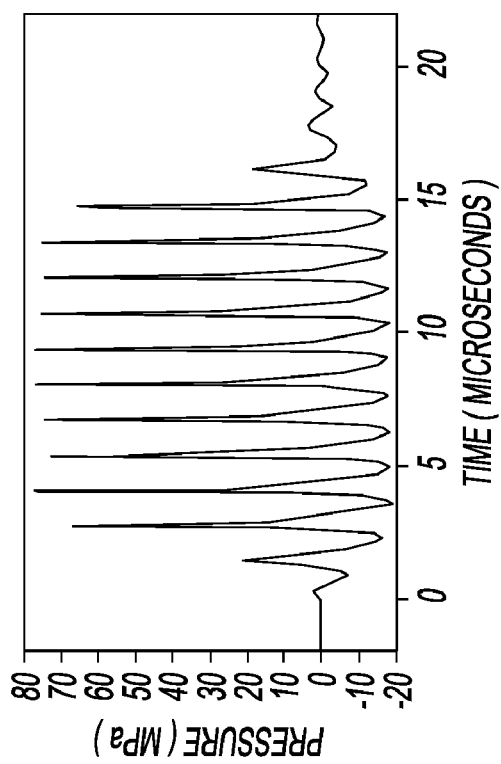
Figure 20:
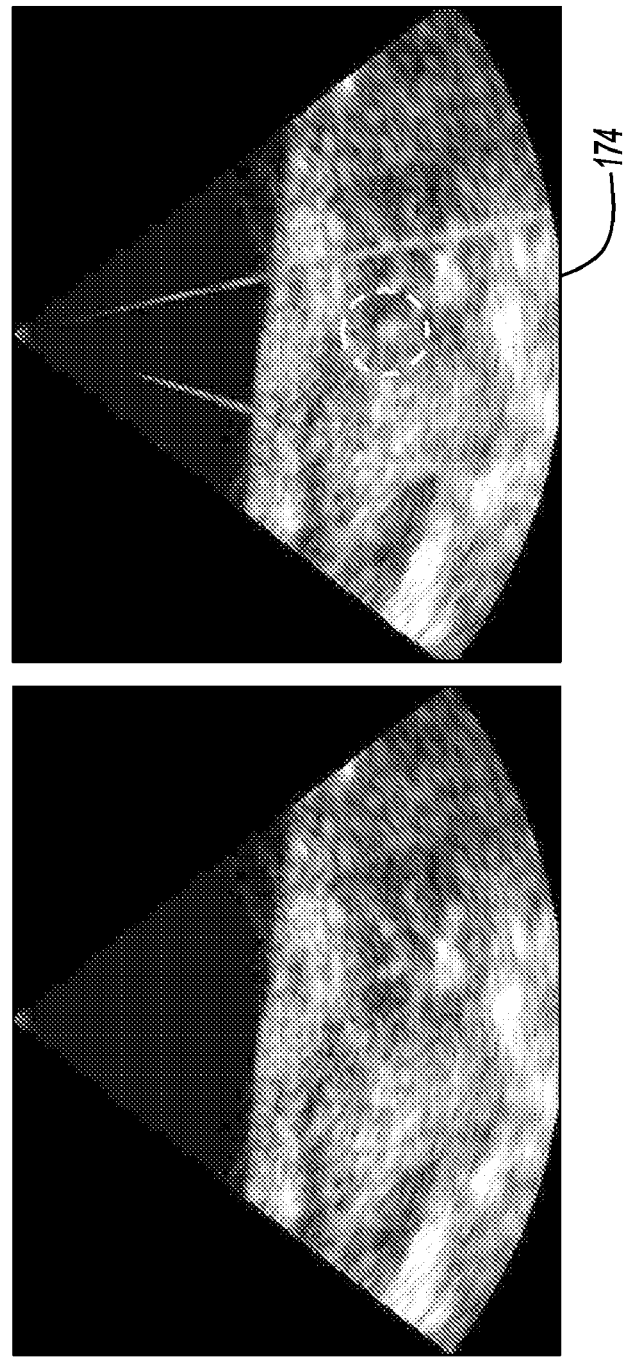
Figure 21:
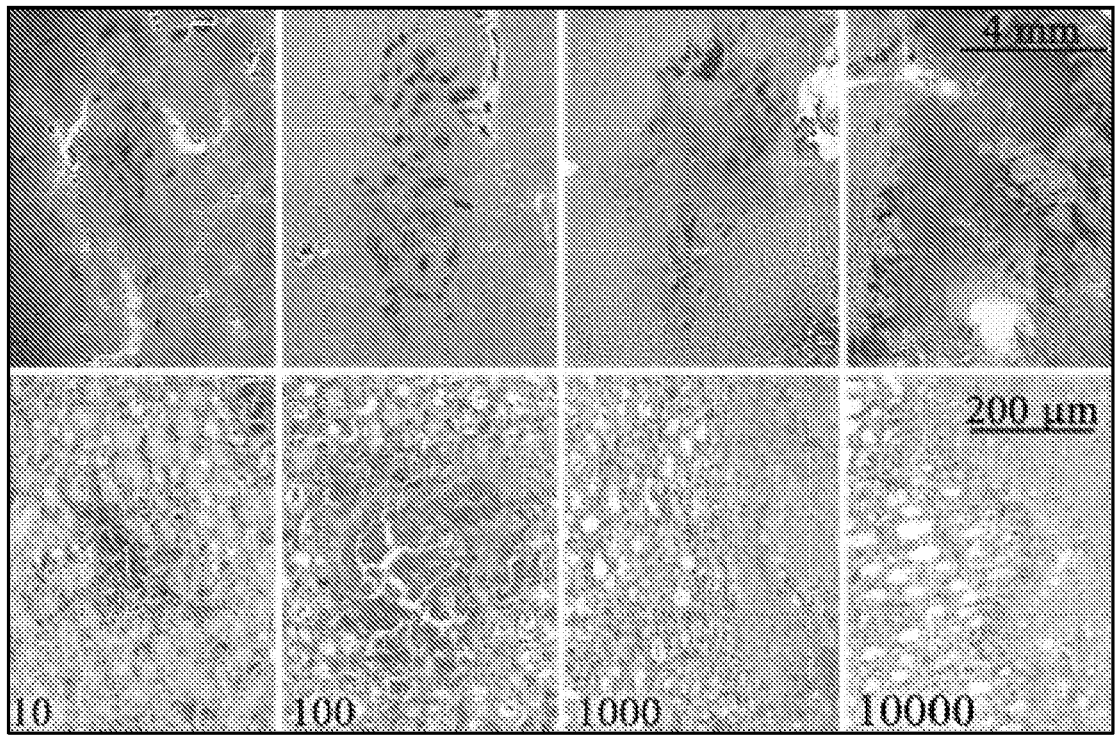
Figure 22:
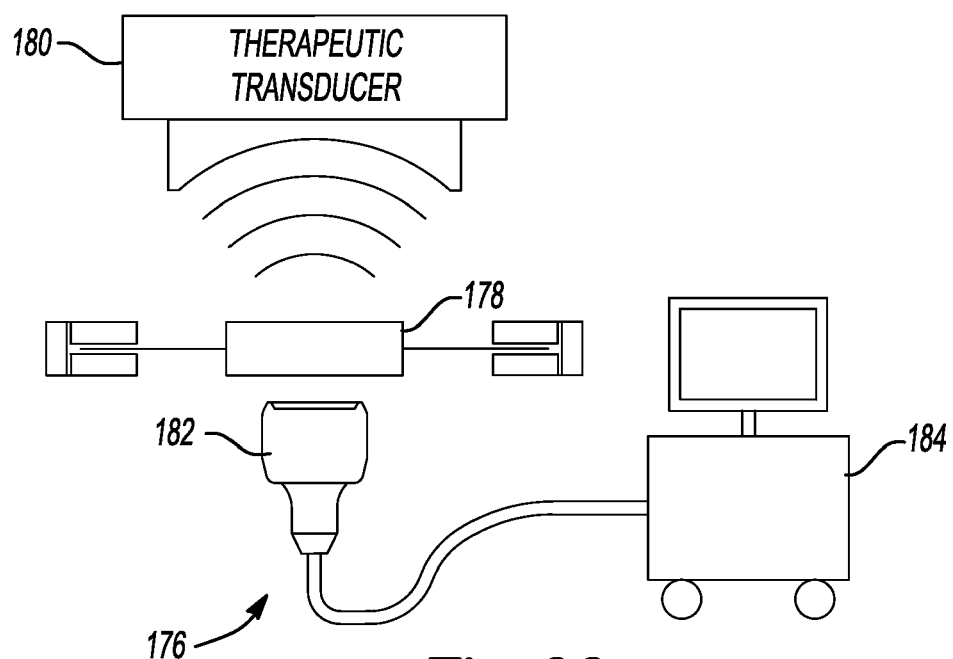
Figure 23:
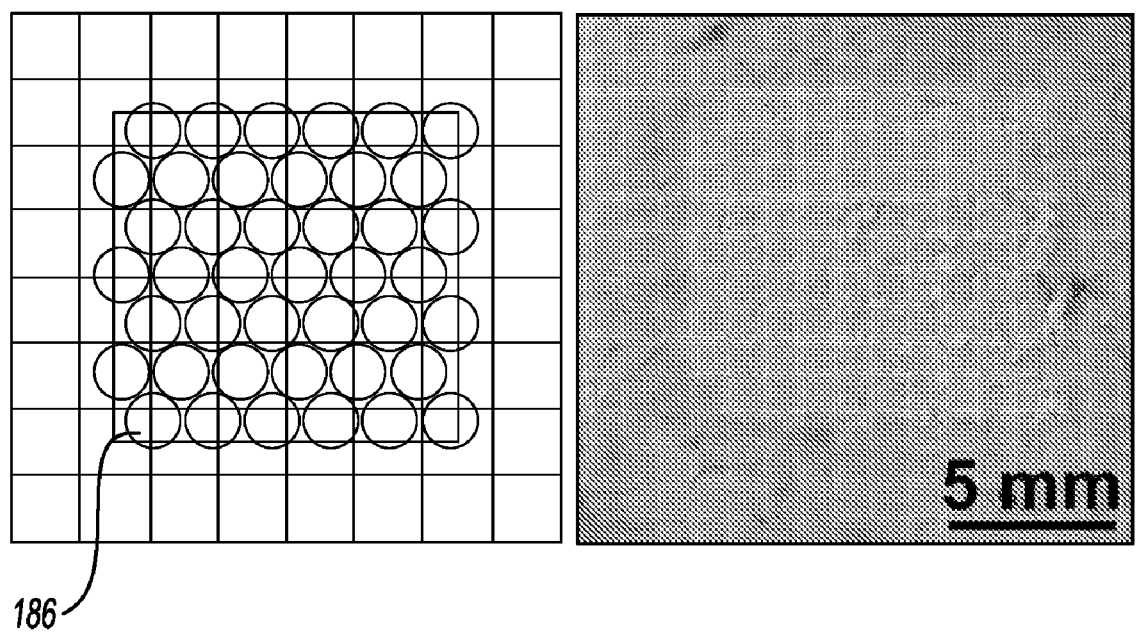
Figure 25:
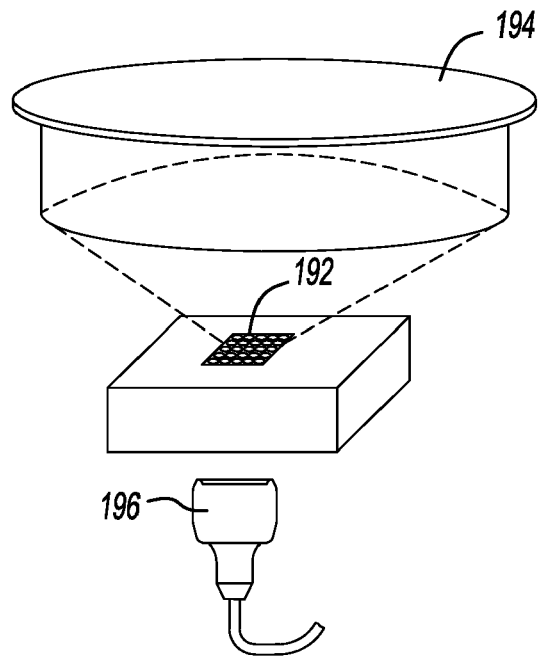
Figure 26:
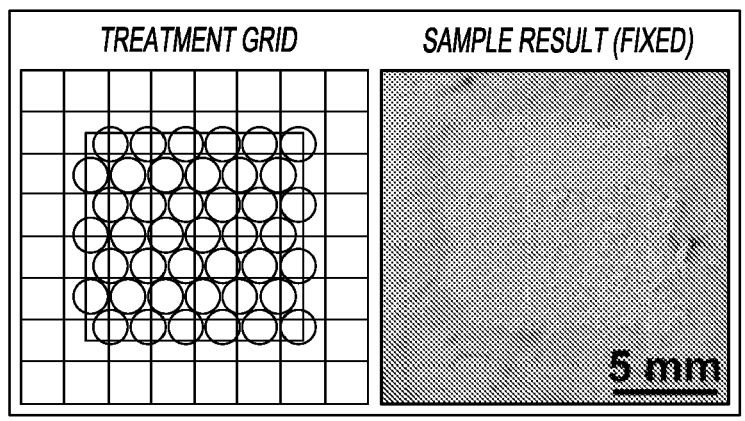
Figure 27:
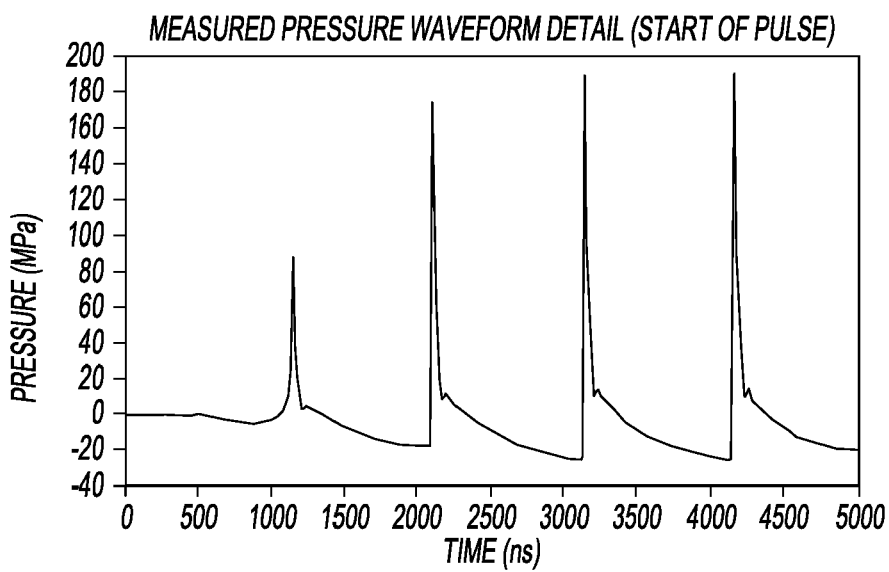
Figure 28:
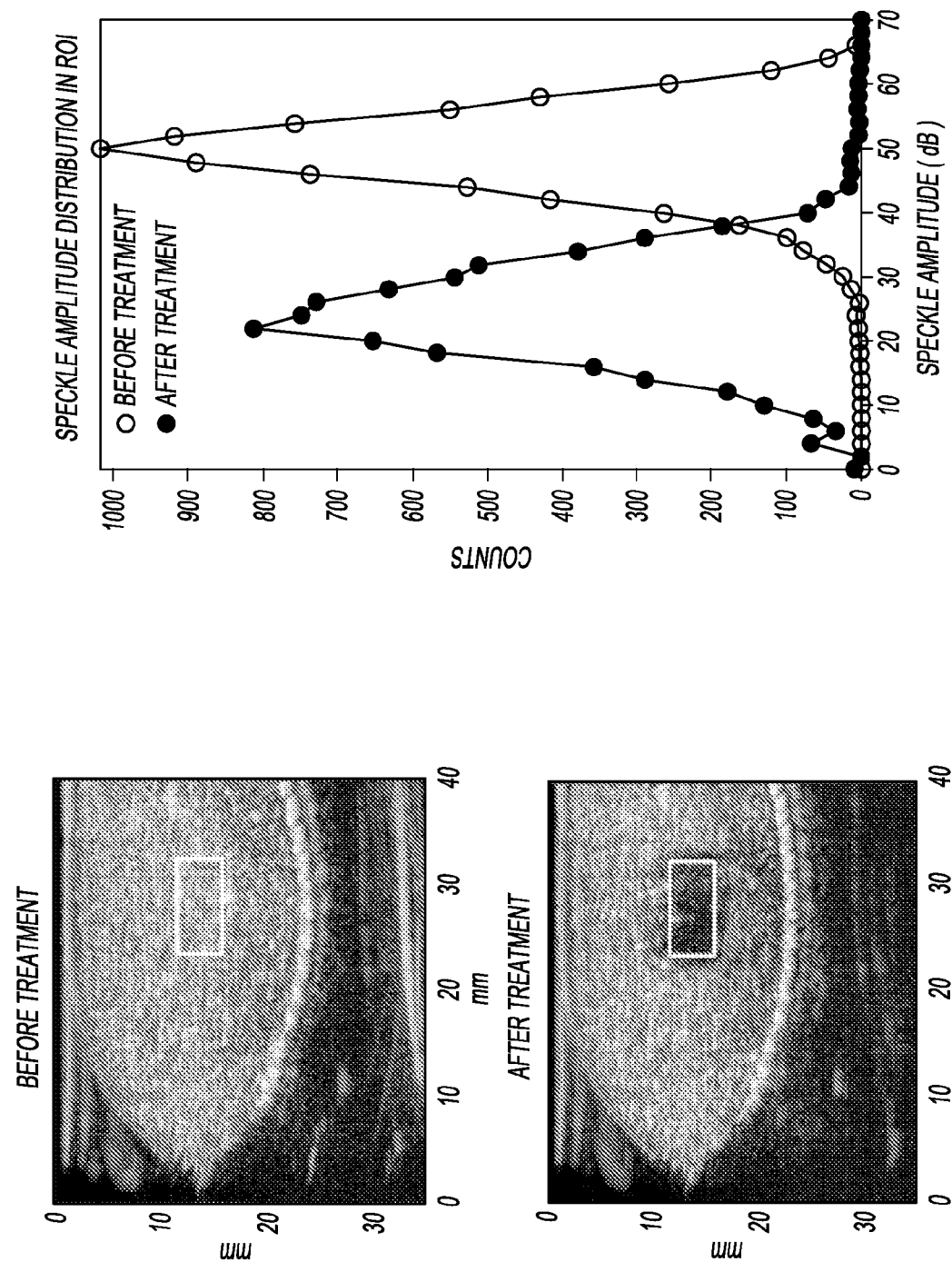
Figure 29:
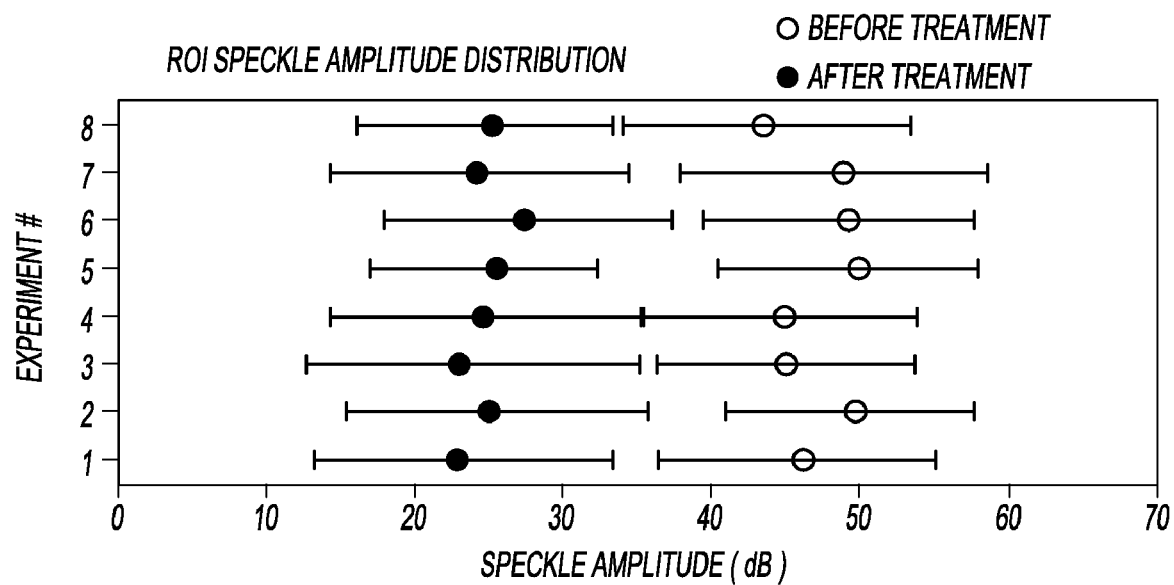
Figure 30:
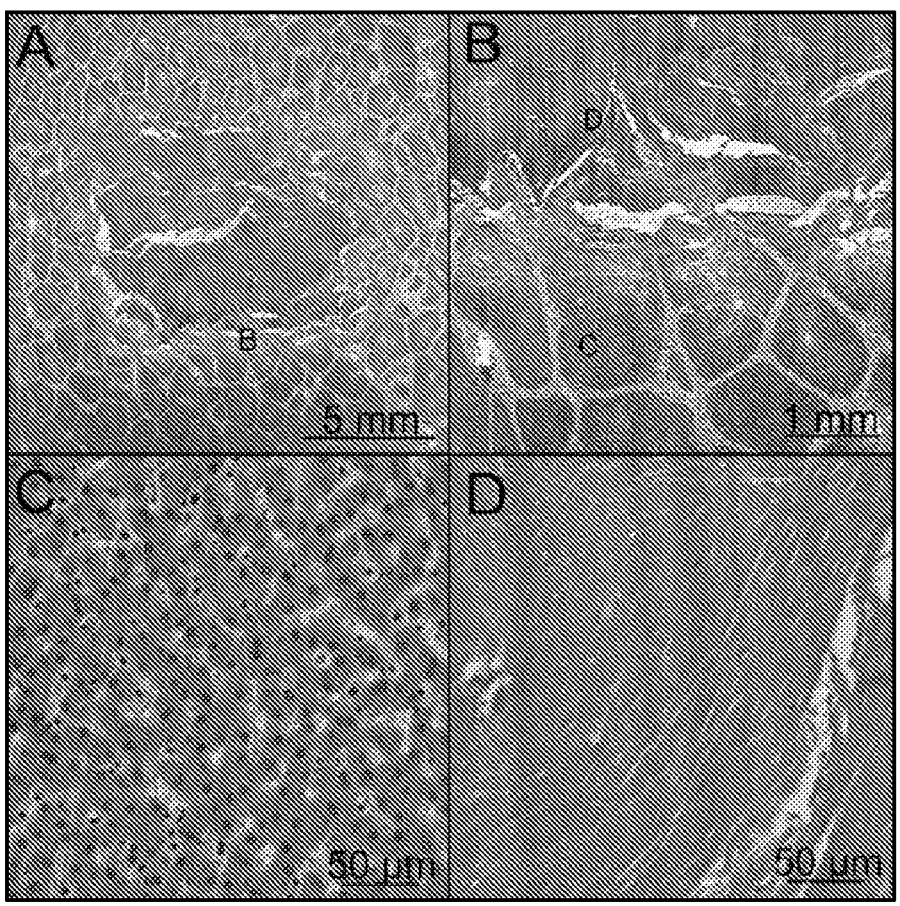
Figure 31:
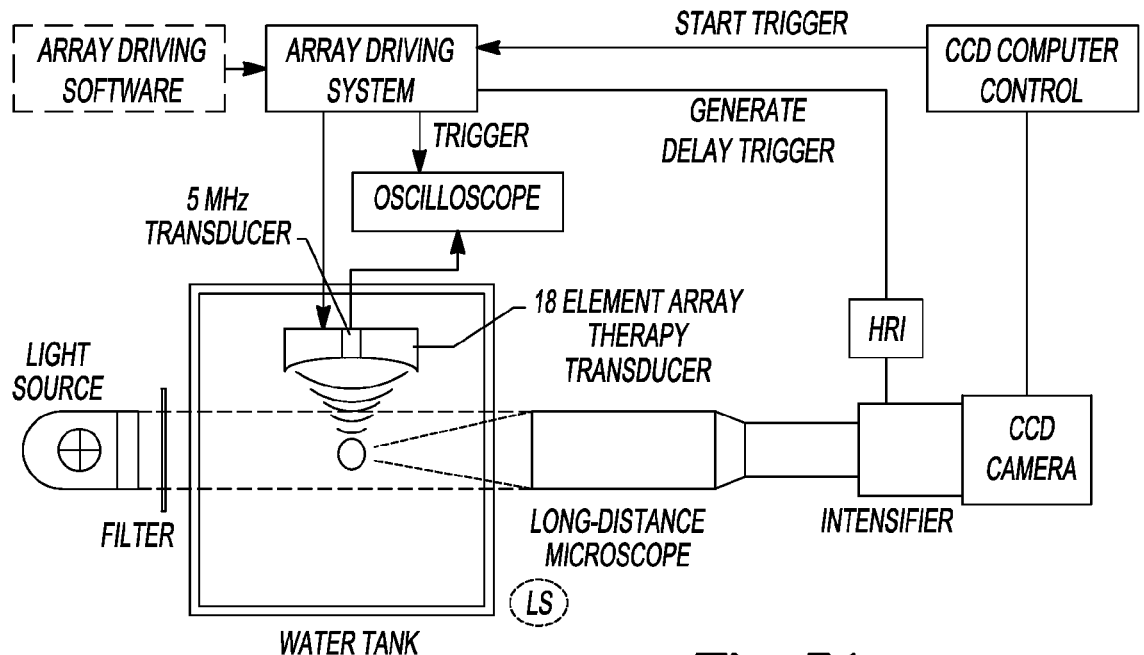
Figure 32:
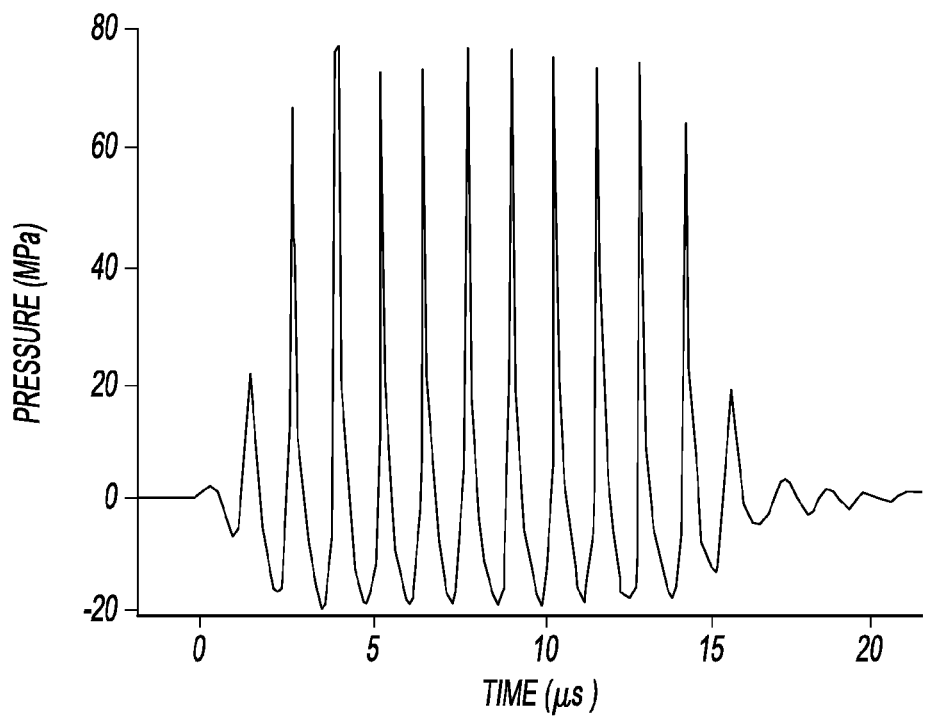
Figure 33:
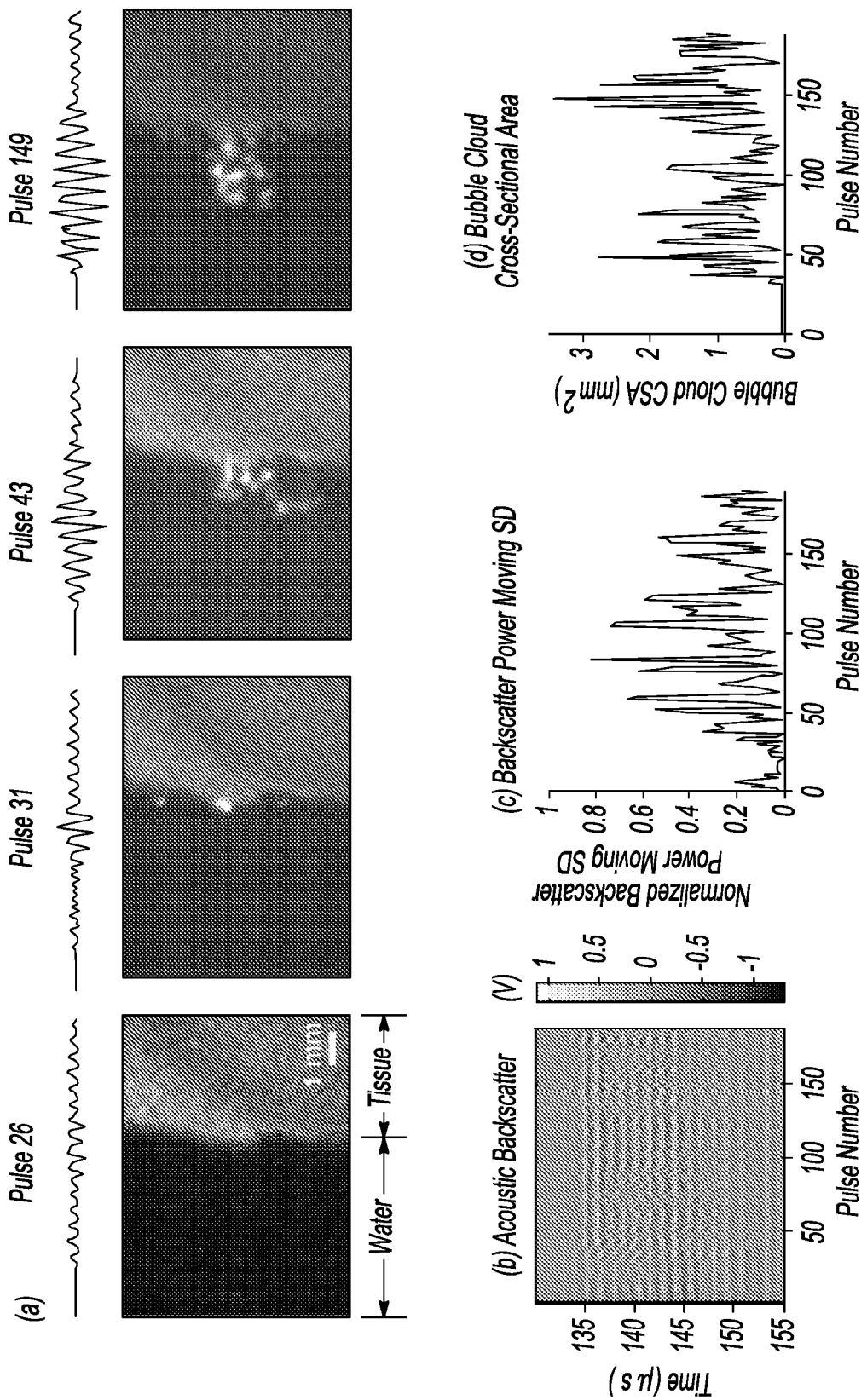
Figure 34:
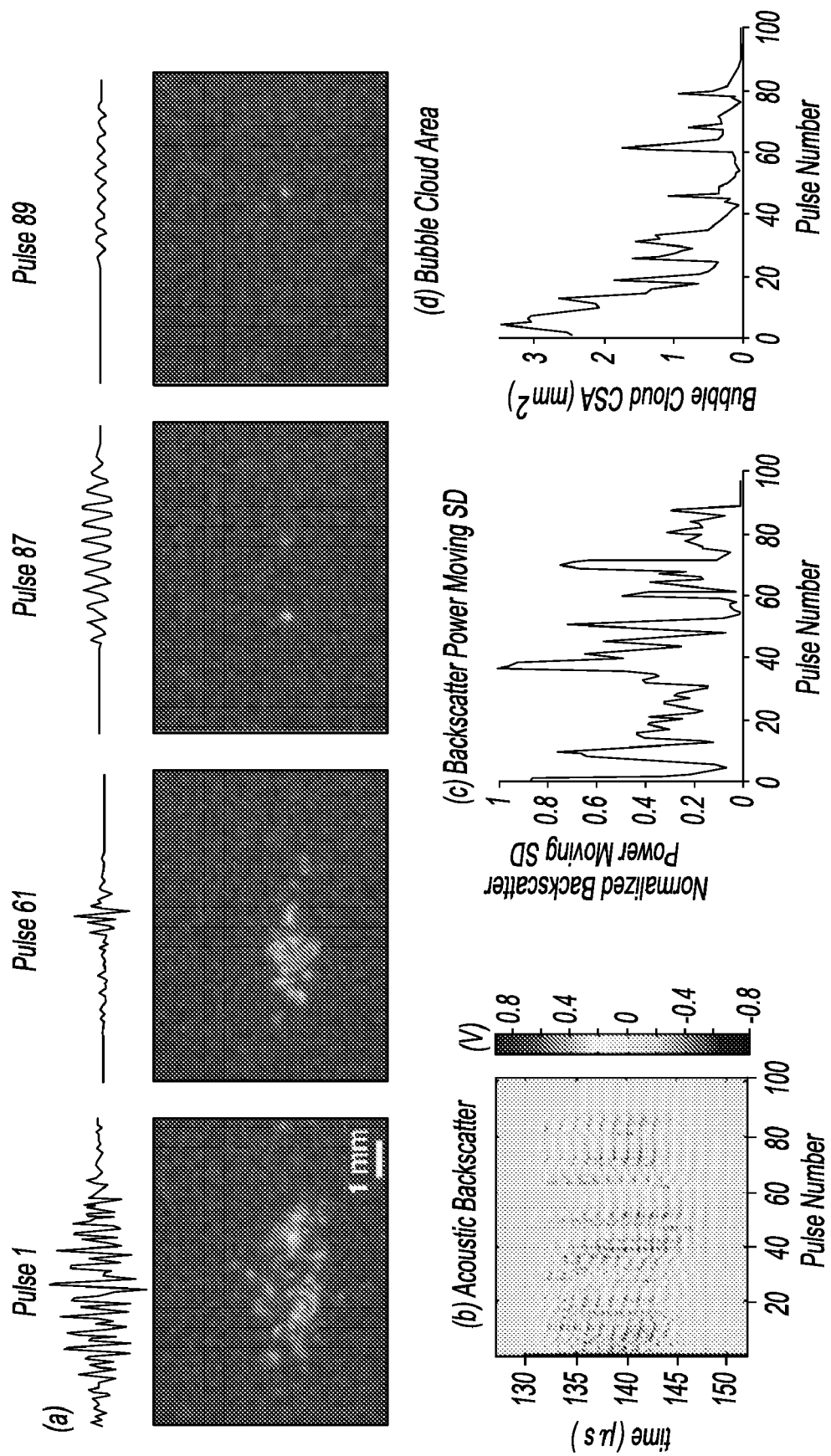
Figure 35:
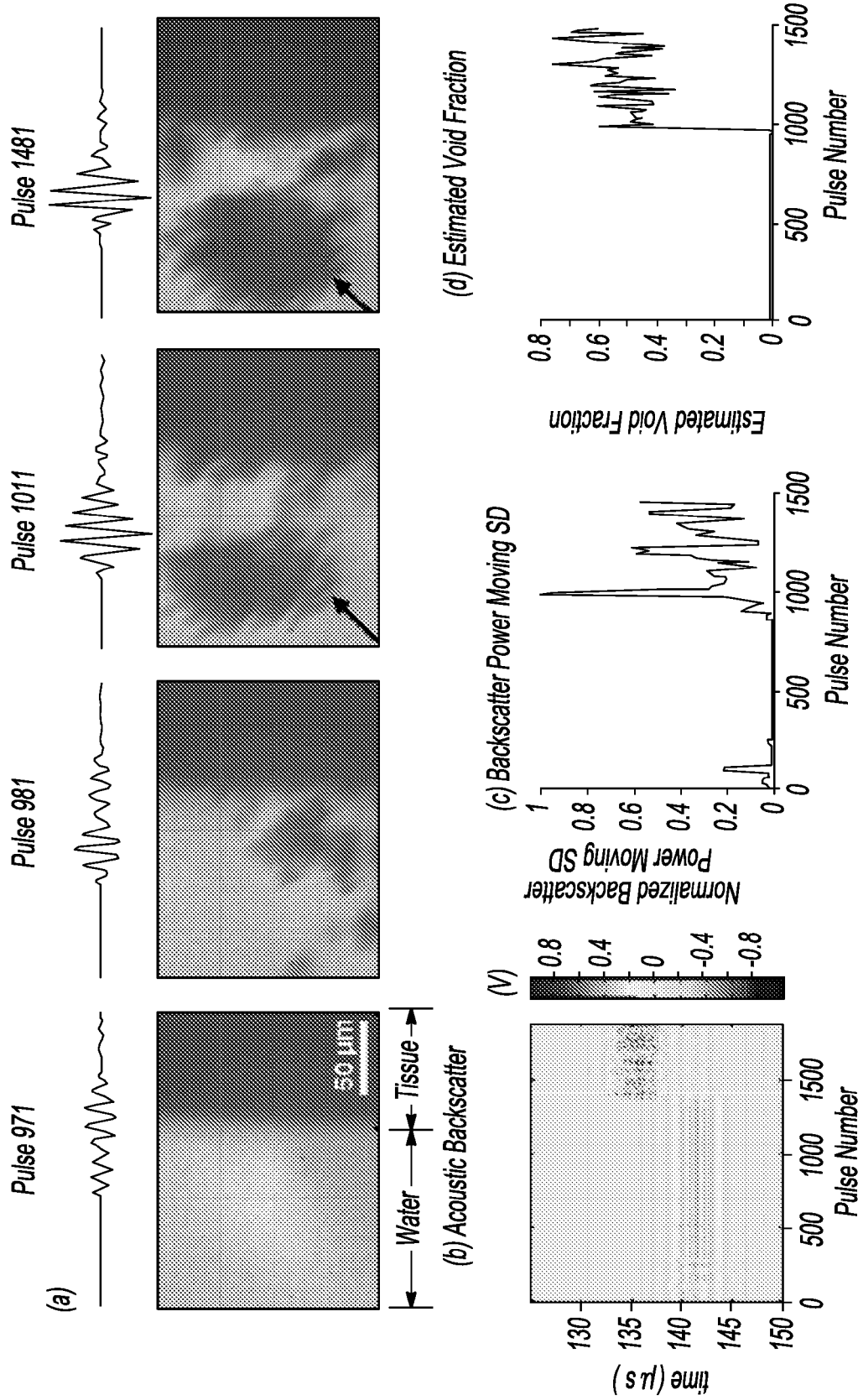
Figure 36:
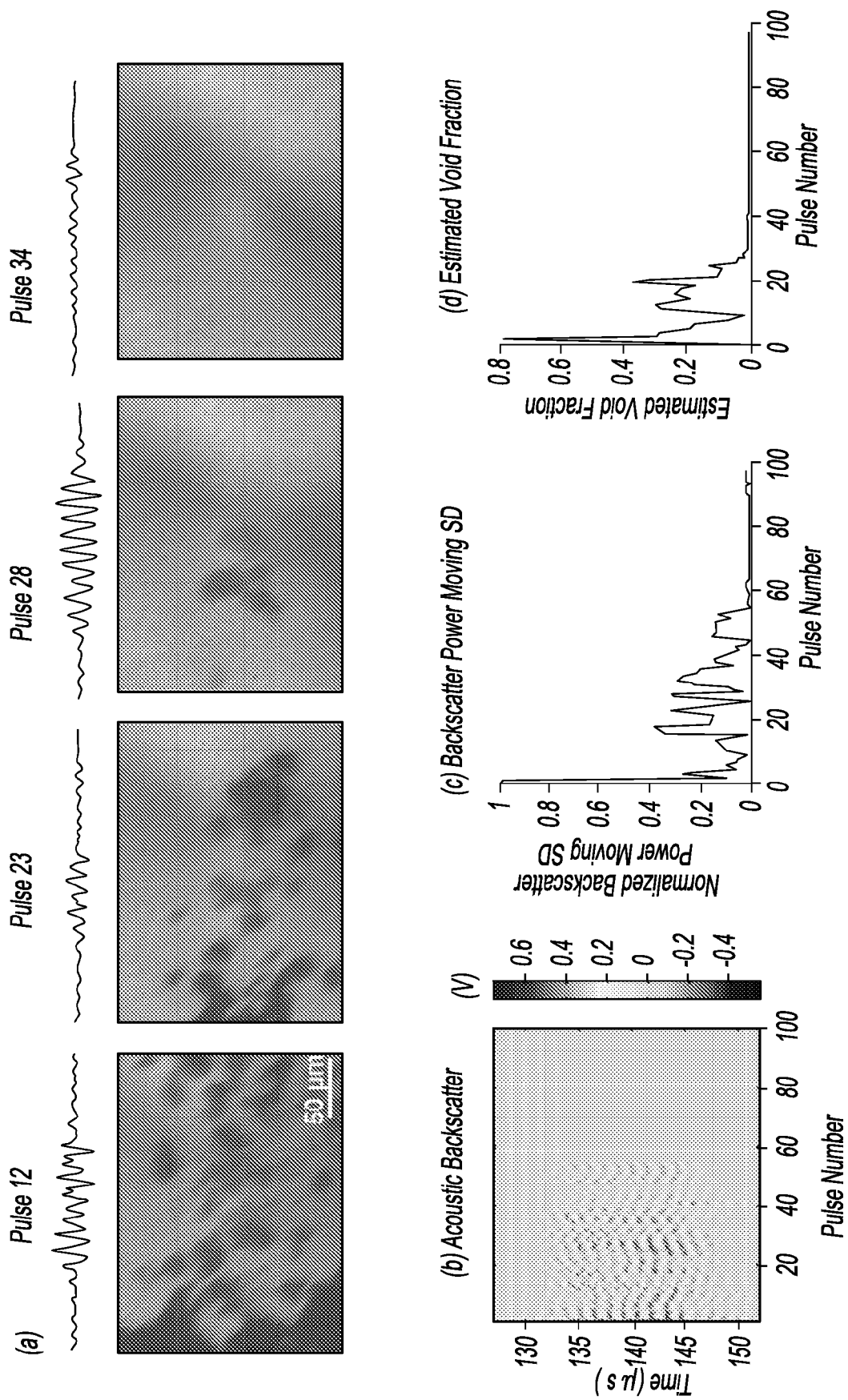
Figure 37:
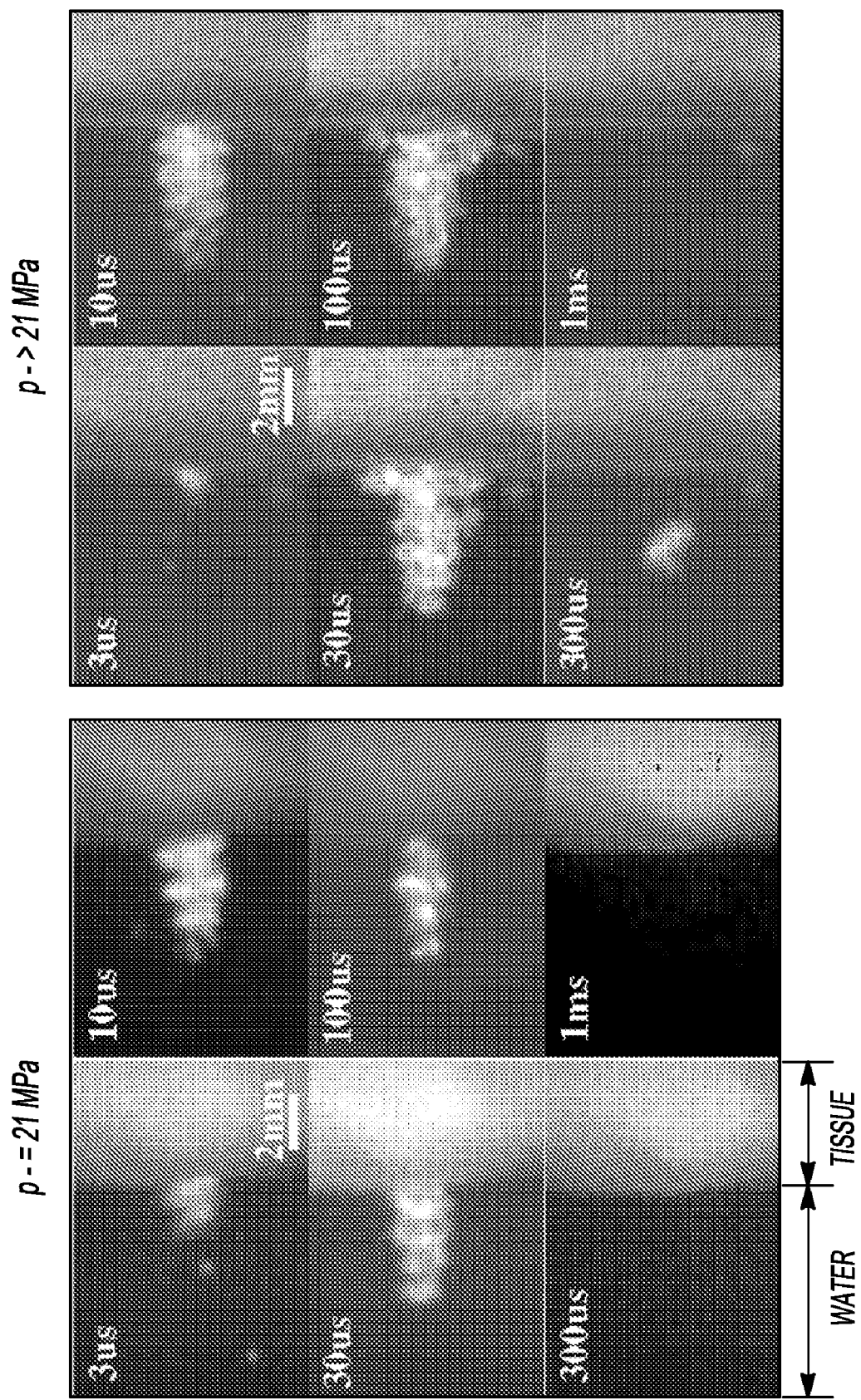

FIG. 19 graphically depicts an acoustic pressure waveform of a 11-cycle ultrasound pulse;

FIG. 20 shows two real-time ultrasound images with a hyperechoic region circled in the right panel;

FIG. 21 is a series of histological slides showing hemorrhagic zones containing cellular debris;

FIG. 22 is a schematic illustration of another exemplary apparatus for performing pulsed cavitational ultrasound therapy constructed in accordance with the teachings of the present disclosure;

FIG. 23 illustrates scanning the therapeutic transducer focus electronically over 42 locations to define a one centimeter square grid in the left panel, while the right panel is a photomicrograph of the treated tissue;

FIG. 24 shows ultrasound images before and after treatment in the two left panels, and histogram distributions of dB scaled speckle amplitude before and after treatment in the right panel;

FIG. 25 is a schematic illustration of another exemplary apparatus for performing pulsed cavitational ultrasound therapy constructed in accordance with the teachings of the present disclosure;

FIG. 26 illustrates a planned treatment grid and photomicrograph of a sample cross-section after treatment;

FIG. 27 graphically depicts the first four cycles of a highly shocked fifty cycle pressure waveform at high amplitude from the therapeutic transducer measured with a fiber optic hydrophone;

FIG. 28 shows sample B-scan images before and after treatment and graphically depicts speckle amplitude before and after treatment;

FIG. 29 graphically depicts treatment region (ROI) speckle amplitude distributions before and after treatment for eight experiments;

FIG. 30 is a series of histology slides from a lesion created through histotripsy;

FIG. 31 schematically illustrates an experimental setup for high speed imaging and acoustic backscatter recording;

FIG. 32 is a graph illustrating the acoustic pressure waveform of a 10-cycle histotripsy pulse in water at the transducer focus with peak rarefactional and compressional pressures of 21 MPa and 76 MPa respectively;

FIG. 33($a$) illustrates a series of bubble cloud images produced at a tissue-water interface for a 25-μs long range-gated acoustic backscatter signal between pulse 26 and 149;

FIG. 33($b$) is an image illustrating acoustic backscatter signals in slow-time and fast-time display, wherein each vertical line is a range-gated voltage trace where voltage is encoded in gray scale relating to FIG. 33($a$);

FIG. 33($c$) is a normalized backscatter power SD as a function of pulse number relating to FIG. 33($a$);

FIG. 33($d$) is an estimated bubble cloud cross-sectional area (CSA) as a function of pulse number, wherein formation of the bubble cloud corresponds to the initiation of the variable acoustic backscatter relating to FIG. 33($a$);

FIG. 34($a$) illustrates a series of bubble cloud images produced in a gelatin phantom for a range-gated acoustic backscatter signal between pulse 1 and 89;

FIG. 34($b$) is an image illustrating acoustic backscatter signals relating to FIG. 34($a$);

FIG. 34($c$) is a normalized backscatter power SD as a function of pulse number relating to FIG. 34($a$);

FIG. 34($d$) is an estimated bubble cloud cross-sectional area (CSA) as a function of pulse number, wherein the disappearance of the bubble cloud and the extinction of acoustic backscatter corresponded in time;

FIG. 35($a$) illustrates a series of bubble cloud images produced at a tissue-water interface between pulse 971 and 1481;

FIG. 35($b$) is an image illustrating acoustic backscatter signals relating to FIG. 35($a$);

FIG. 35($c$) is a normalized backscatter power SD as a function of pulse number relating to FIG. 35($a$);

FIG. 35($d$) is an estimated void fraction of the bubble cloud as a function of pulse number, wherein both the variable acoustic backscatter and bubbles appeared at the $981^{st}$ pulse relating to FIG. 35($a$);

FIG. 36($a$) illustrates a series of bubble cloud images produced at a tissue-water interface between pulse 12 and 34;

FIG. 36($b$) is an image illustrating acoustic backscatter signals relating to FIG. 36($a$);

FIG. 36($c$) is a normalized backscatter power SD as a function of pulse number relating to FIG. 36($a$);

FIG. 36($d$) is an estimated void fraction of the bubble cloud as a function of pulse number, wherein the disappearance of bubbles and the extinction of the variable acoustic backscatter were observed;

FIG. 37 is a series of images illustrating bubble clouds generated by a 10-cycle (14-μs) pulse at peak rarefactional pressure of 21 MPa (left) and >21 MPa (right) at a tissue-water interface, wherein each image is take at a specific time delay (labeled) after the arrival of the histotripsy pulse at the transducer focus (i.e. tissue surface); and FIG. 38 is a series of images illustrating bubble clouds generated inside a gelatin phantom and at a gel-water interface (indicated by arrows), wherein when focusing inside the gelatin phantom one bubble cloud was generated in the gel at the transducer focus and another was generated at the gel-water interface.

DESCRIPTION

I. Global Concepts

The present disclosure makes pulsed cavitational ultrasound, and cavitation assisted processes, such as tissue erosion, bulk tissue fractionization, and drug delivery, predictable and controllable as means for affecting tissues for therapeutic applications. The pulsed cavitational therapy process is similar to lithotripsy, in that soft tissues are progressively mechanically subdivided instead of hard kidney stones. The present process of pulsed cavitational ultrasound is also referred to herein as histotripsy, connoting essentially the lithotripsy of soft tissues. The histotripsy process of the present teachings can, at least in part, involve the creation and maintenance of ensembles of microbubbles and, in some embodiments, the use of feedback in order to optimize the process based on observed spatial-temporal bubble cloud dynamics.

Cavitation has been avoided in the past for therapeutic applications because its results have been unpredictable with regards to both location of damage and thresholds for damage production, and the damage produced has been spatially irregular. However, according to the present disclosure, microbubbles, both in the form of contrast agents and/or other active agents infused into the body or bubbles formed from previous ultrasound exposure, can allow for predictable thresholds, much lower incident intensities for damage production, and can produce much more spatially regular lesions. Moreover, by using pulsed ultrasound, a large acoustic parameter space can be created allowing optimization of parameters for particular therapeutic results. The present disclosure enables cavitation to be used as a viable therapeutic modality in many clinical applications for tissue erosion or fractionation and can include many forms of enhanced drug delivery.

Methods described herein seek to use cavitation, not avoid it, by making the cavitation thresholds in the therapy volume much lower than in surrounding or intervening tissue at or adjacent to transport barriers. By assembling a known, and/or optimally sized distribution of microbubbles in the therapy volume, one can use an effecter frequency low enough to avoid tissue heating and low enough for the sound to propagate through intervening bone, such as ribs or skull. Moreover, the effecter sound field need not be focused or localized if the therapy volume is the only volume with microbubbles tuned by proper pre-sizing of the bubbles to that frequency. Also, any focusing or localization of the effecter field will produce further overall localization of the final lesion. Cavitation also has interesting chemical effects on drugs, which can enhance their intended effect, e.g., effective activation of anticancer drugs. Finally, in the methods outlined herein, feedback of the histotripsy process can be accomplished during tissue erosion or drug delivery treatment either continuously or at intervals.

A key part of the histotripsy process is that each incident ultrasound pulse has two primary functions. First, it produces a small fraction of the desired therapy result. Second, it predisposes the target volume to effective tissue interaction for the next pulse. A set of multiple parameters, including but not limited to intensity, peak negative pressure, peak positive pressure, time of arrival, duration, and frequency, thus allows for many feedback, optimization, and real time monitoring opportunities.

For example, at tissue-fluid interfaces, tissue can be precisely ablated or removed using methods of the present disclosure. Within soft tissues, subdivision can progress until no recognizable cellular structures remain (if desired). At transport barriers, the membranes and obstructions to transport are broken down sufficiently to allow enhanced drug (or other substance) to be driven or transported across. The process allows for enhanced natural diffusion of the deliverable substance and/or active driving or pumping (via cavitation and other acoustic processes) of the deliverable agent.

Once initiated, each pulse produces a bubble cloud, or set of cavitationally active microbubbles, that, as indicated herein, produces part of the tissue therapy and produces microbubbles predisposing the volume to subsequent pulses. After initiation the process can progress with assurance that each pulse effectively participates in the therapy process.

Each individual pulse produces little damage as many pulses, from many thousand to over a million, are required to produce the desired therapeutic effect. In the case of methods of this disclosure, the therapeutic effect can include enhanced substance uptake (drug delivery), drug activation or modification, or a combination of surgery and drug delivery combining the various effects of histotripsy pulse sequences. Since each pulse produces a bubble cloud, it can be easily seen by ultrasound imaging scanners or by special transducers used to detect the ultrasound backscatter. In the case of the imaging systems, the bubbles show up as a bright spot on the image that can be localized to the desired place on the image by moving the therapy transducer focus either mechanically or via phased array electronic focus scanning.

Figure 1:
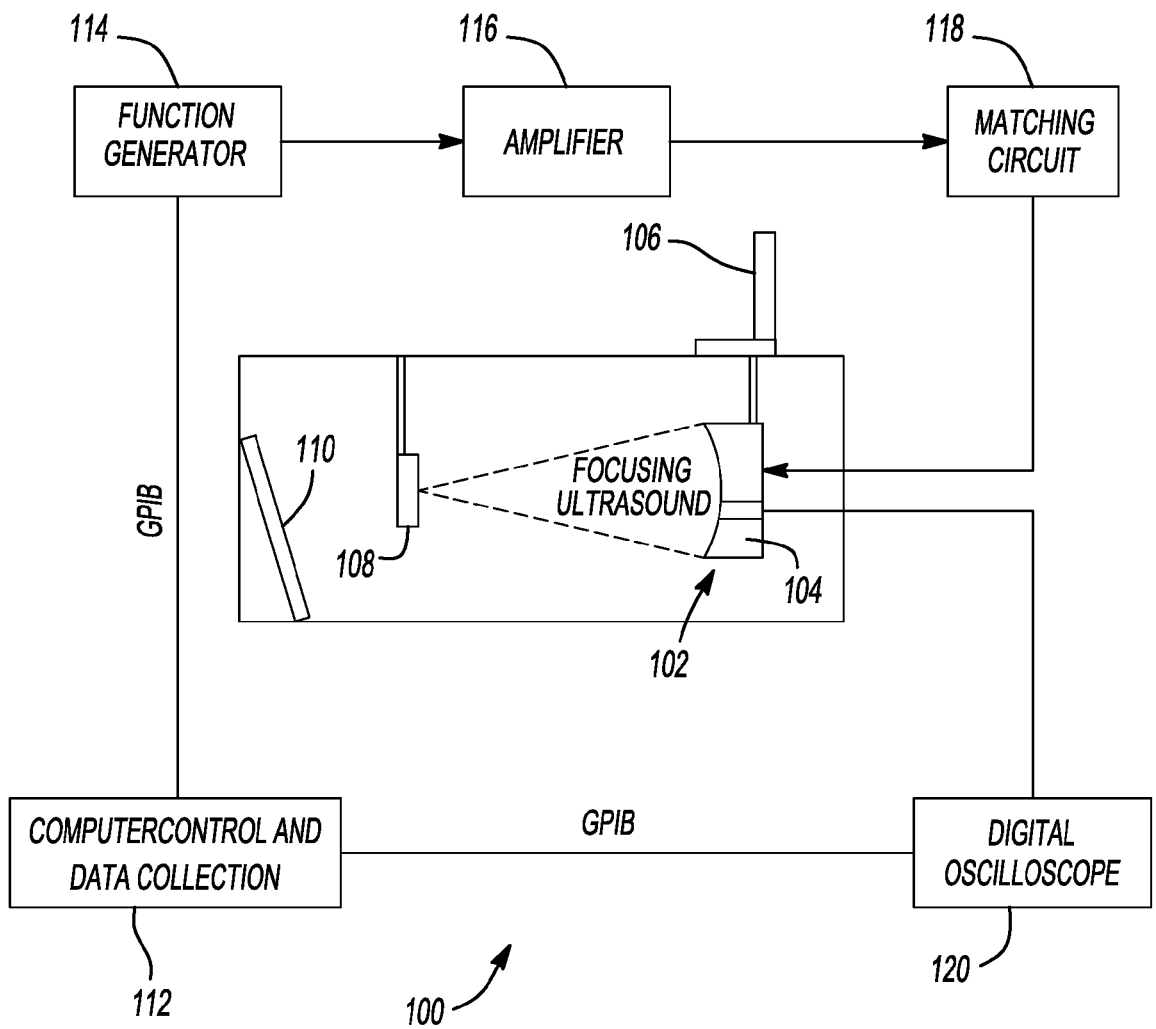

An exemplary apparatus 100 for performing pulsed cavitational ultrasound therapy constructed in accordance with the teachings of the present disclosure is shown in FIG. 1. The apparatus can comprise a therapy transducer 102 and a monitoring transducer 104 coupled to a 3-axis positioning system 106. The therapy transducer 102 and monitoring transducer 104 focus ultrasound onto the target tissue 108, backed by a sound absorber 110. Computer control and data collection 112 is coupled to a function generator 114 that is coupled to an amplifier 116 that is coupled to a matching circuit 118 that is coupled to the transducers 104, 104. Computer control and data collection is also coupled to a digital oscilloscope 120, which is further coupled to the transducers 102, 104.

Pulsed cavitational ultrasound therapy, or the histotripsy process according to the present teachings, can include four sub-processes, namely: initiation, maintenance, therapy, and feedback, which are described in detail herein.

During the initiation step, cavitation nuclei are generated, placed, or seeded in the therapy volume, which is the portion of tissue to which the therapy is directed. The cavitation nuclei reduce the threshold for cavitation by subsequent therapy pulses. Without initiation, the therapy process will not proceed with typical therapy pulses. Initiation assures that the process will progress until it spontaneously (or through active intervention) extinguishes. An important aspect of the initiation step is that it can be terminated or cancelled by using the opposite process, namely the active removal of cavitation nuclei (deletion) in parts of the tissue volume. Pulses can be used to locally cancel cavitation by removing and/or destabilizing cavitation nuclei in order to protect certain volumes or tissue structures from damage. This cancellation process can be viewed as a de-initiation step. Acoustic cavitation is a threshold phenomenon which only occurs when the acoustic intensity or pressure exceeds a certain threshold (cavitation threshold). The cavitation threshold can be locally increased from an initial threshold (first threshold) to a higher threshold through de-initiation (second threshold). Thus, de-initiation can be used to extinguish (opposite to initiation) cavitation locally by active intervention. De-initiation can be achieved by applying ultrasound pulses with a pulse intensity lower than the first cavitation threshold to a selected volume.

During the maintenance step, the presence of micro-nuclei in the therapy volume is actively maintained, assuring that subsequent therapy pulses will produce the appropriate tissue effect. In some embodiments, an appropriate tissue effect can include at lest a portion of the final desired tissue fractionation. The opposite of maintenance would be actively extinguishing the on-going process, perhaps by removing (deleting) microbubbles, as in the cancellation process described herein, or by manipulation of the bubble size, density, or some other property which would protect a desired volume from damage.

During the therapy step, the micro-nuclei (likely small microbubbles) that have been properly initiated and maintained by the preceding processes can be impinged upon by a therapy pulse that produces acute cavitation and tissue fractionation. Each therapy pulse can produce just a small part of the overall therapy effect, which can include mechanical fractionation.

In the simplest process, the therapy transducer initiates, maintains, and produces the desired therapy effect. Thus, for example, a series of high intensity pulses are focused onto the therapy volume sufficient to initiate the bubble clouds. The intensity of the pulses can then be decreased to an intermediate intensity that is below a value that would not otherwise initiate the process. This intermediate intensity is sufficient to sustain the process, otherwise, the process can be re-initiated, if necessary, to produce adequate tissue fractionation. As will be described herein, feedback on the bubble cloud presence or absence can be obtained by monitoring the therapy pulse backscatter from the bubble cloud, where backscatter absence indicates an extinguished process. The backscatter is monitored by the therapy transducer (or subset of therapy transducer array elements) in the receive mode, or by a simple (and separate) monitoring transducer. In some embodiments, multiple transducers can be employed for monitoring feedback.

During the feedback step, each of the prior sub-processes can be monitored to thereby monitor overall therapy progression. The feedback and monitoring step allows for various parameters of the pulsed cavitational ultrasound process to be varied in real time or in stages, if desired, permitting controlled administration of the ultrasound therapy. For example, the process can be terminated, the extent of therapy measured, and the process reinitiated. In particular, the feedback sub-process enables adjustment and tuning of the histotripsy process in precise and controlled ways previously unobtainable.

It should be noted that methods of the present teachings can include variations where each of these four sub-processes can use different methods of energy delivery with different forms of energy and different feedback schemes. Additional details of various embodiments of each subprocess follow.

A. Initiation:

Initiation can comprise an initiation pulse sequence, which is also referred to herein as an initiation sequence or pulse, or initiation. Initiation introduces cavitation threshold-reducing cavitation nuclei and can be accomplished with a therapy transducer using acoustic energy, usually high intensity pulses, at the same frequency as the sustaining and therapy processes. However, initiation can be accomplished by other forms of energy including high intensity laser (or optical) pulses that create a vapor cloud or even a plasma cloud, or x-rays (the ionizing radiation bubble chamber effect). Cavitation nuclei can also be injected intravascularly, or can be injected, or shot (mechanically jetted) into the therapy volume. Thermal means can also be employed wherein elevated temperature, e.g., via a laser, can introduce vapor nuclei (boiling for example). Microbubbles (or proto-bubble droplets, e.g., perfluorocarbon droplets) can be targeted to a therapy volume by molecular or other recognition mechanisms, e.g., antibody against tumor antigens conjugated to nuclei (or proto-nuclei) that would concentrate in or near a tumor. Targeted substances can also be more general than microbubbles or proto-nuclei, such as enzymes, proteins, or other molecules or constructs that enhance the enucleation (gas bubble generation) of dissolved gas into actual microbubbles. Initiation can also occur via mechanical stimulation sufficient to generate cavitation or cavitation nuclei. Initiation, in some embodiments, can be accomplished by an ultrasound imaging transducer whose other role is obtaining feedback information on the histotripsy process or feedback on the therapy itself.

An effective acoustic approach is to use a separate acoustic transducer(s), which can be an array or a plurality of transducers, to initiate, and then use the therapy transducer for the maintenance and therapy sub-processes. This would enable one to use high frequency ultrasound for initiation thus making use of the higher resolution of high frequency transducers or arrays. In this embodiment, initiation could aid in determining the outlines of the therapy volume with high spatial resolution. Therapy could then progress at lower frequencies using the therapy transducer or an array of transducers. For example, lower frequencies would propagate through some bone and air. Thus, methods can include predisposing (initiating) with high resolution and disposing (providing therapy) at a lower frequency that can cover the entire therapy volume. Lower frequency sound propagates more easily through bone and air, enabling methods of the present teachings to be applied to sites beyond such structures. In addition, lower frequency sound has lower thermal absorption, reducing heat generation.

In addition, it can be useful to use de-initiation as an aid in protection of certain volumes in or near the therapy volume. De-initiation can remove or delete microbubbles (or cavitation nuclei). This would greatly increase the cavitation threshold in these sub-volumes thus protecting the tissue therein. For example, in histotripsy of the prostate, the neurovascular bundle just outside the outer capsule of the prostate could be de-initiated (cavitation nuclei deleted or removed) prior to treatment thus protecting this zone and preventing subsequent impotence and incontinence in treated patients.

The de-initiation could be introduced by the therapy transducer (with a special pulse sequence), or could be accomplished by a separate transducer similar to the multi-transducer initiation scheme discussed herein. De-initiation could also be introduced by other energy means as discussed for initiation herein (laser, microwaves, thermal, etc.).

Feedback is important in determining if initiation has occurred because the therapy process will not progress without initiation. In some embodiments, feedback can include monitoring the backscattered signal from the therapy pulses. If no significant backscatter occurs, initiation has not been successful or the process has extinguished and needs to be re-initiated. In some embodiments, feedback can employ one or more of the following: an ultrasound imaging modality that would detect the microbubbles as a hyperechoic zone; a separate transducer to ping (send an interrogation pulse or pulses)

and a transducer to receive it; optical processes wherein optical scattering from the microbubbles (when initiated) is detected; MRI imaging to detect the microbubbles; and low frequency hydrophones, which can detect the low frequency sound produced when bubble clouds expand and contract.

In some embodiments, the feedback scheme can determine the parameters of the existing cavitation nuclei and their dynamic changes with sufficient precision to predict the optimum characteristics or parameters for the next therapy pulse (intensity, peak negative pressure, peak positive pressure, time of arrival, duration, frequency, etc.).

B. Maintenance:

Maintenance can comprise a sustaining pulse sequence, which is also referred to herein as a sustaining sequence, sustaining or maintenance pulse, or maintenance. Maintenance can follow initiation and can also be part of initiation. Generally, once initiated, the cavitation process must be maintained or it will spontaneously extinguish. For example, cavitation can be extinguished when the next therapy pulse does not generate another bubble cloud or does not encounter sufficient nuclei to effectively cavitate at least a portion of the therapy volume. In various embodiments, maintenance is accomplished by the next therapy pulse that creates a bubble cloud that leaves behind sufficient nuclei for the following pulse.

Maintenance can also be accomplished by a separate sustaining transducer producing ultrasound to maintain (sustain) the appropriate nuclei characteristics and population. Thus, the separate transducer(s) described herein for initiation can also maintain (sustain) the nuclei. Likewise, in some embodiments, maintenance can be continued by optical means, x-rays (ionizing radiation), mechanical stimulation, or thermal means. In some embodiments, maintenance can be accomplished by a feedback ultrasound imaging transducer. For example, if a slow therapy pulse repetition frequency is desired (e.g., to prevent tissue heating), sustaining sequences or pulses (of lower intensity, for example) can be interleaved between the therapy pulses to sustain the microbubble or nuclei population and characteristics necessary to allow the next therapy pulse to be effective. These interleaved sustaining sequences can be applied by the various means enumerated herein for maintenance or initiation.

The schemes outlined under initiation for deleting or cancelling the cavitation nuclei in certain volumes to protect tissue from the histotripsy process can be applied to effectively delete nuclei while maintaining other parts of the therapy volume. Thus, in some embodiments, active de-maintenance procedures can be instituted using the various energy modalities outlined herein, where some therapy volume is maintained for therapy progression while and other volumes are actively protected or the cavitation nuclei in these volumes can be simply allowed to extinguish passively. Maintenance feedback and monitoring can be similar to the initiation step feedback outlined herein, except in some embodiments lower pulse intensities can be used compared to pulses used in the initiation step.

C. Therapy:

Therapy can comprise a therapy pulse sequence, which is also referred to herein as a therapy sequence, therapy pulse, or therapy. The therapy process is the interaction of ultrasound on existing cavitation nuclei to produce sufficiently vigorous cavitation to mechanically subdivide tissue within the therapy volume. Therapy energy in the histotripsy process can be acoustic (e.g., ultrasonic). The transducer or transducers can be either single focus, or multi-focus, or phased arrays where the focus can be scanned in 1, 2, or 3-dimensions. The therapy transducer(s) can be contiguous spatially or can be separated spatially, using multiple windows into the therapy volume. The transducers can also operate at different frequencies individually or as an overall ensemble of therapy transducers. The therapy transducer(s) can also be mechanically scanned to generate larger therapy zones and/or a combination of mechanically and electronically (phased array) scans can be used. The therapy transducer(s) can also be used, as outlined herein, as sources of initiation and/or maintenance processes and procedures. The therapy transducer(s) can be intimately involved in the feedback processes and procedures as sources of interrogation sequences or as receivers (or even imagers). Thus, in some embodiments, the therapy pulses (or sequences) can initiate, maintain, and do therapy.

The multiplicity of transducers enables various embodiments where one of the therapy transducers could operate at a significantly lower frequency from the other(s). For example, the higher frequency transducer can initiate (predispose) and the lower frequency transducer can do the mechanical fractionation (dispose).

In some embodiments, one or more low frequency transducers can act as a pump with the other transducer(s) sending pulses (therapy, initiation, maintenance, or feedback) propagating along with the low frequency pump. For example, if a higher frequency, short therapy pulse arrives in the therapy volume in a particular relation to the phase of the low frequency pump pulse, multiple effects can be obtained therefrom depending on this relative phase relationship. If the higher frequency pulse rides on the peak rarefactional (negative pressure) portion of the pump, the peak negative (rarefactional) pressure of the high frequency pulse can be increased to enhance its ability to cavitate available nuclei. Thus, the pump acts as a significant enhancer of therapy effect. The same arrangement can be employed to enhance initiation.

If the higher frequency pulse arrives at the therapy volume on the peak positive pressure of the pump, the cavitational effect is reduced but can enhance the ability of the high frequency waveform to delete cavitational nuclei. Thus, it can have a de-initiation or cancellation function. Also, if the pump and therapy pulse arrive at different propagation angles, it can serve to spatially sharpen the effective focus of the therapy pulse. The maximum sharpening effect occurs when the pulses arrive having been propagated in opposite directions or 90 degrees from each other.

The therapy transducers (high and low frequency) can also operate in conjunction with the feedback transducers to enhance effects. For example, if an imaging transducer is used for feedback on initiation, maintenance, or therapy, it can be used in a similar way as discussed herein to enhance the detection of microbubbles or nuclei. That is, if the imaging pulse arrives in the imaging volume on the rarefactional trough of the pump pulse, the bubbles will have expanded and will be relatively hyperechoic. If the imaging pulse arrives on the peak positive pressure, the nuclei or microbubbles will be smaller in size (compressed) and the image in this interaction zone will be relatively hypoechoic. Thus, by using a difference image, one will see only microbubble activity as the other tissue echoes will be constant (same) in both images.

In some embodiments, the therapy pulse can be used as a pump and the imaging pulse can be propagated therewith. If one or more therapy pulses are focused on a therapy volume or portion of a therapy volume, the intensity can be greater in the focused therapy volume. Therefore, the effect on bubbles will be greater in the focused therapy volume and less away from the focused therapy volume. By co-propagating the imaging and therapy pulse alternately, with the imaging pulse riding on the peak rarefactional pressure of the therapy pulse and the peak positive pressure of the therapy pulse, a difference image will show the greatest difference near the focused therapy pulse(s). The difference will be less away from the focused therapy pulse(s). Thus, this scheme allows direct imaging of the therapy pulse beam pattern. This can be used to identify and locate where the maximum tissue damage will occur in the therapy volume before treatment.

D. Feedback & Monitoring:

In some embodiments, feedback enables assessment of parameters related to noninvasive image guided therapy or drug delivery. The methods and devices depend on the fact that the actual therapeutic effect is the progressive mechanical subdivision of the tissue that can also provide enhanced drug transport (or other therapeutic or diagnostic effect) over one or more therapy pulses. Thus, the tissues exposed to the histotripsy process are changed physically. These physical changes are much more profound than changes produced by competing therapies. Furthermore, embodiments of the present teachings make it possible to monitor the therapeutic effectiveness both during and after the therapy process. Whereas, this type of feedback monitoring has been unobtainable in previous noninvasive therapy procedures.

In some embodiments, feedback and monitoring can include monitoring changes in: backscatter from bubble clouds; speckle reduction in backscatter; backscatter speckle statistics; mechanical properties of tissue (i.e., elastography); shear wave propagation; acoustic emissions, and electrical impedance tomography.

Backscatter from Bubble Clouds: This feedback method can determine immediately if the histotripsy process has been initiated, is being properly maintained, or even if it has been extinguished. For example, this method enables continuously monitored in real time drug delivery, tissue erosion, and the like. The method also can provide feedback permitting the histotripsy process to be initiated at a higher intensity and maintained at a much lower intensity. For example, backscatter feedback can be monitored by any transducer or ultrasonic imager. By measuring feedback for the therapy transducer, an accessory transducer can send out interrogation pulses. Moreover, the nature of the feedback received can be used to adjust acoustic parameters (and associated system parameters) to optimize the drug delivery and/or tissue erosion process.

Backscatter, Speckle Reduction: Progressively mechanically subdivided tissue, in other words homogenized, disrupted, or eroded tissue, results in changes in the size and distribution of acoustic scatter. At some point in the process, the scattering particle size and density is reduced to levels where little ultrasound is scattered, or the amount scattered is reduced significantly. This results in a significant reduction in speckle, which is the coherent constructive and destructive interference patterns of light and dark spots seen on images when coherent sources of illumination are used; in this case, ultrasound. After some treatment time, the speckle reduction results in a dark area in the therapy volume. Since the amount of speckle reduction is related to the amount of tissue subdivision, it can be related to the size of the remaining tissue fragments. When this size is reduced to sub-cellular levels, no cells are assumed to have survived. So, treatment can proceed until a desired speckle reduction level has been reached. Speckle is easily seen and evaluated on standard ultrasound imaging systems. Specialized transducers and systems can also be used to evaluate the backscatter changes.

Backscatter, Changes in Speckle Statistics: Speckle in an image persists from frame to frame and changes little as long as the scatter distribution does not change and there is no movement of the imaged object. However, long before the scatters are reduced enough in size to cause speckle reduction, they may be changed sufficiently to be detected by signal processing and other means. This family of techniques can operate as detectors of speckle statistics changes. For example, the size and position of one or more speckles in an image will begin to decorrelate before observable speckle reduction occurs. Speckle decorrelation, after appropriate motion compensation, can be a sensitive measure of the mechanical disruption of the tissues, and thus a measure of therapeutic efficacy. This feedback and monitoring technique permits early observation of changes resulting from the histotripsy process, and can identify changes in tissue before substantial or complete tissue erosion occurs. For example, this method can be used to monitor the histotripsy process for enhanced drug delivery where tissue is temporally disrupted and tissue erosion is not desired.

Also included in embodiments of this method is speckle decorrelation by movement of scatters in an increasingly fluidized therapy volume. For example, in the case where partial or complete tissue erosion is desired.

Elastography: As the tissue is further subdivided (homogenized, disrupted, or eroded), its mechanical properties change from a soft but interconnected solid to a viscous fluid or paste with few long-range interactions. These changes in mechanical properties can be measured by various imaging modalities including MRI and ultrasound imaging systems. For example, an ultrasound pulse can be used to produce a force (i.e., a radiation force) on a localized volume of tissue. The tissue response (displacements, strains, and velocities) can change significantly during histotripsy treatment allowing the state of tissue disruption to be determined by imaging or other quantitative means.

Shear Wave Propagation Changes: The subdivision of tissues makes the tissue more fluid and less solid and fluid systems generally do not propagate shear waves. Thus, the extent of tissue fluidization provides opportunities for feedback and monitoring of the histotripsy process. For example, ultrasound and MRI imaging systems can be used to observe the propagation of shear waves. The extinction of such waves in a treated volume is used as a measure of tissue destruction or disruption. Moreover, dedicated instrumentation can be used to generate and measure the interacting shear waves. For example, two adjacent ultrasound foci might perturb tissue by pushing it in certain ways. If adjacent foci are in a fluid, no shear waves propagate to interact with each other. If the tissue is not fluidized, the interaction would be detected with external means, for example, by a difference frequency only detected when two shear waves interact nonlinearly, with their disappearance correlated to tissue damage.

Acoustic Emission: As a tissue volume is subdivided, its effect on microbubbles is changed. For example, bubbles may grow larger and have a different lifetime and collapse changing characteristics in intact versus fluidized tissue. Bubbles may also move and interact after tissue is subdivided producing larger bubbles or cooperative interaction among bubbles, all of which can result in changes in acoustic emission. These emissions can be heard during treatment and they change during treatment. Analysis of these changes, and their correlation to therapeutic efficacy, enables monitoring of the progress of therapy.

Electrical Impedance Tomography: An impedance map of a therapy site can be produced based upon the spatial electrical characteristics throughout the therapy site. Imaging of the conductivity or permittivity of the therapy site of a patient can be inferred from taking skin surface electrical measurements. Conducting electrodes are attached to a patient's skin and small alternating currents are applied to some or all of the electrodes. One or more known currents are injected into the surface and the voltage is measured at a number of points using the electrodes. The process can be repeated for different configurations of applied current. The resolution of the resultant image can be adjusted by changing the number of electrodes employed. A measure of the electrical properties of the therapy site within the skin surface can be obtained from the impedance map, and changes in and location of the bubble cloud and histotripsy process can be monitored using this process.

E. Histotripsy Parameter Adjustments:

In some embodiments of the present teachings, opportunities exist to adjust or customize the histotripsy process for particular applications. By changing various parameters, the histotripsy process can be initiated by high-intensity pulses and maintained by low intensity pulses, therapy intensity can be varied, and changes in maintenance (sustaining) pulses can be realized. The aforementioned feedback and monitoring methods readily allow these directed parameter adjustments and the effects thereof to be observed during the histotripsy process, in real time, and/or permit therapy progress measurement in stages, where therapy can be reinitiated as desired or as necessary.

In some embodiments, cavitation induced soft tissue erosion can be enhanced by a process in which a short, high-intensity sequence of pulses is used to initiate erosion and lower intensity pulses are employed to sustain the process. This strategy generates cavitation nuclei using high intensity pulses which provide seeds for the subsequent lower intensity pulses to sustain cavitation and erosion. If lower intensity pulses are used for erosion, but instantaneous initiation is ensured by a short higher intensity sequence, the energy spent before the initiation can be saved and can reduce thermal complications. By using the high intensity initiating sequence strategy, erosion can be sustained at a much lower average intensity and with less overall propagated energy. This can help to reduce thermal damage to overlying and surrounding tissue, which has been a general concern for ultrasound therapy. It can also reduce the probability of thermal damage to the therapy transducer.

In some embodiments, a high intensity initiating sequence can help to increase the probability of erosion at lower intensities with only slight increase in total propagated energy. Consequently, the intensity threshold for generating erosion is significantly lower using such an initiating sequence. For example, the estimated intensity threshold for generating erosion is defined as the probability of erosion at 0.5 is at a spatial-peak pulse-average intensity ($I_{SPPA}$) of 3220 W/cm². The probability of erosion at 0.875 is achieved at ISPPA of 2000 W/cm² by adding a short initiating sequence (200 3-cycle pulses) and very little overall increase in propagated energy (0.005%). As a result, the initiating sequence lowers the erosion threshold from ISPPA 3220 W/cm² to <2000 W/cm². In addition, the initiating sequence increases the erosion rate through ensuring an instantaneous initiation of cavitation such that no energy is wasted on acoustic pulses preparing for initiation though producing no erosion.

Without wishing to be bound by theory, the following mechanism has been proposed to explain the increased probability of erosion when using one or more high intensity initiation pulses followed by lower intensity pulses. A cloud of microbubbles is generated by the initiating sequence, providing a set of cavitation nuclei for the lower intensity pulses. This shares the same principles with microbubble enhanced therapy, which artificially introduces cavitation nuclei to tissue and makes cavitation easier to achieve. The initiating sequence can be considered as a source of self-generated localized microbubbles. The advantage of using the initiating sequence is that cavitation nuclei can be generated at the desired location, instead of being present throughout the entire organ which might result in greater collateral damage.

Some possibilities regarding details of the mechanism might be extracted from the initiated and extinguished time results. The initiated time result showing cavitation lasts for shorter duration after each successive initiation implies either depletion of certain essential components to sustain cavitation (e.g. cavitation nuclei) over time, or increased interferences (e.g. shadowing from larger bubbles). The observation of random extinguished time between adjacent active cavitation periods may suggest initiation of active cavitation as a threshold phenomenon, which only occurs when the density or population of microbubbles within a certain size range exceeds a threshold.

Furthermore, duration of active cavitation does not depend on the number of pulses within the initiating sequence. An initiating sequence containing more pulses does not seem to provide longer active cavitation or more erosion. For example, increasing the number of pulses within the initiating sequence does not elongate the initiated time, the probability of erosion, or the erosion rate. More pulses in the initiating sequence may generate a similar net number of cavitation nuclei for the sustaining pulses, possibly by breaking up as many cavitation nuclei as they create. Therefore, only the minimum number of high intensity pulses (i.e. the minimum energy) required for initiation is necessary.

Once cavitation is extinguished, active cavitation seldom reinitiates spontaneously and can be shorter in duration if reinitiated. Consequently, high intensity pulses can be used to reinitiate, instead of waiting for a spontaneous reinitiation by the lower intensity pulses. A feedback strategy can be formed where the high intensity initiating sequence is used to initiate cavitation, lower intensity pulses are used to maintain it, and the initiating sequence used again (when necessary) to reinitiate it when extinction is detected. This strategy can accomplish tissue perforation or fractionation with lower propagated energy, reducing heating of overlying tissue and the transducer, which is a concern for any ultrasound therapy.

If calculated using active cavitation time (initiated time), the erosion rates can be similar with and without the initiating sequence, but the variances can be high in both cases. The variability of biological tissue may contribute to this high variance. The quality of cavitation may also need to be quantified as well as the temporal characteristics for a more accurate correlation with erosion.

Tissue inhomogeneity may also affect the cavitation induced erosion process. For example, atrial septum and atrial wall tissues both consist of two layers of membrane tissue with soft muscle in between. Membrane can be harder to erode than soft muscle tissue and can require a higher intensity. An efficient paradigm can be to erode the membrane tissue with higher intensity pulses and erode the soft tissue with lower intensity pulses. Acoustic parameters can be chosen specifically for the tissue type as well as the application (e.g., erosion, necrosis) to achieve higher efficiency.

Intensity thresholds of histotripsy methods can also be varied as needed. The feedback and monitoring methods of the present disclosure allow changes in intensity to be observed in real time or in stages as desired. Changes in intensity can identify and tune intensity thresholds for ultrasound induced tissue erosion in order to achieve localized and discrete soft tissue disruption.

Adjustment of pulse intensity can result in changes in erosion characterized by axial erosion rate, perforation area and volume erosion rate. For example, axial erosion is faster with higher intensity at $I_{SPPA} \leq 5000$ W/cm². However, at $I_{SPPA} \geq 5000$ W/cm², axial erosion is slower with increasing intensity. It should be noted that this is contradictory to the common expectation that the axial erosion rate would increase with increasing $I_{SPPA}$ because higher $I_{SPPA}$ results in more propagated energy as the same PD and PRF were used in all the exposures. Without wishing to be bound by theory, it is believed that the observed decrease in axial erosion rate may be due to shadowing effects. For example, supposing each pulse creates a cloud of spatially and temporally changing microbubbles, the number of microbubbles and overall size of the cloud generated by each ultrasound pulse will most likely increase at higher intensity. If the intensity is too high and a dense bubble cloud forms (including perhaps large but ineffectual bubbles), shadowing may occur wherein ultrasound energy is scattered or absorbed before it reaches the target tissue.

The same principle may explain why the perforation area is significantly larger than the area where tissue is exposed to pulses with intensity greater than the erosion threshold at $I_{SPPA} \geq 7000$ W/cm². Although shadowing in the central portion of the beam slows the erosion at high intensity, a large number of bubbles may increase local scattering and, therefore, increase peripheral erosion beyond the beam cross-sectional area, defined at >3220 W/cm².

The increase in the perforation area can roughly compensate for the reduction in the axial erosion rate, resulting in an overall trend toward an increasing volume erosion rate with increasing intensity. Both the perforation area and the volume erosion rate can increase with increasing intensity.

Additional parameter adjustments can affect the structure of tissue lesions produced by the histotripsy process. For example, adjustment of specific acoustic parameters, such as pulse sequence repetition frequency (PRF) and sustaining pulse amplitude, can result in marked effects on the physical characteristics of resulting tissue damage. Exemplary morphological changes are reported in Parsons et al., Ultrasound in Med. & Biol., Vol. 32, No. 1, pp. 115-129, 2006, which is incorporated herein by reference. Sensitivity of homogenized or disrupted tissue production to acoustic input parameters can provide a means by which to exert control over the degree to which the mechanical effects of localized cavitation are responsible for lesion formation.

II. High Speed Imaging of Bubble Clouds:

In some embodiments of the present teachings, high intensity pulsed ultrasound delivered at low duty cycles can achieve mechanical fractionation of soft tissue. The acoustic pressures effective for tissue fractionation are similar to those found in lithotripter shockwave pulses. This technique can be considered soft tissue lithotripsy, as used herein as "histotripsy". In some embodiments, histotripsy pulses are several acoustic cycles in duration instead of the one cycle pulses used in conventional lithotripsy. At a tissue-fluid interface, histotripsy according to the present teachings produces effective tissue removal resulting in clearly demarcated perforations. In bulk tissue, histotripsy can fractionate tissue structure to subcellular levels, leaving little chance for cell survival. The treated tissue can be fractionated so finely as to appear, for most practical purpose, as a liquid. Therefore, for purposes herein, bulk tissue fractionation using histotripsy can be termed "tissue liquefaction". The boundaries of histotripsy generated lesions in bulk tissue are also sharply demarcated, with only several microns between the liquefied margin and the intact cells. Histotripsy has many potential medical applications where non-invasive tissue fractionation and/or removal are needed, (e.g., removal of solid tumor and cardiac ablation).

The primary mechanism for histotripsy is believed to be acoustic cavitation, which is supported by an enhanced, temporally changing acoustic backscatter observed during the histotripsy process. Without initiation of this temporally changing acoustic backscatter, tissue erosion at a tissue-water interface or tissue liquefaction in bulk tissue was never produced. The acoustic backscatter was thought to be the sound reflection of histotripsy pulses from a dynamically changing bubble cloud. The temporally varying acoustic backscatter does not always occur immediately at the onset of the histotripsy pulses. The time to initiation depends on the pulse parameters, (e.g., it is shorter at higher pulse pressures). After initiation, when the histotripsy pulses are still being delivered, the variable backscatter may stop, which we label as extinction. When extinction occurs, further tissue erosion or tissue liquefaction ceases. The variable backscatter can be reinitiated again without changing the pulse parameters. The extinction and the re-initiation are both stochastic events. As set forth herein, the initiation and extinction are determined by simultaneously imaging the bubble cloud and recording the acoustic backscatter signals.

Cavitating bubble clouds generated by lithotripter shockwave pulses related to bioeffects produced have been studied by many researchers using high speed imaging. To investigate histotripsy generated tissue erosion at a tissue-fluid interface and tissue liquefaction in bulk tissue in accordance with the present teachings, the bubble cloud at a tissue-water interface and inside an optically transparent gelatin phantom which mimics bulk tissue were investigated. The shape and size of the whole bubble cloud was studied as well as the size of individual bubbles inside the cloud.

Histology of histotripsy generated lesions has shown sharply demarcated boundaries from both in vitro and in vivo experiments. The mechanism for the sharp boundaries is thought to relate to the nature of cavitation as a threshold phenomenon. The pressure threshold differences to generate a histotripsy induced cavitating bubble cloud at a tissue-fluid interface in comparison to inside a gelatin phantom were explored.

The extent and efficiency of tissue erosion or tissue liquefaction generated by histotripsy are largely affected by the selection of pulse parameters, including pulse pressure, pulse duration, and PRF. For example, a histotripsy generated tissue erosion area increases with increasing pulse pressure, but the erosion rate along the axial acoustic beam direction (which contributes the most to perforating the tissue) decreases with increasing pressure at high pressure (p-$\geq$9 MPa; $I_{SPPA} \geq 5000$ W/cm²). The effects of pulse pressure on the bubble cloud generated by histotripsy pulses, including the size, shape, and lifetime of the bubble cloud was investigated herein.

A. Methods

1. Sample Preparations

Bubble clouds were generated at a tissue-water interface and inside an optically transparent gelatin phantom. The tissue sample was fresh porcine atrial wall (1-2 mm thick) obtained from a local abattoir and used within 24 h of harvesting. All tissue specimens were preserved in 0.9% saline at 4° C. Tissue was wrapped over ring-shaped tube fitting (2 cm in diameter). Transparent porcine skin based gelatin (Type-A, Sigma-Aldrich, St. Louis, Mo. USA) phantoms were used to mimic bulk tissue. Gelatin powder (7% concentration) was mixed using deionized water and desiccated for 25 minutes to remove any air bubbles 27. Gelatin phantoms were stored at 4° C. overnight and warmed to room temperature before experimentation the following day.

2. Ultrasound Generation and Calibration

The overall experimental setup is shown in a schematic drawing (FIG. 31). Histotripsy pulses were generated by an 18-element piezocomposite spherical shell therapeutic array (Imasonic, S.A., Besançon, France) with a center frequency of 750-kHz and a geometric focal length of 100-mm. The therapy array has an annular configuration with outer and inner diameters of 145 and 68 mm, respectively. All the array elements were excited in phase. The array driving system, maintained under PC control, consists of channel driving circuitry, associated power supplies (Model 6030A, HP, Palo Alto, Calif. USA), and a software platform to synthesize driving patterns. The position of the array was adjusted by a 3-D positioning system (Model A-25, Velmex, Bloomfield, N.Y.) to align the bubble cloud with the camera. The array driving software provided trigger signals to synchronize the bubble image acquisition and acoustic backscatter collection. More details regarding the synchronization are provided in the following sections. The pressure waveform at the focus of the 18-element array in the acoustic field was measured using a fiber-optic probe hydrophone (FOPH) developed in-house for the purpose of recording high-amplitude pressure waveforms. The lateral and axial pressure profiles of the focused beam were measured to be 2.2 mm×12.6 mm in width (full width at half maximum, FWHM) at peak rarefactional pressure of 14 MPa and 1.8 mm×11.9 mm at 19 MPa. The beam width decreased with increasing pressure. The peak rarefactional and compressional pressures and spatial peak pulse average intensities (ISPPA) used in experiments depicted in FIGS. 3($a$)-3($d$) and 4 were measured for free-field conditions and reported in Table 14 (Imaging Frame Rate=10 Hz, Shutter Speed=100-200 ns).

from the transducer focus. For example, for a 14-μs pulse, images were taken at 10 μs after its arrival at the transducer focus. For a 4-μs pulse, images were taken at 3 μs after its arrival at the transducer focus. To study the effects of pulse pressure on bubble cloud dynamics, snapshots of the bubble cloud at different fixed delays (3 μs-1 ms) after the arrival of a histotripsy pulse were taken.

Two types of bubble images were captured. The image of the whole bubble cloud was taken using forward lighting. The bubbles were illuminated by a Xenon arc lamp (Model. 60069 Q Series, Oriel, Stratford, Conn. USA) at a forward 30 degree angle with respect to the camera. A field-of-view (FOV) of 3.6×2.7 cm2 was achieved using a normal lens (AF Nikkor—50 mm f/1.8 D, Nikon, Tokyo, Japan) coupled to a close-up lens (52 mm, 250D, Canon, Tokyo, Japan) and a 2× magnification lens (Canon, Tokyo, Japan). The second image type is a shadowgraph of individual bubbles. To produce a bubble shadowgraph, bubbles were backlit and the shadow of bubbles was captured by the camera. For imaging individual bubbles, we used a compact long distance microscope (QM 100, Questar Corp., New Hope Pa. USA) with diffraction limited 1.1 μm resolution over a 157×209 μm2 FOV at a 14-cm working distance. Both setups are presented in FIG. 31.

The ICCD camera captures images by detecting and recording a count proportional to the photon number at each pixel. Pixels with bubbles have higher photon counts (bright) in forward light imaging and lower photon counts (dark) in shadowgraph. For forward light imaging, the bubble presence was determined when the photon count exceeded a threshold of mean+3 standard deviation (SD) of the photon count at this pixel with no bubbles. For bubble shadowgraphs, the bubble

| Fig # | Imaging | Environment | Pulse Duration | Pulse Parameters | | | | |
|---|---|---|---|---|---|---|---|---|
| | | | | p− (MPa) | p+ (MPa) | $I_{SPPA}$ (W/cm$^2$) | PRF | Total = Pulses |
| 3 | Whole | Tissue-water | 14-μs (10 cycles) | 15.6 | 36.1 | 15 k | 10 Hz | 200 |
| 4 | Bubble | Inside Gel | 14-μs (10 cycles) | >21* | >76* | >32 k* | 10 Hz | 200 |
| 7 | Cloud Imaging | Tissue-water | 14-μs (10 cycles) | 21 >21* | 21 >76* | 32 k >32 k* | Single Pulse | — |
| 8 | | Inside Gel | 14-μs (10 cycles) | >21* | >76* | >32 k* | 10 Hz | 200 |
| 5 | Bubble | Tissue-water | 4-μs (3 cycles) | 15.5 | 28.4 | 12 k | 100 Hz | 2000 |
| 6 | Shadowgraph | Inside Gel | 14-μs (10 cycles) | >21* | >76* | >32 k* | 10 Hz | 200 |

*The peak rarefactional pressure (p−) could not be accurately measured due to instantaneous cavitation. At a lower power input the peak rarefactional and compressional pressures were measured to be 21 MPa and 76 MPa The pressure levels used in other experiments (FIGS. 5-8) could not be calibrated successfully due to the instantaneous cavitation at the hydrophone tip. We were able to measure a peak rarefactional pressure of 21 MPa and a peak compressional pressure of 76 MPa at a lower power level without generation of bubbles during measurement. The acoustic pressure waveform is shown in FIG. 32. See Table 14 for other acoustic parameters and imaging conditions used.

3. High-Speed Imaging

Images of a bubble cloud were captured by a fast gated, 640×480 pixel, 12-bit, 10 frame per second intensified CCD (ICCD) camera (Picostar HR, La Vision, Goettingen, Germany). A shutter speed of 100-200 ns was used. The imaging system can store up to 200 images at one time. To study initiation and extinction, the bubble cloud imaging was synchronized with the acoustic backscatter acquisition. The bubble cloud images were taken when the histotripsy pulse was propagating through the focus. The acoustic backscatter was recorded as the sound reflection of the histotripsy pulses presence was determined when the photon count fell below a threshold of mean−3 SD of the photon count at this pixel with no bubbles. The camera captured the image of the bubble cloud along the axial direction of the ultrasound beam. The axial cross-sectional area of the bubble cloud is estimated by integrating the area of pixels with bubbles using the forward light bubble cloud imaging. The void fraction of the bubble cloud is estimated by calculating the ratio of the area of pixels with bubbles to the whole image area using the bubble shadowgraph.

4. Acoustic Backscatter

To receive the acoustic backscatter of histotripsy pulses, a 5-MHz, 2.5-cm diameter single element focused transducer (Valpey Fisher Corporation, Hopkinton, Mass. USA) with a 10-cm focal length was mounted confocally with the therapy array inside its inner hole. Acoustic backscatter signals were recorded and displayed as range-gated temporal voltage traces by a digital oscilloscope (Model 9384L, LeCroy, Chestnut Ridge, N.Y. USA). The recorded waveforms were then transferred through GPIB and processed by the Matlab program (Mathworks, Natick, Mass. USA).

Normalized acoustic backscatter power moving standard deviation was used to characterize the variability of backscatter. As the acoustic backscatter was due to reflected histotripsy pulses, the backscatter power was first normalized to a reference proportional to the therapy pulse power, which was determined by reflection from a stainless steel reflector. Normalized backscatter power moving standard deviation at a time point i was calculated as the standard deviation of backscatter power at point i, i–1, and i–2 (moving window size=3). The initiation and extinction of the temporally variable acoustic backscatter were detected when the moving standard deviation exceeded and fell below a threshold for five consecutive pulses, respectively. The initiation and extinction thresholds were four times and two times, respectively, the estimated standard deviation of uninitiated backscatter power, which was estimated from acoustic backscatter signals prior to initiation.

B. Results

1. Initiation and Extinction a. Whole Bubble Cloud Imaging

Imaging results show that the initiation and extinction of the variable backscatter corresponded to formation and disappearance of the bubble cloud generated by histotripsy pulses. The bubble clouds consisting of multiple bubbles were generated at a tissue-water interface (FIGS. 33(A)-33(D)) and inside a gelatin phantom (FIGS. 34(A)-34(D)).

The bubble cloud was not always generated at the onset of the histotripsy pulses. The time to initiation depends on the pulse parameters. The formation of the bubble cloud corresponded well to initiation of the temporally changing acoustic backscatter. FIGS. 33(A)-33(D) show an example of bubble cloud formation and initiation of the variable acoustic backscatter signals at a tissue-water interface. The bubble cloud began to form at the 38th pulse after the onset of insonation (detected by estimated bubble cross-sectional area), and the variable acoustic backscatter was also initiated at the 38th pulse (detected by backscatter power moving standard deviation). There were variable backscatter signals between the 4th and 10th pulses, however, no bubbles were observed. This is likely due to the bubble size being below the level of detection by the imaging system.

After initiation, histotripsy pulses may stop generating bubble clouds. The timing of the disappearance of the bubble cloud corresponded to extinction of the variable acoustic backscatter. In FIG. 34, a bubble cloud was generated in a gelatin phantom by histotripsy pulses. Each pulse produced a bubble cloud consisting of multiple bubbles, and the bubble cloud changed from pulse to pulse. After the 87th pulse, the histotripsy pulses stopped forming bubble clouds. One residual bubble remained static from pulse to pulse. Correspondingly, the variable acoustic backscatter extinguished at the 89th pulse. The slight difference in timing could be due to: 1) the residual bubble oscillated between the 87th and 89th pulses, but the oscillation was not large enough to be observed by the imaging; and/or 2) some very small bubbles were produced between the 87th and 89th pulses but were too small to be detected.

A lower acoustic pressure for the tissue-water interface was used compared to inside the gel, because the pressure threshold to initiate a bubble cloud appears to be lower at a tissue-water interface (detailed in Results section D).

b. Shadowgraph of Individual Bubbles

Shadowgraphs of individual bubbles within the bubble cloud were captured. The bubble shadowgraphs also demonstrate that the formation and disappearance of the individual bubbles corresponded to the initiation and extinction of the variable acoustic backscatter, respectively. For example, the initiation of the variable acoustic backscatter signal and the appearance of the bubbles were both observed at the 981 st pulse at a tissue water interface (FIGS. 35(A)-35(D)). In FIGS. 36(A)-36(D), the bubbles were first generated in the gelatin phantom by histotripsy pulses and variable backscatter was detected. No bubbles were shown in the shadowgraph after the 30th pulse, and, the extinction of the variable backscatter occurred at the 54th pulse. The difference between the two in timing is most likely because bubbles were generated outside the imaging frame between the 30th and 54th pulses. The shadowgraph imaged bubbles within a portion and not the whole bubble cloud.

2. Size and Shape of the Bubble Cloud

The bubble cloud generated by histotripsy pulses appeared to consist of multiple bubbles both inside a gelatin phantom and at a tissue-water interface. The size and shape of the bubble cloud changed from pulse to pulse. The bubble cloud generated inside the gel was usually cigar-shaped (FIG. 34). In FIG. 34, the bubble cloud produced in the gel was 1.2-3 mm (diameter along the lateral acoustic beam)×2-7.5 mm (diameter along the axial acoustic beam). The bubble cloud generated at a tissue-water interface in FIGS. 33(A)-33(D) did not have a well-defined shape and changed significantly from pulse-to-pulse. In comparison to the bubble cloud generated in the gel, the size of the bubble cloud was also small, with both lateral and axial diameter of the bubble cloud shorter than 2 mm. The small size and irregular shape of the bubble cloud in FIGS. 33(A)-33(D) may be due to the lower pulse pressure applied. At higher pulse pressures, the bubble cloud formed at a tissue-water interface was larger and mostly cone-shaped (FIG. 37). The base of the cone was attached to the tissue surface and the tip was directed away from the tissue. Interestingly, the bubble cloud was divided into sections along the axial direction of ultrasound beam (FIG. 37). Each section was separated half of the wavelength at 750 kHz (1 mm), which suggests that the section formation was caused by a standing wave at the tissue boundary. The bubble cloud changed dynamically with time both during and after the histotripsy pulse (FIG. 37). In addition, size and shape of the bubble cloud were affected by the pulse parameters. The effects of peak rarefactional pressure on the bubble cloud are reported in section E of the Results.

3. Size of Individual Bubbles

With the assistance of a long distance microscope, it was possible to recognize individual bubbles above 4 µm in diameter. Bubbles with diameters between 4-50 µm were generated by histotripsy pulses inside a gelatin phantom and at a tissue-water interface (FIGS. 35(A)-35(D) and 36). Inside the gel, the majority of the bubbles were between 8 and 20 µm (FIGS. 36(A)-36(D)). Bubbles smaller than 4 µm might exist but could not be clearly identified due to the limited spatial resolution (1.1-µm). In some images, multiple bubbles appeared to be connected together. These bubble aggregations may be caused by the coalescing, and/or overlapping of bubbles along the line of the light beam and was seen quite often at a tissue-water interface (FIGS. 35(A)-35(D)). Multiple bubbles can form aggregations of 100 µm in diameter or even larger. The bubble shadowgraphs were taken when the histotripsy pulse was propagating through the transducer focus. Bubbles are expected to continue growing after the histotripsy pulse.

4. Differential Cavitation Pressure Threshold

When focusing histotripsy pulses within a 2.5 cm-thick gelatin phantom, two bubble clouds were generated along the ultrasound beam path. One was generated at the transducer focus inside the gel, and the other was generated ~1 cm away from the transducer focus at the gel-water interface. However, no bubbles were created between the two, where the pressure was higher than at the gel-water interface (FIG. 38). This result suggests that the pulse pressure required to generate a bubble cloud was lower at a gelwater interface than inside the gel. It is possible that standing waves can form at the front surface of gel (the surface closer to the transducer) due to the sound reflection, resulting in increased pulse pressure (FIG. 38a). However, bubble clouds were also generated at the back surface of gel (the surface away from the transducer) where standing waves are unlikely to be formed (FIG. 38b). This second observation suggests that standing waves are probably not responsible for bubble generation at gel-water interfaces. In addition, the bubble cloud generated at the gel-water interface typically was larger than that created inside the gel at the transducer focus (FIG. 38), even though the pressure was lower for the former.

5. Effects of Peak Rarefactional Pressure on Bubble Clouds

FIG. 37 shows bubble cloud images generated by a 10-cycle (14-μs) histotripsy pulse at peak rarefactional pressures of 21 MPa and >21 MPa at a tissue-water interface. The pressure levels for the latter could not be measured successfully due to instantaneous cavitation at the hydrophone tip. Images were taken at different time delays (3 μs-1 ms) after the arrival of a histotripsy pulse. At both pressures, the cloud persisted long after the pulse, and the bubble cloud lasted longer at higher peak rarefactional pressure. Initial bubble cloud formation was observed at 3 μs. It increased in size with time during the pulse until 10 μs. The size of the bubble cloud remained similar at 10 μs, 30 μs, and 100 μs. At 300 μs, a bubble cloud was not seen at the peak rarefactional pressure of 21 MPa, but a small cloud was observed at the higher pressure. At 1 ms, no bubble clouds were observed at either pressures. Small residual bubbles may still exist but were not seeing due to camera's limited spatial resolution.

The bubble cloud was also larger at higher peak rarefactional pressure. The bubble clouds appeared to be cone-shaped growing outward from the tissue surface. At the peak rarefactional pressure of 21 MPa, the cloud was ~3.3 mm long and ~1.9 mm wide at the base of the cone at its peak size recorded (at 10 μs). At the peak rarefactional pressure >21 MPa, the cloud reached its maximum size (at 30 μs) of ~4.8 mm long and ~4.3 mm wide at the base of the cone.

C. Discussion

Using high speed imaging, it was observed that a bubble cloud was generated by histotripsy pulses at a tissue-water interface and inside a gel phantom which was used to mimic bulk tissue. The formation and disappearance of the bubble cloud corresponded to the initiation and extinction of an enhanced and temporally changing acoustic backscatter, respectively. This result suggests that the variable acoustic backscatter was most likely the sound reflection of histotripsy pulses from the dynamically changing bubble cloud. As our previous studies have demonstrated, without the initiation of temporally-spatially varying acoustic backscatter, tissue erosion at a tissue-water interface or tissue liquefaction inside bulk tissue were never produced. The correspondence between the variable acoustic backscatter and the bubble clouds provides further evidence that the cavitating bubble cloud plays an essential role in the histotripsy process.

It was found that the pulse pressure required to generate a bubble cloud is lower at a gel-water interface than inside a gel, which suggests a lower cavitation threshold at a tissue-fluid interface than inside bulk tissue. This may explain the sharply demarcated boundaries (several μm) of histotripsy generated tissue erosion at a tissue-fluid interface and tissue liquefaction in bulk tissue observed both in vitro and in vivo. The sharp boundaries are probably due to a very large spatial threshold gradient. The boundary of tissue erosion exists at the location where the pulse pressure is just below the cavitation threshold at a tissue-fluid interface. As the pressure threshold within tissue is much higher, no damage is expected to be produced in surrounding tissue. Tissue liquefaction in bulk tissue can first start where the pressure is higher than the cavitation threshold. When part of the tissue is liquefied, it forms a smooth liquid resulting in a tissue-fluid interface. From this point in the process, tissue liquefaction becomes internal tissue erosion. The liquefaction can continue to expand to where the pulse pressure is just below the cavitation threshold at a tissue-fluid interface, resulting in a sharp boundary. Because the pressure threshold in bulk tissue is much higher than at a tissue-fluid interface, no damage would be done in the surrounding tissue. Further studies with better control of cavitation nuclei in gel and water would be needed to verify this mechanism.

The extent and efficiency of tissue erosion or tissue liquefaction generated by histotripsy depend on the selection of pulse parameters including pulse pressure, pulse duration, and PRF. It is believed this dependency is due to the impact of pulse parameters on bubble cloud dynamics. Based on herein, the effects of peak rarefactional pressure on the bubble cloud were studied, which indicated that the bubble cloud is larger and lasts longer at higher peak rarefactional pressure. This result is consistent with our previous finding that the tissue erosion area is larger at higher pressure. Previous results also demonstrate a decreasing axial erosion rate at higher pressure above a certain level (p-_9 MPa or ISPPA_5000 W/cm2). Along the axial acoustic beam direction, the center of the bubble cloud is thicker at higher pressure, with more and/or larger bubbles. These bubbles may hinder the ultrasound energy propagation to the tissue surface and slow down the erosion rate in the axial direction. Other pulse parameters (e.g., pulse duration and PRF) also have effects on the extent and efficiency of tissue erosion and liquefaction. For example, more energy efficient erosion can be achieved with shorter pulses and at certain PRF's. Parsons et al. found that tissue liquefaction can be facilitated by interleaving high-amplitude histotripsy pulses with low-amplitude pulses, while high-amplitude histotripsy pulses delivered at doubled PRF only achieve mostly thermal mediated lesions. These results raise interesting and critical questions of how pulse parameters change the bubble dynamics to cause different bioeffects and how one might increase histotripsy efficiency. Understanding initiation and extinction of bubble clouds, and subsequent bubble cloud dynamics, as a function of easily changed pulse parameters can provide a rational basis for optimization of the histotripsy process. With proper feedback, pulse to pulse optimization through changes in pulse parameters will become possible.

According to the present teachings, the bubble cloud at different delay times was imaged after the arrival of the histotripsy pulse. Initial observations show that the bubble cloud seems to behave as one entity and changes together during and after the pulse. A bubble cloud generated by a several psec long histotripsy pulse can last for several hundred psec. In fact, our previous optical monitoring results suggest that the residual bubbles from cloud collapse can remain for several msec. The temporal dynamics of the bubble cloud and the individual bubbles during and between the pulses are critical to understand the underlying mechanisms of histotripsy. For example, is the majority of tissue erosion and tissue liquefaction done during the histotripsy pulse or after, and how? The bubble cloud can be quite large yet the damage boundary can be remarkably small (several microns), why? Apparently, it is individual bubbles that produce the damage, not the cloud, but how? How do the bubble remnants from the previous pulse interact with the next pulse? Our group is currently studying the temporal evolution of the bubble cloud in the hope of further clarifying the interesting underlying physical mechanisms of the histotripsy process.

D. Summary of High Speed Imaging

High-speed imaging has shown bubble clouds are generated by histotripsy pulses at a tissue-water interface and inside a gelatin phantom which was used to mimic bulk tissue. A correspondence was observed between the formation of a bubble cloud and the initiation of a temporally changing acoustic backscatter, which is essential for the production of tissue erosion and tissue liquefaction. The pressure threshold to generate a bubble cloud at a gel-water interface is lower than inside the gel, suggesting the pressure threshold to initiate a bubble cloud is lower at a tissue-fluid interface than inside bulk tissue. This pressure threshold difference is contributing to the sharply demarcated boundaries of histotripsy generated tissue erosion at a tissue-water interface and tissue liquefaction in bulk tissue. Further, the bubble cloud is larger and lasts longer at higher peak rarefactional pressure, which may explain our previous in vitro results that the erosion area is larger and the axial erosion rate is slower at high pulse pressure (p-_9 MPa). Still additional detail related hereto is set forth below.

III. Therapeutic Applications:

In some embodiments, the pulsed cavitational ultrasound methods of the present teachings permit various therapeutic procedures, including tissue erosion via controlled mechanical subdivision of soft tissue, bulk tissue fractionization, or drug delivery and activation, to be accomplished either wholly from means external to the body, or with minimal dependence on procedures no more invasive than current endoscopic techniques. Being noninvasive, the cost advantages, both in hospital stay and in surgical preparation time, are readily apparent. In addition, the reduction or absence of cosmetic disfigurement and risk of infection are both significant advantages. While this noninvasive property is shared with other ultrasound based delivery methods, cavitationally based surgery according to the present teachings has several potential advantages over current approaches.

In some embodiments, therapies based on the present teachings can include following features: ability to use a low ultrasound frequency, which will not heat intervening tissue; ability to use a frequency low enough to propagate through some bone interfaces such a ribs; ability to use a frequency low enough to make phased array element sizes larger thus significantly reducing array and driving system costs; additional localization afforded by a two-step process each of which involves focusing and localization, i.e., generation of a population of localized cavitation nuclei tuned to a given frequency band provides one step in localization, and a focused beam at the optimum cavitation frequency (lowest cavitation threshold because of the preselected nuclei) affords additional localization; possibility of activating drugs (with cavitation) or delivering drugs (with the cavitation nuclei), or a combination of both phenomena, is possible in addition to the surgical lesion obtained, e.g., combination spatially localized surgery chemotherapy for cancer treatment, including drugs for reduction of bleeding and/or for treatment of blood clots are also possible; and, the coupling of targeting of cavitation nuclei with molecular methods for cavitation nuclei, e.g., conjugation of cavitation nuclei, or precursors (prior to activation) of cavitation nuclei, with monoclonal antibodies or other molecules which bind to cancer cells or otherwise accumulate or are targeted to tumors or other tissues or organs of interest for either diagnostic or therapeutic outcomes.

In addition to various tissue ablation applications, such as tumor disruption, the methods disclosed herein can be used in applications where tissue is subdivided (i.e., homogenized, liquefied, or disrupted) and subsequently aspirated to remove the subdivided tissue. For example, ablation of tumors or diseased tissues can be followed by aspiration using a needle to remove the liquefied tissue.

In some embodiments, a needle can be used to extract the subdivided or liquefied tissue. In some procedures (e.g., body shaping and/or fat reduction), this may be quite important. Furthermore, in ablation of large tumors (e.g., uterine fibroids), removing the treated liquefied volume via aspiration or suction may avoid possible toxic effects of large liquefied tissue volumes which might not be easily absorbed into the body.

In some embodiments, the void created by the former tissue can be replaced with another medium, for example, and either replaced continuously by perfusion or by sequential aspiration of liquefied tissue followed by injection of the replacement medium. Replacement medium can further include various physiologically compatible vehicles, which in some embodiments can further contain therapeutic agents. For example, a needle can be used to inject replacement medium in order to fill up the void created following removal of the liquefied tissue. For example, such embodiments can be used to provide drug delivery to affect the margins of a treated zone of an ablated tumor in cancer treatment.

Applications of the present disclosure can also provide utility in the art of cosmetic body shaping, and in procedures where a needle or other device is inserted into the treated volume to sample or otherwise test the tissue. In some embodiments, the tissue could be tested for viable cells, for example as in cancer biopsy, or the mechanical properties of the treated tissue can be tested.

Other various embodiments of the present disclosure can include aspects of drug delivery and drug activation using pulsed cavitational ultrasound therapy. For example, methods of the present disclosure can be used to temporally disrupt membranes to permit therapeutic agents to cross one or more membranes and reach their targets. Other embodiments can include using the histotripsy process to activate ultrasonically sensitive compounds that either become active therapeutic compounds themselves, or release active therapeutic compounds at the therapy site.

Using the histotripsy process to break drug resistant barriers (cell membranes, skin, cardio-vascular and blood-brain barriers, intestine, uterine lining, bladder lining, disease related granulomas, etc.), the feedback and monitoring processes of the present disclosure allow control of the tissue disruption process, enabling temporal disruption of tissues with minimal or no permanent tissue damage. These methods are possible due to the feedback and monitoring methods described herein. Consequently, the methods of the present disclosure can be used to deliver or enhance delivery or associated delivery of therapeutic agents, including pharmaceuticals (drugs), nano-particles, nucleic acids including DNA, RNA, and recombinant constructs, or other non-drug particles of molecules. The drug delivery process can use the feedback processes described herein in order to monitor the progress of the histotripsy process in real time or in stages.

In some embodiments, the present teachings can further include the use of ultrasonically-sensitive materials including ultrasonically-sensitive compounds and polymers. For example, methods can include an ultrasonically-sensitive compound and/or polymer, or other molecular construct, that is sensitive to mechanical rectification, or other aspects of exposure to high intensity ultrasound, i.e., the compound would change its shape or conformation, or chemical reactivity, in response to ultrasound. These ultrasonically-sensitive compounds or polymers can be used in various applications and several types of ultrasonically-sensitive compounds or polymers can be employed.

Ultrasonically-sensitive materials include compounds and polymers of piezoelectric compounds, electrically-sensitive compounds, and piezoelectric compounds that are coupled to electrically-sensitive compounds. Exemplary piezoelectric materials include polyvinylidene fluoride (PVDF) and lead zirconate titanate (PZT). Ultrasonically-sensitive compounds and polymers also include materials known as switchable materials, where for example ultrasonic and/or electrical stimulation can change the viscosity, conformation, and/or hydrophobic or hydrophilic character of the compounds and polymers. In some embodiments, switchable materials include ferroelectrics, electrochromics, and materials used for optical switching.

For example, a piezoelectric material coupled with an electrically-sensitive material can be a switchable material. Furthermore, piezoelectric materials can be co-polymerized with electrically sensitive materials to form ultrasonically-sensitive polymers.

Various embodiments of ultrasonically-sensitive materials further include pharmaceutical agents complexed with the ultrasonically-sensitive materials either covalently or through non-covalent interactions. Pharmaceutical agents can include small molecule organic compounds and larger molecules or polymers, such as proteins, multi-subunit proteins, and nucleic acids. In particular, some embodiments of the present disclosure include delivery of large molecules such as protein, nucleic acids, such as DNA (including recombinant DNA) and RNA, or other polymers using the delivery and fluid pump applications described herein to transport the molecules across barriers and membranes. Various embodiments of ultrasonically-sensitive materials can also include nanoparticles formed of ultrasonically-sensitive polymers, where the nanoparticles can contain pharmaceutical agents. Embodiments further include ultrasonically-sensitive materials that are biocompatible scaffold materials. For example, scaffold materials can be used to replace tissue and/or support local tissue structure or support cells. Ultrasonically-sensitive materials can be switchable to release a pharmaceutical agent, for example.

In some embodiments, molecules sensitive to asymmetrical waveforms prevalent due to nonlinear propagation of ultrasonic waveforms can be used. With such waveforms, the peak positive pressure can be an order of magnitude, or more, greater than the peak negative pressure. A compressible molecule, or part of a molecule, can act as an effecter by changing its shape considerably during ultrasound exposure thus triggering a specific event or process, like drug release or formation of a contrast microbubble for imaging or for enhancing cavitational ultrasound therapy. In addition, such molecules can enhance chemical reactivity, thereby having a direct pharmacological effect, or can enhance the pharmacological effect of other drugs or protodrugs. Likewise, some embodiments of the present teachings can include use of molecules that are sensitive to peak negative or positive pressures and/or ultrasonic intensities which would have similar effects as those just described.

Various embodiments also include use of molecules or polymers or other molecular constructs that are sensitive to free radical concentration. For example, ultrasound cavitation can generate free radicals that could be used as a trigger to cause the molecules to become effecters. Moreover, since free radicals are part of the natural inflammation process, such free radical sensitive polymers can be useful effecters even without an ultrasound trigger, thus allowing more pharmacological control of the inflammation process. These free radical detecting molecules can also be used for cavitation detection in vivo as inflammation detectors.

Such molecules can also be designed to generate or process dissolved gasses so as to form free gas bubbles in response to many different triggering events or sensing environments. For example, when bound to a tumor specific antigen the molecule can change functionality and produce a gas bubble. This gas bubble would then be useful as a contrast agent for diagnostic detection or as a nucleus for therapeutic ultrasound. High intensity ultrasound could then be used to destroy any cell or tissue binding that molecule.

In some embodiments, employing ultrasonically-sensitive molecules can further include the following applications and processes. First, cardiac infarction or stroke produces ischemic tissue and/or inflammation which in turn damages affected tissues by free radical formation. A free radical sensitive molecule can release drugs comprising contrast agents thereby allowing quicker diagnosis and/or treatment. Second, a molecule reacting to some aspect of an ultrasonic exposure, such as pressure, intensity, cavitation asymmetric waveforms due to nonlinear propagation, cavitation, and/or free radical formation due to cavitation, can be an ideal candidate as a drug carrier, contrast agent delivery vehicle, nuclei for therapeutic cavitation, etc. Third, ultrasonically-sensitive molecules that change in response to ultrasound exposure, by any of the mechanisms mentioned herein, can have biological effectiveness by many different mechanisms, including: switchable enzymatic activity; switchable water affinity (change from hydrophobic to hydrophilic, for example); switchable buffer modulating local pH; switchable chemical reactivity allowing remote ultrasound control of an in vivo chemical reaction, perhaps producing a drug in situ or modulating drug activity; switchable conformations of a smart molecule allowing the covering or uncovering (presentation) of an active site which could bind with any designed binding specificity, e.g., a drug which was inactive (inert) until triggered locally by ultrasound. And fourth, ultrasonically-sensitive molecules that are switchable free radical scavengers can be activated by ultrasound for tissue protection following a stroke or cardiac infarction.

Another type of drug delivery therapy can involve free radical generators and scavengers as cavitation modulators. Ultrasonically induced spatial gradients in free radical concentrations can be used to protect some regions or anatomical features from therapeutic damage while enhancing the susceptibility of (or predisposing) other regions to therapeutic damage. This notion results from observations that local free radical concentrations can modulate cavitation thresholds. In such applications, modulating free radical concentrations, for example, by a high frequency high spatial resolution transducer, allows therapeutic spatial specificity (or selectivity) with a lower frequency low spatial resolution transducer which can effectively cavitate predisposed regions and not other protected regions.

Other ultrasonically-sensitive molecules could work with changes in localized concentration of many other reagents, molecules, drugs, etc. to protect some regions and to predispose others. Exemplary applications can include modulating cavitation nuclei either naturally or by some ultrasonically-sensitive molecules designed to act as cavitation nuclei (or a processor of cavitation nuclei) and which are controlled in their activity by ultrasonically induced changes in free radical concentrations, pH, etc.

In some embodiments, the present teachings can include using ultrasound as a fluid pump. In other embodiments described herein, the therapeutic ultrasound acts on agents (ultrasonically-sensitive molecules, etc.) introduced into the body. In these embodiments, the ultrasound can act directly on cells, tissues, or other living matter. In particular, asymmetrical ultrasound pulses arriving in the therapy volume can have a fluid flow rectification effect. This can be effective in moving fluids, and in particular, fluids containing drugs and/or drug carriers, or other useful substances or particles, across natural barriers such as the cell membranes, endothelial barriers, skin barriers, and other membrane-like living constructs, e.g., the blood-brain barrier, which naturally compartmentalize one tissue or organ volume from another. These pumping applications can occur due to nonlinear effects related to the ultrasound waveform, or due to the large asymmetrical waveforms pressures resulting from nonlinear propagation. These applications can also include situations where transitory damage to these barriers due to cavitation and other ultrasound physical effects, such as sonoporation, temporarily open barriers while at the same time forcing (pumping) fluids across these barriers. When the transitory damage self-repairs, a net fluid (mass) transport has taken place with useful consequences.

It should be noted that other mechanisms of fluid transport are possible. In some embodiments, bubbles collapsing in response to therapy pulses can form collapse jets which interact vigorously with the surrounding environment and tissue. At a barrier, these collapse jets can physically move fluids across the barrier, effectively creating an ultrasound-activated pump.

Exemplary applications of these embodiments include the following. First, excess fluid on one side of a barrier could damage or destroy a cell or sub-organ system due to excess pressure, or excess volume, or other physical effect due to this fluid transfer. Thus, this mechanism can be employed in pulsed cavitational ultrasound therapy for destroying or ablating tissue. Second, the forcing of fluids across living system barriers can be used as an extremely effective drug delivery mechanism, or mechanism for delivering any water soluble or suspended substance or particle, across natural barriers, or even through tissue where limited diffusion or flow itself is a barrier. Thus, the forced flow (ultrasonic pumping) in these applications would be an effective mechanism to move fluids within the body in confined volumes using focused ultrasound. These methods can be accomplished non-invasively, minimally invasively, or intra-operatively, and can be done under image guidance using the feedback and monitoring methods described herein.

The following non-limiting examples illustrate the compositions, methods, and applications of the present teachings.

Example 1

Feedback & Monitoring of Ultrasound Tissue Erosion Using Acoustic Backscatter

Tissue Samples In vitro experiments were conducted on 33 porcine atrial wall samples (i.e., the target tissue 108). Porcine atrial wall was used because it is similar to the neonatal atrial septum and has a larger size. Fresh samples were obtained from a local slaughter house and used within 72 hours of harvesting.

Ultrasound Transducer and Calibration: The experimental apparatus 100 for ultrasound exposure and acoustic backscatter acquisition is given in FIG. 1. The 788-kHz focused single element therapy transducer 102 (f number=1, Etalon Inc., Lebanon Ind. USA) from was employed to create erosion. The 5-MHz monitoring transducer 104 is mounted in the center inner hole of the 788-kHz therapy transducer 102.

Acoustic Backscatter Acquisition: Acoustic backscatter from the therapy pulse at 788 kHz were received by a focused single element monitoring transducer 104 with 5-MHz center frequency (Valpey Fisher Corporation, Hopkinton, Mass. USA) mounted coaxially with the 788-kHz therapy transducer 102. The 5-MHz monitoring transducer 104 has a 2.5-cm aperture and a 10-cm focal length. The 5-MHz passive monitoring transducer 104 was used because (1) its focal length is 10 cm and it is smaller (2.54 cm diameter) than the inner center hole (3.7 cm diameter) of the therapy transducer 102 so that it can be conveniently aligned coaxially with the therapy transducer 102 by being fixed in the center hole; and (2) it has a wide bandwidth (−6 dB bandwidth of 4 MHz) that it can detect the fundamental and higher harmonic frequency components of the therapy pulses.

Acoustic backscatter waveforms were recorded using a digital oscilloscope 120 (Model 9354™, LeCroy, Chestnut Ridge, N.Y. USA). The oscilloscope trigger was synchronized with the therapy pulses, and the trigger time delay was adjusted such that a 20 µs-long backscattering signal was received from the erosion zone. A total of 2000 20 µs-long waveforms were collected using the sequence mode and single trigger of the scope setting. The interval between consecutive waveform recordings was set such that the whole initiation process could be recorded within the time span of multiplication of the interval between consecutive recordings and 2000 (number of backscatter waveform collected). For example, with therapy pulses of 3 cycles at a PRF of 20 kHz, 2000 waveforms were recorded with a 200-µs interval between waveforms. The detected signals were digitized by the oscilloscope 120 at a resolution of 40-100 ns. The recorded waveforms were then transferred to a computer 112 through GPIB and processed by a Matlab program (Mathworks, Natick, Mass. USA) to detect initiation of the variable backscatter based on criteria to be defined later. The same procedures were repeated to detect extinction of the variable backscatter, but the interval between consecutive recordings was adjusted to 240 ms so that backscatter during the whole 8-min ultrasound treatment could be recorded.

Ultrasound pulses were delivered by the 788 kHz therapy transducer 102. Porcine atrial wall sample (the target tissue 108) was positioned at the transducer 102 focus. Acoustic backscatter from the therapy pulse at 788 kHz was received by a 5 MHz monitoring transducer 104.

Statistical Approach to Detect Initiation and Extinction of the Variable Acoustic Backscatter: Based on experimental observations, the onset of initiation presumably associated with the onset of cavitation is accompanied by alterations in the acoustic backscatter signal. One such change is a sudden increase in the backscatter amplitude at initiation. Further, this amplitude increase is followed by a chaotic fluctuation in the backscatter signal. Together, these two changes indicate an overall change in the variability of the signal as the transition is made between the uninitiated and initiated states of cavitation. A statistical method was developed for the detection of initiation and extinction of the temporally fluctuating backscatter pattern based on this change in variability.

To identify points of initiation and extinction based on variability in the backscatter signal, a technique from the area of statistical quality control of industrial processes was applied, the Shewhart Chart (G. B. Wetheril and D. W. Brown, Statistical Process Control Theory and practice: Chapman and Hall, 1991). Depending on the data, different Shewhart charts are used to identify changes in a time series process. For this particular situation, the s-chart was used, where the sample standard deviation (SD) of the backscatter power at point i in the time series is used as the measure of variability. However, in the present data, a single measurement of the backscatter power was made at each time point in a given experiment. For such "one-at-a-time" data, the standard deviation at a single point cannot be directly estimated, and a moving standard deviation approach is often employed.

In the present situation, a moving window size of three was used to estimate the standard deviation at each point i in the time series, SDi. For example, the estimate of SDi was calculated based on the backscatter power at point i and the two points preceding it, i−1 and i−2. We define initiation to have occurred when five consecutive SDi's exceed a threshold of four times the estimated standard deviation of the uninitiated backscatter power. We define extinction to have occurred when five consecutive SDi's fall below a threshold of two times the standard deviation of the uninitiated backscatter power. Determination of the moving window size and the initiation threshold coefficient is detailed in Example 2 as described herein.

The acoustic backscatter signal was the output voltage of the 5-MHz monitoring transducer. Backscatter power was calculated by integrating the square of this voltage over each line in fast time.

$$\text{Backscatter Power} = \frac{1}{N}\sum_{i=1}^{N} V^5(i), \quad (1)$$

where N is the number of points in one line of backscatter signal, and V(i) is the voltage value of the $i^{th}$ point within this line of backscatter signal.

The statistical procedure for identifying initiation and extinction consists of the following steps:

Step 1: the first n (10≦n≦100) frames of backscatter prior to any high degree of variation in the signal potentially indicating initiation were collected. Then SD of the backscatter power while uninitiated could be estimated based on the first uninitiated n points using the Shewhart charts (equation 2).

$$\text{Estimated standard deviation} = \frac{1}{1.102}\sum_{i=1}^{x=2}\text{Range}(x_i x_{i-1}, x_{i-2}), \quad (2)$$

$$\text{Range}(x_i, x_{i-1}, x_{i-2}) = \text{maximum}(x_i, x_{i-1} x_{i-2}) - \text{minimum}(x_i, x_{i-1}, x_{i-2}), \quad (3)$$

The purpose of choosing a moving range of 3 points to estimate the SD of backscatter power while uninitiated is to be consistent with the window size used to calculate the moving SD.

Step 2: the moving SD of backscatter power is calculated. Then initiation and extinction can be detected based on the two previously described criteria. Both criteria are programmed in Matlab (Mathworks, Natick, Mass. USA), so initiation and extinction can be detected automatically.

Figure 2:
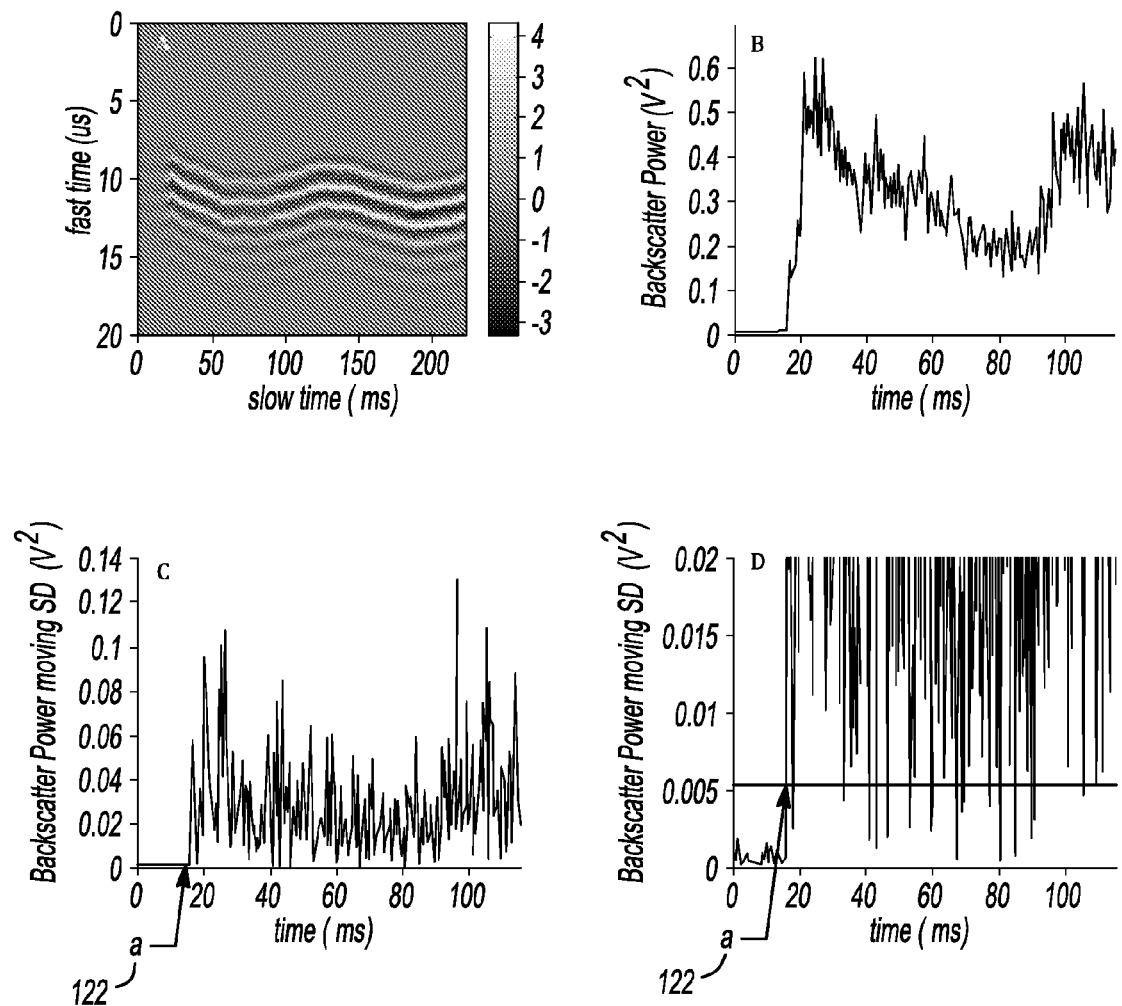
Figure 4:
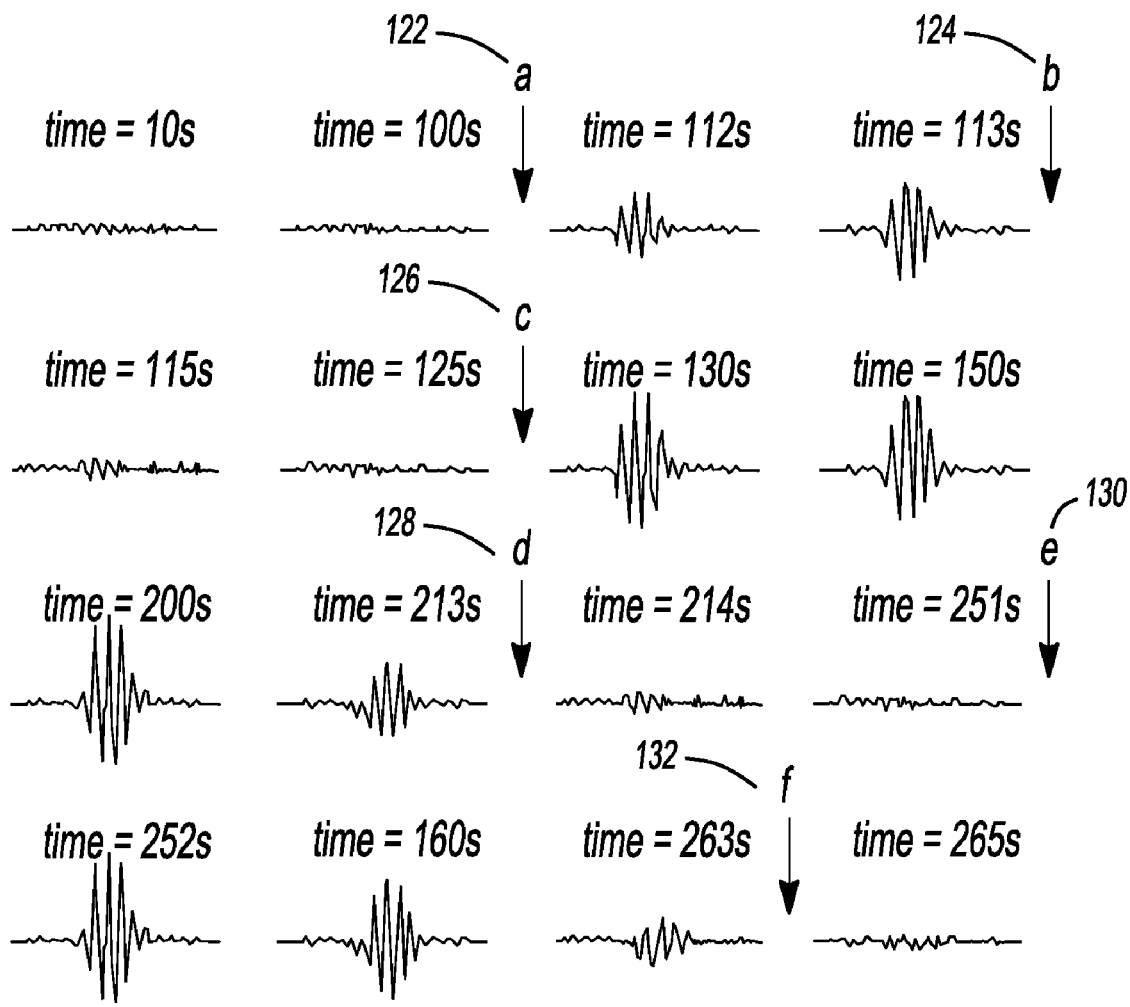
Figure 5:
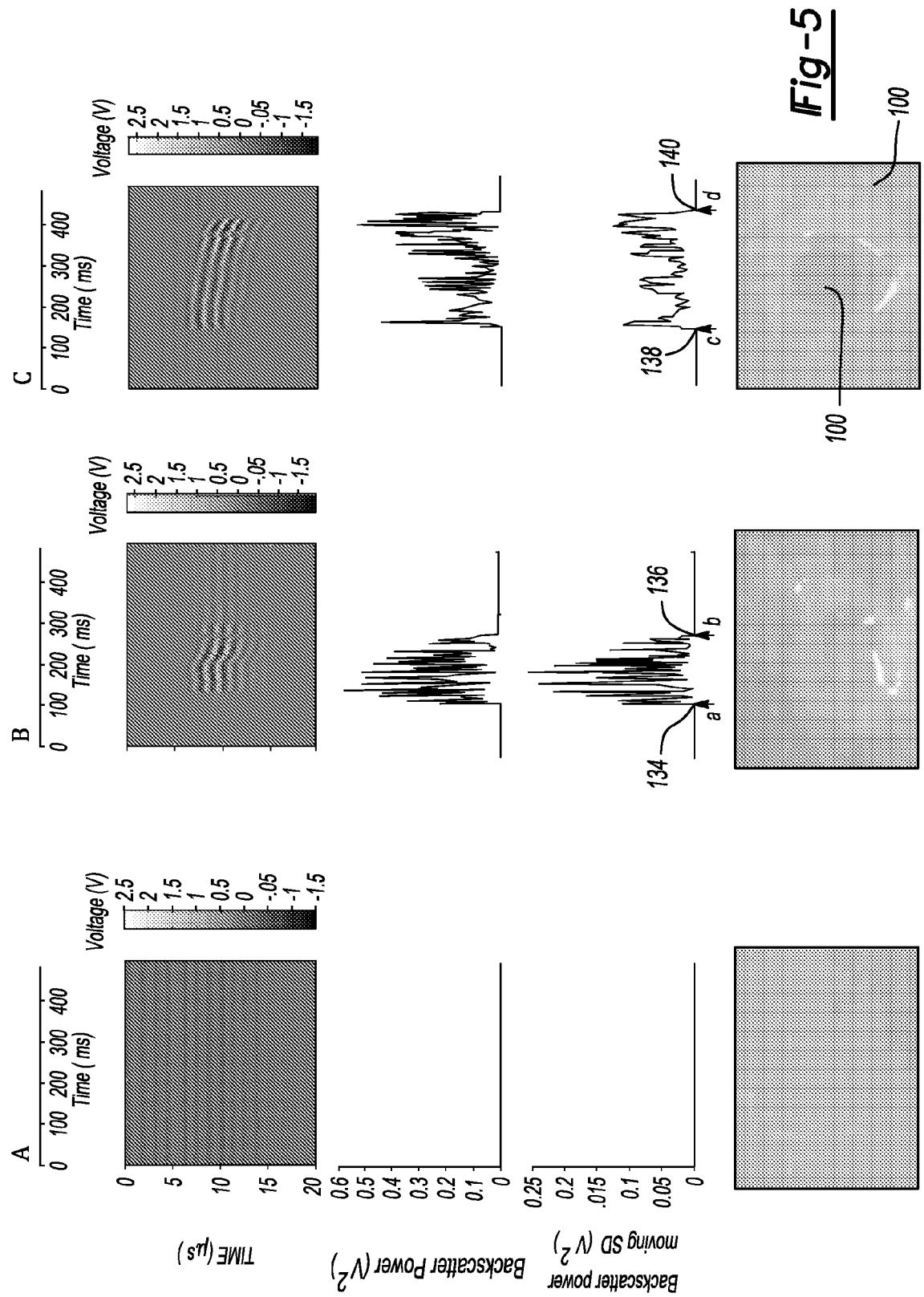

FIG. 2 demonstrates the process of detecting initiation of the variable backscatter. Detection of extinction of the variable backscatter is demonstrated in FIG. 3. FIG. 4 shows the actual waveforms of the acoustic backscatter before and after initiation and extinction. FIG. 5 depicts the initiation and extinction phenomena and corresponding tissue effects generated. It should be noted that when tissue is perforated, the backscatter variability is greatly reduced and is detected as an extinction based on the criteria presented herein.

FIG. 2 demonstrates the process to detect initiation of the variable acoustic backscatter. Panel A, B, C and D show the steps of initiation detection in sequence. Panel A shows the acoustic backscatter in fast time and slow time display. Each vertical line shows an A-line backscatter recorded in a range-gated 20-μs window where output voltage of the 5-MHz monitoring transducer 104 is encoded in gray scale. The x-axis is treatment time. The sampling frequency in show time is 8.33 kHz. The wavy structure of the backscatter along slow time is likely due to the moving bubbles in the erosion zone. Panel B shows the backscatter power versus time. Panel C shows the moving SD of backscatter power versus time. Panel D is an expanded view of panel C. The line is the initiation threshold, set by 4 times the SD estimation of the uninitiated backscatter power. In Panel C and D, the variable backscatter was initiated at "a" 122 detected by the criteria defined for initiation, Ultrasound pulses with a pulse duration (PD) of 3 cycles, a pulse PRF of 20 kHz, an $I_{SPPA}$ of 5000 W/cm², and gas concentration of 46% were applied.

Figure 3:
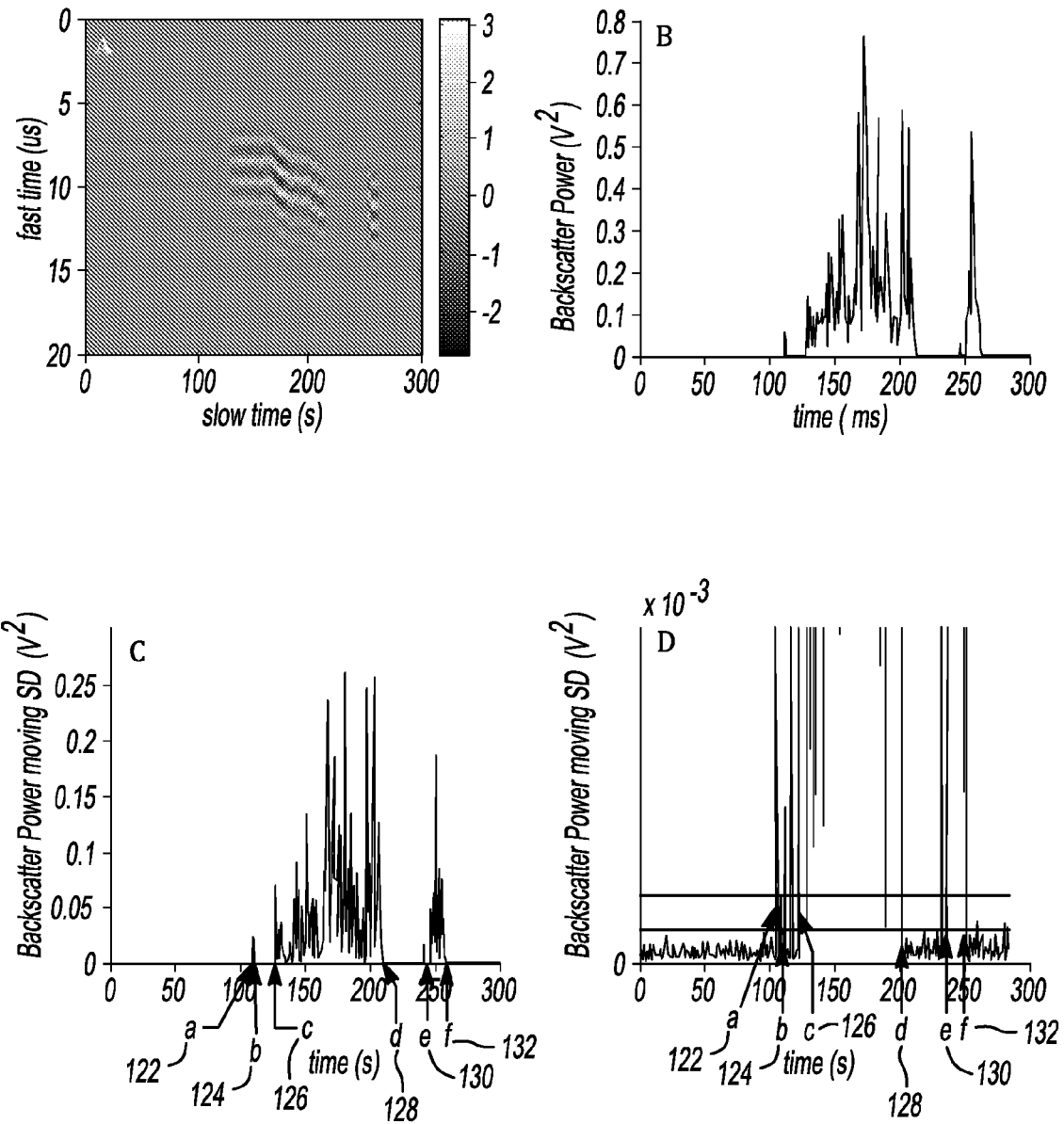

FIG. 3 demonstrates the process to detect initiation and extinction of the variable acoustic backscatter. Panel A, B, C and D show the steps of initiation and extinction detection in sequence. Panel A shows the acoustic backscatter in fast time and slow time display. The sampling frequency in show time is 6.67 Hz. The shift of backscatter along slow time is mostly due to the movement of cavitating bubbles away from the transducer as a result of the progression of tissue erosion. As erosion progresses, the tissue front surface, which holds the position of cavitating bubbles, shifts away from the transducer 102. Panel B shows the backscatter power versus time. Panel C shows the moving SD of backscatter power versus time. Panel D is an expanded view of panel C. The line above is the initiation threshold, set by 4 times SD estimation of the uninitiated backscatter power. And the line below is the extinction threshold, set by 2 times SD estimation of the uninitiated backscatter power. In Panel C and D, detected by the criteria defined for initiation and extinction, the variable backscatter was initiated at "a" 122, extinguished at "b" 124, spontaneously reinitiated at "c" 126, extinguished again at "d" 128, reinitiated again at "e" 130, and tissue was finally perforated at "f" 132. Ultrasound pulses with a PD of 3 cycles, a PRF of 20 kHz, an $I_{SPPA}$ of 4000 W/cm², and gas concentration of 40% were applied.

FIG. 4 illustrates waveforms of acoustic backscatter corresponding to the data in FIG. 3. All the backscatter waveforms are 20 μs long range gated from the erosion zone. "a"-"f" 122-132 are the initiation and extinction points shown in FIG. 3.

FIG. 5 shows different acoustic backscatter signals and corresponding tissue effects generated by the same ultrasound exposure in three treatments. The first row shows the acoustic backscatter in fast time and slow time display. The second row shows the backscatter power versus time. The third row shows the moving SD of backscatter power versus time. The x-axis (time) for each column is the same and shown above each column. The y-axis for each row is the same and shown on the left side of each row. The fourth row depicts the tissue effects on porcine atrial wall tissue samples generated by the corresponding treatments. The photographs depict the tissue sample 134 and the subdivided (eroded) tissue 136.

All the tissue samples were treated by a total of 8 min ultrasound pulses at an ISPPA of 3500 W/cm², a PD of 3 cycles, a PRF of 20 kHz, and gas concentration of 40-45%. In panel A, neither initiation nor erosion was observed. In panel B, initiation ("a") 138 and extinction ("b") 140 were detected and erosion was observed, but tissue was not perforated. In panel C, initiation ("c") 142 was detected and erosion was observed, and tissue was perforated ('d') 144.

Experimental Design: The initiation and extinction processes and the relationship of initiation to erosion were studied through observations of the acoustic backscatter and the tissue effects generated by corresponding ultrasound exposures. Moreover, the effects of pulse intensity and gas concentration on initiation delay time were investigated. Initiation delay time here is defined as the time interval between the onset of acoustic pulses and the first initiation (as previously defined) of the variable backscatter. Initiation delay time values reported here only includes the cases when an initiation was detected. Initiation and extinction were monitored by the acoustic backscattering signal received by the 5 MHz monitoring transducer 104 and detected by the methods described herein.

For studying the effects of pulse intensity on the initiation delay time, the gas concentration was set to 39-49%. $I_{SPPA}$ values of 1000, 2000, 3000, 4000, 5000, 7000, 9000 W/cm² were tested. Corresponding peak positive pressures and peak negative pressures are listed in Table 1. The actual waveforms of 3-cycle pulses at $I_{SPPA}$ values between 1000-9000 W/cm² are given in FIG. 6.

TABLE 1

$I_{SPPA}$ and peak positive and negative pressures
(pulse duration = 3 cycles)

| $I_{SPPA}$ (W/cm²) | Peak Positive Pressure (MPa) | Peak Negative Pressure (MPa) |
|---|---|---|
| 1000 | 7.8 | 5.2 |
| 2000 | 11.7 | 6.6 |
| 3000 | 15.2 | 7.5 |
| 3500 | 16.7 | 7.9 |
| 4000 | 18.3 | 8.3 |
| 5000 | 21.4 | 9.0 |
| 7000 | 27.3 | 10.1 |
| 9000 | 36 | 11.6 |

Figure 6:
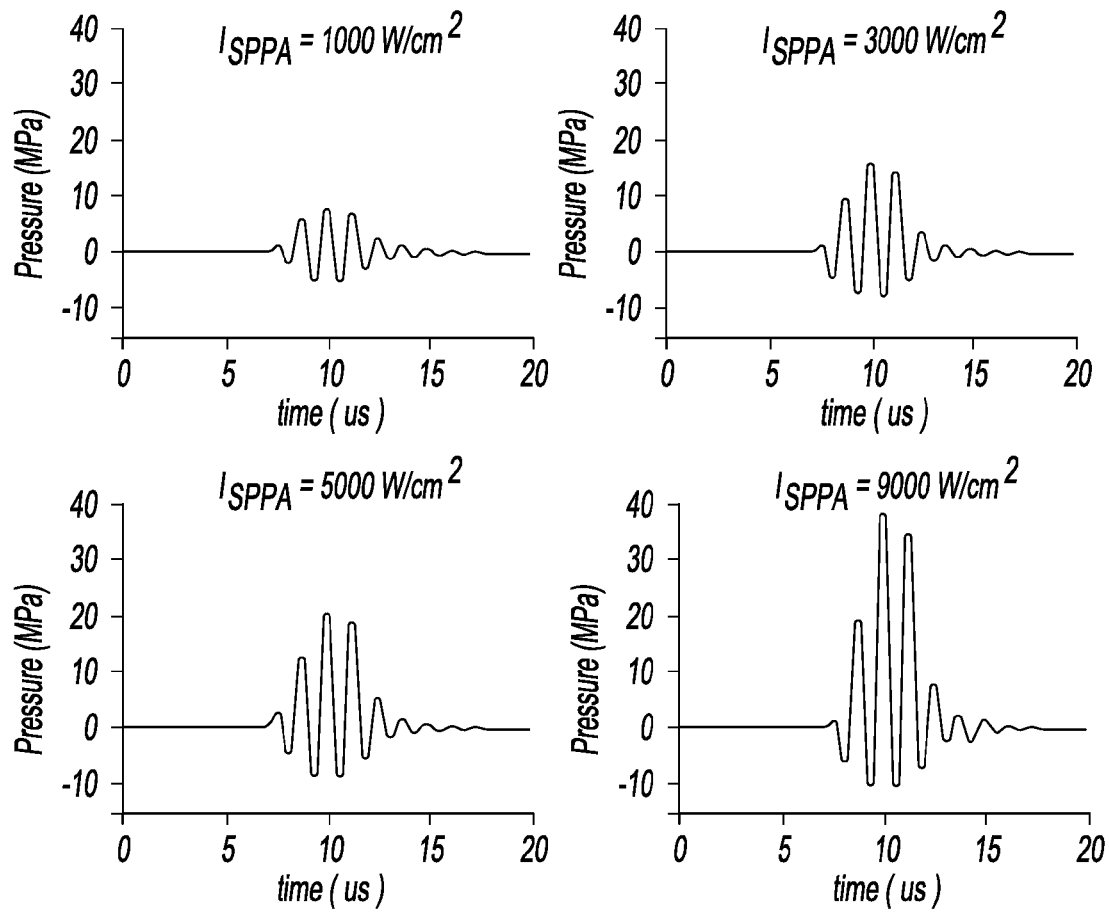

FIG. 6 shows the waveforms of therapeutic ultrasound pulses with a PD of 3 cycles and $I_{SPPA}$ values of 1000, 3000, 5000 and 9000 W/cm2 delivered by the 788-kHz therapy transducer 102 as recorded by a membrane hydrophone.

For studying effects of gas concentration on initiation delay time, $I_{SPPA}$ was kept constant at 5000 W/cm². Gas concentration of three different ranges of 24-28%, 39-49%, 77-81% were used. The partial pressure of oxygen (PO2) in air was used as our metric for gas concentration and the PO2 level was measured with YSI Dissolved Oxygen Instruments (Model 5000, YSI, Yellow Springs, Ohio USA).

A pulse duration (PD) of 3 cycles and a pulse repetition frequency (PRF) of 20 kHz were used in all ultrasound exposures. This parameter set was chosen because it achieved the fastest erosion. The parameters used in these experiments were randomized. All the data were also used in the study of the initiation and extinction processes and the relationship of initiation to erosion.

Results: A total of 95 ultrasound treatments were applied to 33 pieces of 1-3 mm thick porcine atrial wall. The acoustic backscatter signals recorded and tissue effects produced by the corresponding ultrasound treatments are included in the following analysis. The initiation phenomenon was observed in 62 of 95 treatments (Table 2). The extinction (excluding perforation) phenomenon was observed in 17 of 95 treatments (Table 3).

Relationship between Initiation and Erosion: Results show that initiation and erosion are highly correlated. As shown in Table 2, no erosion was observed in any of the 33 treatments where initiation was not detected. Among 61 of 62 treatments where initiation was detected, visible erosion was also observed in the tissue. Therefore initiation predicted erosion, or lack or erosion, successfully at a rate of 98.9% (94 out of 95 treatments).

FIG. 5 graphically depicts the correlation between initiation and erosion. All three tissue samples were treated for 8 min by ultrasound pulses with a PD of 3 cycles, a PRF of 20 kHz, an $I_{SPPA}$ of 3500 kHz and a gas concentration range of 40-45%. The first three rows show the backscatter in fast time and slow time display, backscatter power versus time, and moving SD of the backscatter power versus time, respectively. The pictures in the last row show the tissue effects generated by corresponding ultrasound treatments. In panel A, a nearly flat backscatter power moving SD trace indicates that no initiation occurred, and there was no erosion in the tissue 134. In panel B and C, the backscatter power moving SD increased significantly and remained high for a period of time. Correspondingly, erosion 136 appeared in both tissue samples.

TABLE 2

Number of recorded initiation and erosion events

| $I_{SPPA}$ (W/cm²) | Gas Concentration | Number of Treatments | Initiation and Erosion | No Initiation and No Erosion | Initiation but No Erosion | No Initiation but Erosion |
|---|---|---|---|---|---|---|
| 1000 | 39-49% | 12 | 0 | 12 | 0 | 0 |
| 2000 | 39-49% | 12 | 0 | 11 | 1 | 0 |
| 3000 | 39-49% | 12 | 4 | 7 | 0 | 0 |
| 3500 | 39-49% | 8 | 5 | 3 | 0 | 0 |
| 4000 | 39-49% | 12 | 12 | 0 | 0 | 0 |
| 5000 | 24-28% | 8 | 8 | 0 | 0 | 0 |
| 5000 | 39-49% | 8 | 8 | 0 | 0 | 0 |
| 5000 | 77-81% | 8 | 8 | 0 | 0 | 0 |
| 7000 | 39-49% | 8 | 8 | 0 | 0 | 0 |
| 9000 | 39-49% | 8 | 8 | 0 | 0 | 0 |
| Treatment Number | | 95 | 61 | 33 | 1 | 0 |
| Success Prediction Rate | | | | 98.9% | | |

TABLE 3

Number of recorded extinction (excluding perforation) events

| $I_{SPPA}$ (W/cm$^2$) | Gas Concentration | Number of Treatments | Number of Treatments with Extinction (excluding perforation) | Number of Extinction Events |
|---|---|---|---|---|
| 1000 | 39-49% | 12 | 0 | 0 |
| 2000 | 39-49% | 12 | 1 | 1 |
| 3000 | 39-49% | 11 | 4 | 5 |
| 3500 | 39-49% | 8 | 4 | 13 |
| 4000 | 39-49% | 12 | 6 | 8 |
| 5000 | 24-28% | 8 | 1 | 1 |
| 5000 | 39-49% | 8 | 0 | 0 |
| 5000 | 77-81% | 8 | 0 | 0 |
| 7000 | 39-49% | 8 | 1 | 1 |
| 9000 | 39-49% | 8 | 0 | 0 |
| Treatment Number | | 95 | 17 | 29 |

Variability of Initiation and Extinction: Initiation was highly stochastic in nature, particularly at intermediate intensities (~3000 W/cm$^2$). For example, at $I_{SPPA}$'s of 3000 and 3500 W/cm$^2$, initiation occurred in an unpredictable manner (Table 4). The same 8-min ultrasound exposure (3 cycle PD, 20 kHz PRF and 39-49% gas concentration) was applied to all the treatments reported in Table 4. Neither initiation nor erosion was observed in 10 of 19 treatments. However, both initiation and erosion were observed in the other 9 cases.

After initiation, extinction also occurred in a random manner at intermediate intensities. An 8 min ultrasound exposure ($I_{SPPA}$'s of 3000-4000 W/cm$^2$, 3-cycle PD, 20-kHz PRF, 39-49% gas concentration) was applied to all the treatments in Table 5. But of 21 treatments when initiation was observed, extinction was detected in 14 cases.

rated. In 2 treatments, multiple extinction and reinitiation events occurred, and erosion without perforation was observed. In the remaining 9 treatments, multiple extinction and reinitiation events were observed, and tissue was eventually perforated.

FIG. 5 demonstrates the variability of initiation and extinction resulting in different tissue effects even when the same acoustic parameters were applied. In panel A, neither initiation nor erosion was seen. In panel B, both initiation and extinction were detected, and the tissue was eroded, although no perforation occurred within the 8 min exposure. In panel C, initiation without extinction was observed, and the tissue was perforated.

Figure 7:
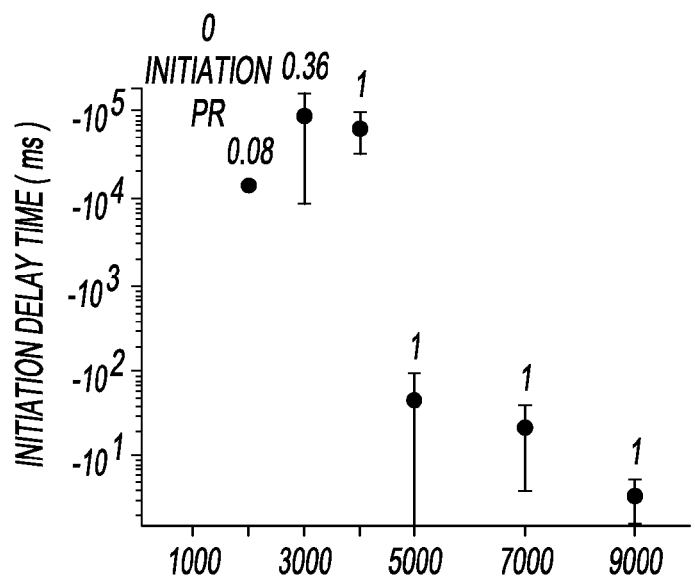

Initiation Delay Time vs. Intensity: FIG. 7 shows the initiation delay time versus $I_{SPPA}$. Multiple pulses at a PD of 3 cycles, a PRF of 20 kHz, and $I_{SPPA}$ values of 1000, 2000, 3000, 4000, 5000, 7000 and 9000 W/cm$^2$ were applied. The gas concentration was kept at 39-49%. At $I_{SPPA} \leq 1000$ W/cm$^2$, initiation was never observed within the 8 min ultrasound exposure. At $I_{SPPA}$ between 2000 and 3000 W/cm$^2$, initiation sometimes occurred and the probability of initiation increased with intensity. The probability of initiation is defined as the number of trials where initiation was detected divided by the total number of trials using the parameter set. At $I_{SPPA} \geq 4000$ W/cm$^2$, initiation always occurred.

FIG. 7 shows the initiation delay time as a function of $I_{SPPA}$. $I_{SPPA}$ values of 1000, 2000, 3000, 4000, 5000, 7000 and 9000 W/cm$^2$ were tested. A PD of 3 cycles, a PRF of 20 kHz and a gas concentration range of 39-49% were used for all the ultrasound exposures. Initiation delay time was plotted as mean and standard deviation values. The sample size is listed in Table 6. The number above each data point is the probability of initiation.

TABLE 4

Number of recorded initiation, erosion and perforation events at $I_{SPPA}$ values of 3000-3500 W/cm$^2$

| $I_{SPPA}$ (W/cm$^2$) | Number of Treatments | No Initiation and No Erosion | Initiation and Erosion | Initiation and Erosion, No perforation | Initiation and Perforation | No initiation, but Erosion | Initiation but No Erosion |
|---|---|---|---|---|---|---|---|
| 3000 | 11 | 7 | 4 | 4 | 0 | 0 | 0 |
| 3500 | 8 | 3 | 5 | 1 | 4 | 0 | 0 |
| Treatment Number | 19* | 10* | 9* | 5 | 4 | 0 | 0 |

*marks the columns referred to in the text.

TABLE 5

Number of recorded extinction and reinitiation events at $I_{SPPA}$ values of 3000-4000 W/cm$^2$

| $I_{SPPA}$ (W/cm$^2$) | Number of Treatments | Initiation and Erosion | Extinction | Extinction, No Reinitiation and No Perforation | Extinction, Reinitiation but No Perforation | Extinction, Reinitiation and Perforation |
|---|---|---|---|---|---|---|
| 3000 | 11 | 4 | 4 | 3 | 1 | 0 |
| 3500 | 8 | 5 | 4 | 0 | 1 | 3 |
| 4000 | 12 | 12 | 6 | 0 | 0 | 6 |
| Treatment number | 31 | 21* | 14* | 3* | 2* | 9* |

Figure 8A:
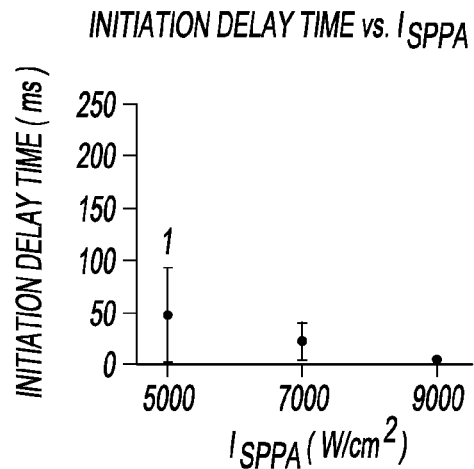

Furthermore, in some treatments, reinitiation of the variable backscatter after extinction occurred in an unpredictable manner (Table 5). In 3 out of the 14 treatments where extinction was detected, no subsequent reinitiation occurred. Erosion was observed, none of these tissue samples were perfo- The initiation delay time is dependent upon intensity. It was shorter with higher intensity (FIG. 7, FIG. 8A). The mean and SD values of initiation delay time at each $I_{SPPA}$ and the sample size for each $I_{SPPA}$ are listed in Table 6. For example, the mean initiation delay time was 66.9 s at an $I_{SPPA}$ of 4000

W/cm$^2$ and 3.6 ms at an $I_{SPPA}$ of 9000 W/cm$^2$, a 4-order of magnitude difference (p<0.0001; T-test). Variances in the initiation delay times were also lower with higher intensity. For example, the SD in initiation delay time was 33.3 s at an $I_{SPPA}$ of 4000 W/cm$^2$ and 1.9 ms at an $I_{SPPA}$ of 9000 W/cm$^2$, a 4-order of magnitude difference.

FIG. 8 shows the initiation delay time vs. intensity and gas concentration. Panel A shows the initiation delay time as a function of $I_{SPPA}$. $I_{SPPA}$ values of 5000, 7000 and 9000 W/cm$^2$ were tested. A PD of 3 cycles, a PRF of 20 kHz and a gas concentration range of 39-49% were applied to all the exposures in Panel A. Panel B shows the initiation delay time as a function of gas concentration. Gas concentration ranges of 24-28%, 39-49%, 77-81% were tested and plotted as gas concentrations of 25%, 45% and 80% for convenience of display. A PD of 3 cycles, a PRF of 20 kHz and an $I_{SPPA}$ of 5000 W/cm$^2$ were applied to all the exposures in Panel B. Initiation delay time is plotted as mean and SD values (N=8) in both panels. The number above each data point is the probability of initiation.

TABLE 6

Initiation delay time

| $I_{SPPA}$ (W/cm$^2$) | Gas Concentration | Sample Sizes | Number of initiations | Initiation Percentage | Initiation delay time (ms) Mean | Standard Deviation |
|---|---|---|---|---|---|---|
| 1000 | 39-49% | 12 | 0 | 0 | — | — |
| 2000 | 39-49% | 12 | 1 | 8.3% | 14459.2 | 0 |
| 3000 | 39-49% | 11 | 4 | 36.4% | 88429.9 | 79879.6 |
| 4000 | 39-49% | 12 | 12 | 100% | 66865.3 | 33287.4 |
| 5000 | 24-28% | 8 | 8 | 100% | 133.1 | 78.3 |
| 5000 | 39-49% | 8 | 8 | 100% | 48.0 | 46.4 |
| 5000 | 77-81% | 8 | 8 | 100% | 24.7 | 25.0 |
| 7000 | 39-49% | 8 | 8 | 100% | 22.1 | 18.0 |
| 9000 | 39-49% | 8 | 8 | 100% | 3.6 | 1.9 |

Figure 8B:
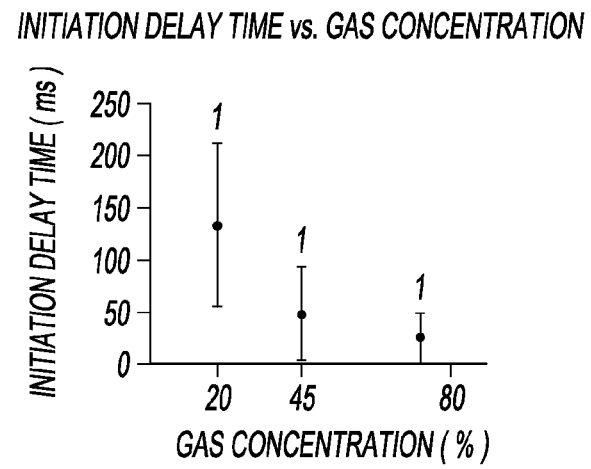

Initiation Delay Time vs. Gas Concentration: Multiple pulses at a PD of 3 cycles, a PRF of 20 kHz, and an $I_{SPPA}$ of 5000 W/cm$^2$ were applied. Gas concentration in the ranges of 24-28%, 39-49%, and 77-81% were used to study the effects of gas concentration on initiation delay time. The sample size was eight for each gas concentration range. Results show that the initiation delay time was shorter with higher gas concentration (FIG. 8B). For example, the mean initiation delay times were 133.1 ms, 48.0 ms, and 24.7 ms at gas concentration ranges of 21-24%, 39-49% and 77-81% respectively (Table 6). The variances of initiation delay times were lower with higher gas concentration. For example, the SD of initiation delay time were 78.3 ms, 46.4 ms, and 25.0 ms at gas concentration ranges of 21-24%, 39-49% and 77-81%, respectively (Table 6).

These experiments illustrate a high correlation between enhanced, rapidly changing acoustic backscatter and the erosion process. The presence and absence of initiation of the variable backscatter successfully predict erosion and lack of erosion at a rate of 98.9%. The appearance of this backscatter pattern can be used as a real-time indicator that erosion is progressing normally. Initiation delay time, presumably the formation time of the bubble cloud, decreases with higher intensity and higher gas concentration.

Example 2

Optical and Acoustic Feedback and Monitoring of Bubble Cloud Dynamics

Optical Detection: The optical attenuation method detects light absorption and scattering by the bubbles when a bubble cloud is created. A laser beam is projected through the ultrasound focus in front of the tissue and the light intensity is monitored continuously by a photodetector. Optical attenuation detection is capable of monitoring real-time bubble cloud dynamics without interference from the tissue or disturbing the ultrasound field, yet simple and of low cost. The temporal resolution of the optical attenuation method depends on the response time of the photo-detector. It can easily reach nanoseconds or better with very reasonable cost equipment. This enables almost continuous monitoring of the bubble cloud compared to the time scale of acoustic therapy pulse (on the order of µs and above). Using this detection scheme, we expect to gain much fundamental knowledge of the temporal dynamics of the bubble cloud that will be highly relevant to optimizing the acoustic parameters for ultrasound erosion.

Although optical attenuation can resolve much temporal dynamics of the bubble cloud and may provide some relative spatial changes of the bubble cloud, it is unable to provide any absolute spatial information of the cloud (e.g., overall size and shape) or any information of individual bubbles. Optical imaging can visualize the overall size and shape of the bubble cloud, as well as the shape and size distribution of individual microbubbles [P. Huber, K. Jochle, and J. Debuss, "Influence of shock wave pressure amplitude and pulse repetition frequency on the lifespan, size and number of transient cavities in the field of an electromagnetic lithotripter," Physics in Medicine and Biology, vol. 43, pp. 3113-28, 1998; C. D. Ohl, T. Kurz, R. Geisler, O. Lindau, and W. Lauterborn, "Bubble dynamics, shock waves and sonoluminescence," Phil. Trans. R. Soc. Lond. A, vol. 357, pp. 269-294, 1999; W. Lauterborn and W. Hentschel, "Cavitation bubble dynamics studied by high speed photography and holography: part one," Ultrasonics, vol. 23, pp. 260-8, 1985; D. L. Sokolov, M. R. Bailey, and L. A. Crum, "Use of a dual-pulse lithotripter to generate a localized and intensified cavitation field," Journal of the Acoustical Society of America, vol. 110, pp. 1685-1695, 2001; J. Appel, P. Koch, R. Mettin, D. Krefting, and W.

Lauterborn, "Stereoscopic high-speed recording of bubble filaments," Ultrasonics Sonochemistry, vol. 11, pp. 39-42, 2004; F. Burdin, P. Guiraud, A. M. Wilhelm, and H. Delmas, "Implementation of the laser diffraction technique for cavitation bubble investigations," Part. Part. Syst. Charact., vol. 19, pp. 73-83, 2002.], if the spatial resolution is good enough. This method typically employs a collimated light source to illuminate the cloud, and record direct images of the bubble cloud with a high speed camera behind a compact long distance microscope.

Acoustic Detection; Optical monitoring is difficult to achieve in vivo. Acoustic detections including acoustic backscatter and low frequency acoustic emission will be compared with optical data, to discover a likely candidate for monitoring bubble dynamics and perhaps the erosion process in vivo. Acoustic scattering and emission are simple and widely-used means to monitor cavitation [R. A. Roy, A. A. Atchley, L. A. Crum, J. B. Fowlkes, and J. J. Reidy, "A precise technique for the measurement of acoustic cavitation thresholds and some preliminary results," Journal of the Acoustical Society of America, vol. 78, pp. 1799-805, 1985; C. K. Holland and R. E. Apfel, "Thresholds for transient cavitation produced by pulsed ultrasound in a controlled nuclei environment," J. Acoust. Soc. Am., vol. 88, pp. 2059-2069, 1990; A. A. Atchley, L. A. Frizzell, R. E. Apfel, C. K. Holland, S. Madanshetty, and R. A. Roy, "Thresholds for cavitation produced in water by pulsed ultrasound," Ultrasonics., vol. 26, pp. 280-5, 1988.].

Acoustic backscatter relies on the reflection and scattering of the insonating sound field by the bubble cloud, providing the information of the bubble cloud during therapy pulses. The initiation and extinction of an enhanced and highly fluctuating backscatter have shown high correlation with the beginning and suspension of cavitation.

Hydrophone acquired low frequency acoustic emission can facilitate real-time monitoring of the acoustic emission of the bubble clouds during and between the acoustic therapy pulses. Two major advantages of using low frequencies are: (1) reducing interference of therapy pulses by filtering out high frequency components particularly at the fundamental, harmonic and subharmonic frequency components of the therapy transducer; and (2) less acoustic attenuation through tissue at low frequencies. These attributes make the low frequency acoustic emission a possible candidate for in vivo monitoring of bubble dynamics.

Figure 9:
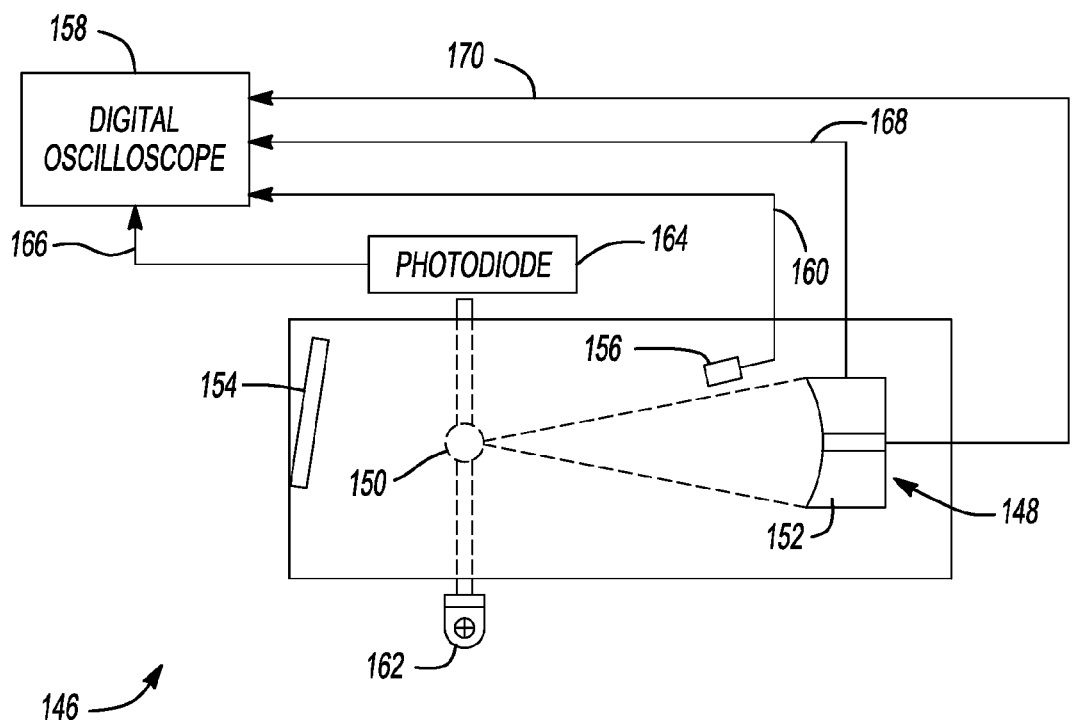

Ultrasound Generation: FIG. 9 illustrates the experimental apparatus 146. Ultrasound pulses are generated by an 18 element array 148, which is used to generate the bubble cloud 150 (where the tissue sample would be placed for therapy). Coupled to the array 148 is a 5 MHz transducer 152 and beyond the bubble cloud 150 is a sound absorber 154. A low frequency hydrophone 156 is located along the ultrasound focal path, the hydrophone 156 being coupled to a digital oscilloscope 158, wherein the coupling can transfer low frequency acoustic emissions 160. The oscilloscope 158 is further coupled to a PC computer (not shown). A laser 162 projects across the location of the bubble cloud 150 to a photodiode 164, which is coupled to the oscilloscope 158 to transfer optical attenuation signals 166. The oscilloscope is further coupled to the array 148 and transducer 152 to allow transfer of a therapy pulse trigger 168. Acoustic backscatter 170 can also be transmitted between the coupling the array 148/transducer 152 and the oscilloscope 158.

Ultrasound pulses are generated by an 18-element piezo-composite spherical-shell therapeutic array 148 (Imasonic, S.A., Besançon, France) with a centre frequency of 750-kHz and a geometric focal length of 100-mm. The therapy array 148 has an annular configuration with outer and inner diameters of 145 and 68 mm, respectively, yielding a radiating area of ~129 $cm^2$. A PC console (not shown) (Model Dimension 4100, Dell, Round Rock, Tex. USA) provided control of a motorized 3-D positioning system (not shown) (Parker Hannifin, Rohnert Park, Calif. USA) to position the array 148 at each exposure site. The array driving system, consisting of channel driving circuitry, associated power supplies (Model 6030A, HP, Palo Alto, Calif. USA), and a software platform to synthesize driving patterns, were also maintained under PC control. The 18-element array 148 can achieve acoustic intensity high enough to create a bubble cloud 150 with a single short pulse, providing a wide dynamic range to study bubble cloud dynamics.

Ultrasound Calibration; Pressure waveform at the focus of the 18-element array 148 in the acoustic field was measured in degassed water (12-25% concentration) (i.e., free-field conditions) using a fiber-optic probe hydrophone 156 (FOPH) developed in-house for the purpose of recording high-amplitude pressure waveforms. The sensitive element of the hydrophone 156 is a 100-μm diameter cleaved endface of graded-index multimode optical fiber. The FOPH end-of-cable loaded sensitivity (ML(f) at f≈750 kHz) was determined by comparing waveforms recorded over a limited amplitude range using a calibrated PVDF bilaminar shielded membrane hydrophone of known sensitivity (model IP056, GEC Marconi Research Center, Chelmsford, U.K., calibration performed by Sonic Consulting, Wyndmoor, Pa. USA) to those recorded using the FOPH 156 to identify the appropriate conversion factor for voltage waveforms generated by the FOPH 156. Theoretical calculations of expected pressures based upon the configuration of the FOPH system agree within ~20% with measured pressures. The lateral and axial pressure profiles of the focused beam were measured to be ~2 mm×10 mm in width (FWHM) and confirmed at low amplitudes via numerical simulations performed in MATLAB® (MathWorks, Inc., Natick, Mass. USA). Spatial-peak pulse-average intensity (ISPPA) as defined by the AIUM [AIUM, Acoustic Output Measurement Standard for Diagnostic Ultrasound Equipment, UD2-98: AIUM/NEMA, 1998.] is often used to represent the amplitude of acoustic pulses. However, the amplitudes of the therapy pulses employed are comparable to lithotripter pulses and are highly non-linear. The broad frequency content of the highly-nonlinear pressure waveforms generated may conflict with other assumptions commonly used in intensity estimations of more linear acoustic fields. Therefore, the peak negative pressure and the peak positive pressure are used as a metric for the amplitude of the acoustic therapy pulses. The values of peak negative and positive pressures and ISPPA used in this study are measured for free-field conditions only and listed in Table 7.

TABLE 7

Parameters used to study bubble cloud dynamics

| Study | PD (cycles) | P+ (MPa) | P− (MPa) | $I_{SPPA}$ (W/cm²) | PRF (kHz) | Gas Concentration | Tissue Presence |
|---|---|---|---|---|---|---|---|
| Initiation (example) | 3 | 19.1 | 54.5 | 20.9 k | 2 | 33-40% | Free water |
|  | 3 | 14.7 | 28.4 | 10.9 k | 2 | 22-24% | Tissue-water |
| Extinction (example) | 3 | 15.5 | 31.9 | 12.4 k | 0.2 | 98-100% | Free water |
|  | 3 | 13.9 | 25.1 | 9.5 k | 0.2 | 98-100% | Tissue-water |
| Effects of Pulse Duration | 3 (5 µs) 6 (9 µs) 12 (17 µs) 24 (33 µs) | >21 | >76 | >26 k | Single Pulse | 24-26% 98-100% | Free water Tissue-water |
| Effects of Pulse Pressure | 3 | 13.9 15.5 17.1 | 25.1 31.9 39.7 | 9.5 k 12.4 k 15.6 k | 2 | 33-40% | Tissue-water |
| Effects of PRF | 3 | 15.5 | 31.9 | 12.4 k | 0.5 2 5 10 20 | 22-24% | Tissue-water |
| Effects of Gas Concentration | 3, 6, 12, 24 | >21 | >76 | >26 k | Single Pulse | 24-26% 98-100% | Free water Tissue-water |
| Effects of Tissue Presence | 3, 6, 12, 24 | >21 | >76 | >26 k | Single Pulse | 24-26% 98-100% | Free water Tissue-water |

Exposure Condition: The dependence of bubble cloud dynamics generated by ultrasound pulses on acoustic parameters (e.g., pulse duration, pulse pressures and pulse repetition frequency) and the gas content in the water were investigated both in free water and at a tissue-water interface. Bubble clouds were produced in a 30-cm wide×60-cm long× 30-cm high water tank designed to enable optical observations. To create the tissue-water interface, a piece of ~3-cm-wide×~3-cm-long×~2-mm thick porcine atrial wall is positioned at the focus of the array and ~1-2 mm behind the laser beam.

A single pulse and multiple pulses delivered by the phased array are used to create bubble clouds in this study. The purpose of using a single pulse is to monitor the bubble cloud without the influence from adjacent pulses. The results of bubble cloud dynamics generated by a single pulse were used to study the dependence of the bubble cloud on pulse duration and gas concentration both in free water and a tissue-water interface. Pulse durations of 3, 6, 12, 24 cycles and gas concentration ranges of 24-26% and 98-100% were tested. The same pulse pressures were employed, but the focal pressure field could not be successfully measured due to the rapid onset of cavitation. Extrapolation of the peak negative pressure and the peak positive pressure in the focal zone measured by the fiber-optic hydrophone at a lower power yielded 21 MPa and 76 MPa, respectively. A sample size of 3-8 was used for each combination of parameters.

Multiple pulses were used to investigate the dependence of the bubble cloud created at a tissue-water interface on pulse pressures and pulse repetition frequency (PRF). The reason for using multiple pulses to study effects of pulse pressures on the bubble cloud is because the pressure level required to reliably produce a bubble cloud with a single pulse is close to the maximal pressure the 18-element therapy transducer can achieve. Moreover, the pressure levels in that range cannot be measured due to the rapid onset of cavitation. To study the effects of pulse pressure on the bubble cloud, the peak negative pressures of 13.9, 15.5 and 17.1 MPa, and the corresponding peak positive pressures of 25.1, 31.9 and 39.7 MPa were tested. A pulse duration of 3 cycles, a PRF of 2 kHz and a gas concentration range of 33-40% were used. To study the effects of PRF on the bubble cloud, PRF values of 500 Hz, 2 kHz, 5 kHz, 10 kHz and 20 kHz were tested. A pulse duration of 3 cycles, a peak negative pressure of 15.5 MPa, a peak positive pressure of 31.9 MPa, and a gas concentration range of 22-24% were employed. The partial pressure of oxygen (PO2) in air was used as our metric for gas concentration and measured with YSI dissolved oxygen instruments (Model 5000, YSI, Yellow Springs, Ohio USA). Table 7 lists the acoustic parameters and gas concentration ranges used in each specific study.

Optical Attenuation Detection: The optical attenuation method detects light absorption and scattering by bubbles when a bubble cloud is created. A 1-mW Helium-Neon gas laser 162 (Model. 79245, Oriel, Stratford, Conn. USA) with a 1-mm diameter beam width was placed on one side of the tank to emanate a laser beam through the ultrasound focus (and in front of the tissue at a tissue-water interface). The light intensity is monitored continuously by a photodiode 164 (Model DET100, ThorLabs, Newton, N.J. USA) placed on the other side of the tank. To direct the laser beam though the ultrasound focus, the phased array transducer was first pulsed in free water, and a bubble cloud was created at the focus of the transducer. The position of the phased array transducer was then adjusted by the positioning system so that the laser beam shined through the center of the bubble cloud. A piece of porcine atrial wall was then placed 1~2 mm parallel behind the laser beam to form a tissue-water interface. The schematic diagram of the experimental setup is shown in FIG. 9.

Figure 10:
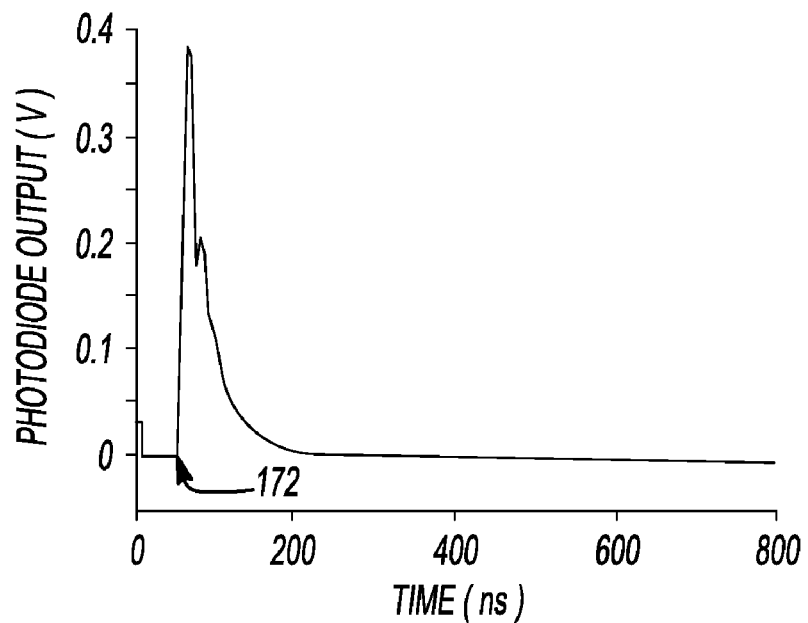

The light attenuation signal was recorded as the voltage output of photodiode. The photodiode output was connected to a four-channel digital oscilloscope (Model 9384L, LeCroy Chestnut, N.Y.) using 1-MΩ DC coupling in parallel with a 250-Ω resistor and displayed as a temporal voltage trace. The resistor was used to convert the photodiode output from a current to a voltage. Through this conversion, the impedance of the resistor determines the voltage level and also changes the response time of the photodiode. The higher impedance yields a higher photodiode output voltage, but a slower response time. An impedance of 250-Ω is chosen to achieve sufficiently high output voltage for a reasonable signal to noise ratio and a high enough dynamic range for attenuation detection, and still maintain a good temporal resolution. FIG. 10 shows the voltage response of the photodiode with the 250-Ω resistor to a 6.8-ns (−3 dB width) laser pulse generated by a Nd:YAG laser (Model Brilliant B, Big Sky Laser Technologies Inc., Bozeman, Mont. USA) with a pumped optical parametric oscillator system (Model Vibrant 532 I, Opotek Inc., Carlsbad, Calif., USA), yielding a −3 dB width response time of 15-ns, a full rise-time of 10-ns, and a full decay-time of 145-ns. This configuration provides 5-times the photodiode voltage output without using any external termination and good temporal resolution to monitor dynamics of the bubble cloud generated by acoustic pulses, at least 1-2 magnitude lower than the time scale of the therapy pulse (on the order of 1 μs) for erosion.

FIG. 10 shows the voltage trace of the photodiode response to a 6.8-ns laser pulse (−3 dB width) with a 250Ω terminator, showing a −3 dB width response time of 15-ns, a full rise-time of 10-ns, and a full decay-time of 145-ns. The arrow 172 indicates the arrival the laser pulse.

The oscilloscope was triggered by a TTL pulse synchronized with the acoustic therapy pulse generated from the array driving electronics. Therefore, the timing of the laser beam change can be referred with respect to the onset of each acoustic pulse. To monitor the bubble cloud generated by a single pulse, the photodiode output is recorded at a 100-MHz sampling frequency and displayed in a 10-ms window starting from onset of the acoustic therapy pulse. To monitor the dynamics of the bubble cloud generated by multiple pulses at a PRF ≧5 kHz, a sampling frequency ≧50-MHz were used to record the photodiode output, the acoustic backscatter, and the therapy pulse trigger. When using PRF <5 kHz, the photodiode output and acoustic backscatter were recorded at a 200-μs ranged-gated window with a sampling frequency of 50-MHz using the sequence mode and single trigger of the digital oscilloscope. The 200-μs ranged-gated window size was chosen to cover most dynamic range of both the optical attenuation and the acoustic backscatter by each therapy pulse. The signals were then transferred from the oscilloscope to a data collection computer through GPIB and processed in MatLab (MathWorks, Natick, Mass. USA).

As the light attenuation is caused by the formation of the bubble cloud, the duration and the peak level of light attenuation are related to the bubble cloud life-time, and the size and density of the bubble cloud, respectively. Therefore the attenuation duration and peak attenuation level are used as characteristics of the bubble cloud dynamics and the focus of this study. The examples of attenuation duration and peak attenuation level are shown as a photodiode voltage output in FIG. 11, in which the light intensity decreased when a bubble cloud was generated by a 6-cycle pulse in free water with a gas concentration range of 98-100%. The pressure levels could not be measured successfully due to the rapid onset of cavitation. Calibrations at a lower power level yield the peak negative and positive pressures of 21 MPa and 76 MPa respectively. Attenuation duration is defined as the duration when the light intensity (photodiode output) falls below a threshold of baseline—3 times the noise level. The baseline is the mean value of the photodiode output when it receives the laser light without the presence of bubbles. The noise level is computed as the standard deviation (SD) of the photodiode output during the absence of bubbles. The peak attenuation level is defined as the difference between the baseline and the minimum voltage divided by the baseline level, ranging between 0 and 1. The minimum voltage excludes the artifact of the photodiode output right after the arrival of the therapy pulse.

Figure 11:
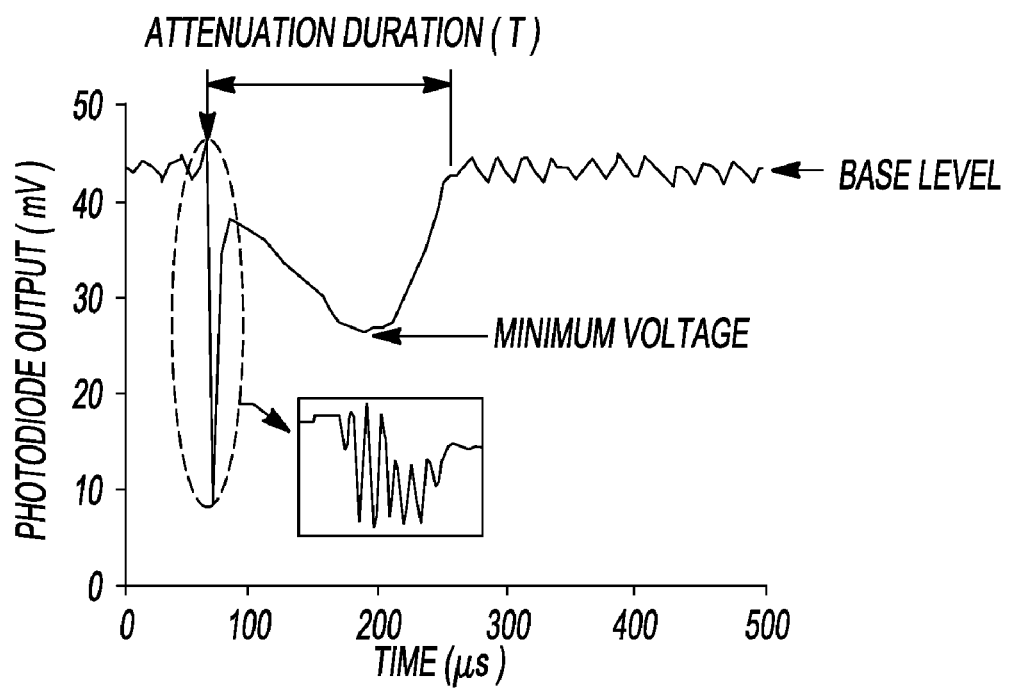

FIG. 11 shows an example of light attenuation caused by formation of the bubble cloud as the photodiode voltage output. The temporal voltage trace of the photodiode output was filtered by a low-pass filter with a 3-MHz cutoff frequency to eliminate the high frequency electrical noise. The bubble cloud was generated by a 6-cycle pulse (9-μs) in free water with a gas concentration range of 98-100%. The top left arrow indicates the arrival of the acoustic therapy pulse at the focus of the therapy transducer where the laser beam is projected. The insert is an expanded view of the artifact of the light attenuation signal during the therapy pulse, which mimics the therapy pulse waveform.

Optical attenuation data are also employed to detect initiation of the bubble cloud formation by multiple pulses. We have shown that initiation of an enhanced and temporal variable acoustic backscatter is highly correlated with the onset of the erosion process. This backscatter pattern is likely a result of the sound reflected of the dynamic bubble cloud. The acoustic backscatter will be compared with the optical attenuation data collected simultaneously to test this supposition. The initiation of a bubble cloud is determined when the attenuation duration exceeds the pulse duration. The purpose of using pulse duration as a threshold is to overcome artifacts of the photodiode output change possibly caused by therapy pulses.

Optical Imaging: Direct images of the bubble cloud were taken by a high speed digital imaging system (Model Phantom V9, Vision Research, Wayne, N.J. USA) at a frame rate of 7 kHz and shutter speed of 2 μs. The bubble cloud was illuminated by a strong light source. The imaging system was placed outside the water tank approximately 100 mm away from the bubble cloud. An optical lens with a focal length of 50 mm-100 mm was mounted in front of the imaging system to increase the magnification.

Acoustic Backscatter: Acoustic backscatter was used to monitor the cavitation activity during the therapy pulses in the focal zone. To receive the acoustic backscatter, a 5-MHz, 2.5-cm diameter single element focused transducer (Valpey Fisher Corporation, Hopkinton, Mass. USA) with a 10-cm focal length was mounted confocally with the therapy array inside its inner hole. The acoustic backscatter signals were recorded and displayed as range-gated temporal voltage traces by a digital oscilloscope (Model 9384L, LeCroy, Chestnut Ridge, N.Y. USA). The recorded waveforms were then transferred through GPIB and processed by the Matlab program (Mathworks, Natick, Mass. USA). The scope setting and data recording setup of the backscatter signals are the same as those of the light attenuation detailed herein.

Enhanced and temporally fluctuating acoustic backscatter signals are widely regarded as one of the acoustic signatures for cavitation. We have shown that initiation of this backscatter pattern is required for producing erosion. Backscatter power and backscatter power moving standard deviation (SD) were used to characterize the amplitude and variability of backscatter and employed to detect initiation. As the acoustic backscatter is due to the sound reflection of the therapy pulses, the backscatter power is normalized to a reference proportional to the therapy pulse power to compare the backscatter characteristics across different pulse pressure levels in this chapter. To obtain the normalized backscatter power, a rectangular window of size equal to the speckle spot size associated with the therapy pulse was applied to the raw (RF)

data to select the primary therapy pulse reflection out of each A-line. The backscatter signal power (PBS) in the range-gated pulse was then computed and normalized to a reference power (PR) determined with a stainless steel reflector. The normalized backscatter power (PNBS=PBS/PR) is therefore ranging from 0 to 1. The normalized backscatter power moving SD (window size=3) is calculated based on the normalized backscatter power and used for detection of initiation and extinction of the variable backscatter pattern. The calculation of the backscatter power moving SD and the statistical criteria to detect initiation and extinction of the variable backscatter are as described herein. The criteria were based on the significantly increased and decreased temporal backscatter variability when "initiation" and "extinction" occur, respectively.

Low Frequency Acoustic Emission: A hydrophone (Model 8103, Brüel & Kjæer, Nærum, Denmark) with a frequency range of 0.1 Hz-180 kHz was placed outside the erosion zone to receive the acoustic emission of the bubble cloud. The sensitivity of this hydrophone is rather constant to frequency components up to 100 kHz, and starts to decline as the frequency exceeds 100 kHz. The hydrophone output signals were amplified by a charge preamplifier (Model 2635, Brüel & Kjær, Nærum, Denmark) before connected to the digital oscilloscope (Model 9384L, LeCroy, Chestnut N.Y. USA). The acoustic emission of bubble clouds was displayed as voltage output of the hydrophone on the oscilloscope and transferred from the oscilloscope to a data collection computer through GPIB and processed in Matlab (Mathworks, Natick, Mass. USA).

Results: Bubble cloud dynamics generated by short high intensity pulses at a tissue-water interface are studied with the goal to understand the underlying mechanism for the ultrasound tissue erosion process. It has been demonstrated previously that initiation of a temporarily variable acoustic backscatter is required for producing erosion. To find the origin of this acoustic backscatter pattern and its relation to the cavitation bubble cloud, optical attenuation signals which monitor the bubble cloud dynamics are compared with acoustic backscatter recorded simultaneously. The optical attenuation results show that the initiation of this acoustic backscatter pattern occurs during insonation because a bubble cloud has been formed.

The duration and the peak level of light attenuation (attenuation duration and the peak attenuation level) are employed here as the main characteristics to study the bubble cloud dynamics. The attenuation duration relates to the life-time of the bubble cloud, and the peak attenuation level relates to the size and density of the bubble cloud. We found out that the focal zone of the transducer remains highly sensitive to the regeneration of the bubble cloud even after the bubble cloud starts to decay.

Conclusions: To understand the mechanism of ultrasound tissue erosion, optical and acoustic methods were employed to monitor dynamics of the bubble cloud generated by short high intensity ultrasound pulses at a soft tissue-water interface. The optical attenuation results demonstrate that initiation of an enhanced and temporally changing acoustic backscatter required for erosion is due to the formation of a bubble cloud. The bubble cloud generated by a short ultrasound pulse lasts significantly longer than the pulse (~10×-100× the pulse duration). Moreover, dynamics of the bubble cloud change with different acoustic parameters and different gas content in the water. For example, the life-time of the bubble cloud, and the size and density of the bubble cloud are greater with longer pulse duration, higher pulse pressure and higher gas concentration. These trends were observed in free water and at a tissue-water interface, while the bubble cloud lasts longer at a tissue-water interface. The life-time of the bubble cloud also increases with greater PRF, when the PRP is longer than duration of the light attenuation. Furthermore, after a bubble cloud starts to decay, the focal zone remains highly sensitive to regeneration of the bubble cloud, although the sensitivity decreases over time.

Example 3

Selection of Parameters to Detect Initiation of Variable Acoustic Backscatter

To identify points of initiation and extinction based on variability in the backscatter signal, we applied a common technique from the area of statistical quality control of industrial processes, the Shewhart chart [G. B. Wetherill and D. W. Brown, Statistical Process Control Theory and practice: Chapman and Hall, 1991]. Depending on the data, different Shewhart charts are used to identify changes in a time series process. For our particular situation, we used the s-chart, where the sample standard deviations (SD) of the backscatter power at point i in the time series is used as the measure of variability. Because only a single measurement of the backscatter power was made at each time point in a given experiment, the SD at a single point can not be directly estimated. For such "one-at-a-time" data, a moving SD approach is employed to estimate the acoustic backscatter variability at certain time point i.

A moving window size of k was employed to estimate the SD at each point i in the time series, SDi. For example, the estimation of SDi was calculated based on the backscatter power at point i and the k−1 points preceding it, from i−k+1 to i. We define initiation to have occurred when five consecutive SDi's exceed the initiation threshold coefficient (m) times the estimated SD of the uninitiated backscatter power. We define extinction to have occurred when five consecutive SDi's fall below a threshold of two times the SD of the uninitiated backscatter power. The SD of the uninitiated backscatter power was estimated from the first n frames of backscatter recorded prior to any high degree of variation in the signal potentially indicating initiation.

In other experiments described herein, an initiation threshold coefficient of four and a moving window size of three were employed. The reason to select these values is discussed here. The effects of initiation threshold m and the moving window size k on initiation detection are investigated.

Methods: The setup to collect acoustic backscatter signals from the erosion zone and the calculation of the backscatter power of the acoustic backscatter signal are shown in FIG. 1. The computation of backscatter power moving SD and estimated SD of uninitiated backscatter power are detailed as the following.

(1) Backscatter Power moving SD: The backscatter power SD of moving window size k at the $i^{th}$ pulse recorded (in slow time) is calculated as SD of k consecutive backscatter power points (the $i^{th}$ point and the k−1 consecutive points before), Backscatter Power moving SD i=SD of (BPi−k+1, . . . , BPi)

$$= \sqrt{\frac{\sum_{j=i-k+i}^{i}[BP_i - mean(BP_{i-k+1} \dots BP_i)]^2}{k-1}}, \quad (1)$$

where SDi is the backscatter power moving SD at the ith pulse recorded, and BPi is the backscatter power at the ith pulse.

(2) Uninitiated Backscatter Power SD: The first n ($10 \leq n \leq 100$) frames of backscatter prior to any high degree of variation in the signal potentially indicating initiation were collected. n above 25 is preferred. The backscatter power SD prior to initiation can be estimated based on the first uninitiated n points using the Shewhart charts (equations 3 and 4).

$$\text{Estimated Uninitiated Backscatter Power } SD = \frac{1}{\hat{\sigma}} \sum_{i=k}^{i} \text{Range}(BP_{i-k+1} \ldots BP_i). \quad (3)$$

$$\text{Range}(BP_{i-k+1} BP_i) = \text{maximum}(BP_{i-k+1} \ldots BP_i) + \text{minimum}(BP_{i-k+1} \ldots BP_i), \quad (4)$$

where $\hat{\sigma}$ is the coefficient to estimate the overall SD from moving SD for a specific window size k. values of $\hat{\sigma}$ corresponding to different k values are listed Table 8.

TABLE 8

Coefficients to estimate uninitiated backscatter power SD using different moving window sizes

| | Size of moving range | | | | | |
|---|---|---|---|---|---|---|
| | 2 | 3 | 4 | 5 | 6 | 7 |
| Coefficient | 1.115 | 1.102 | 1.133 | 1.110 | 1.111 | 1.104 |
| Size of moving range | 8 | 9 | 10 | 11 | 12 | |
| Coefficient | 1.098 | 1.098 | 1.091 | 1.094 | 1.086 | |

Step 1: The uninitiated backscatter power SD was estimated, to set the initiation threshold and the extinction threshold. Initiation threshold is calculated as initiation threshold coefficient m times the estimated SD of the uninitiated backscatter power SD. Extinction threshold is calculated as 2 times the estimated SD of the uninitiated backscatter power SD.

Figure 12:
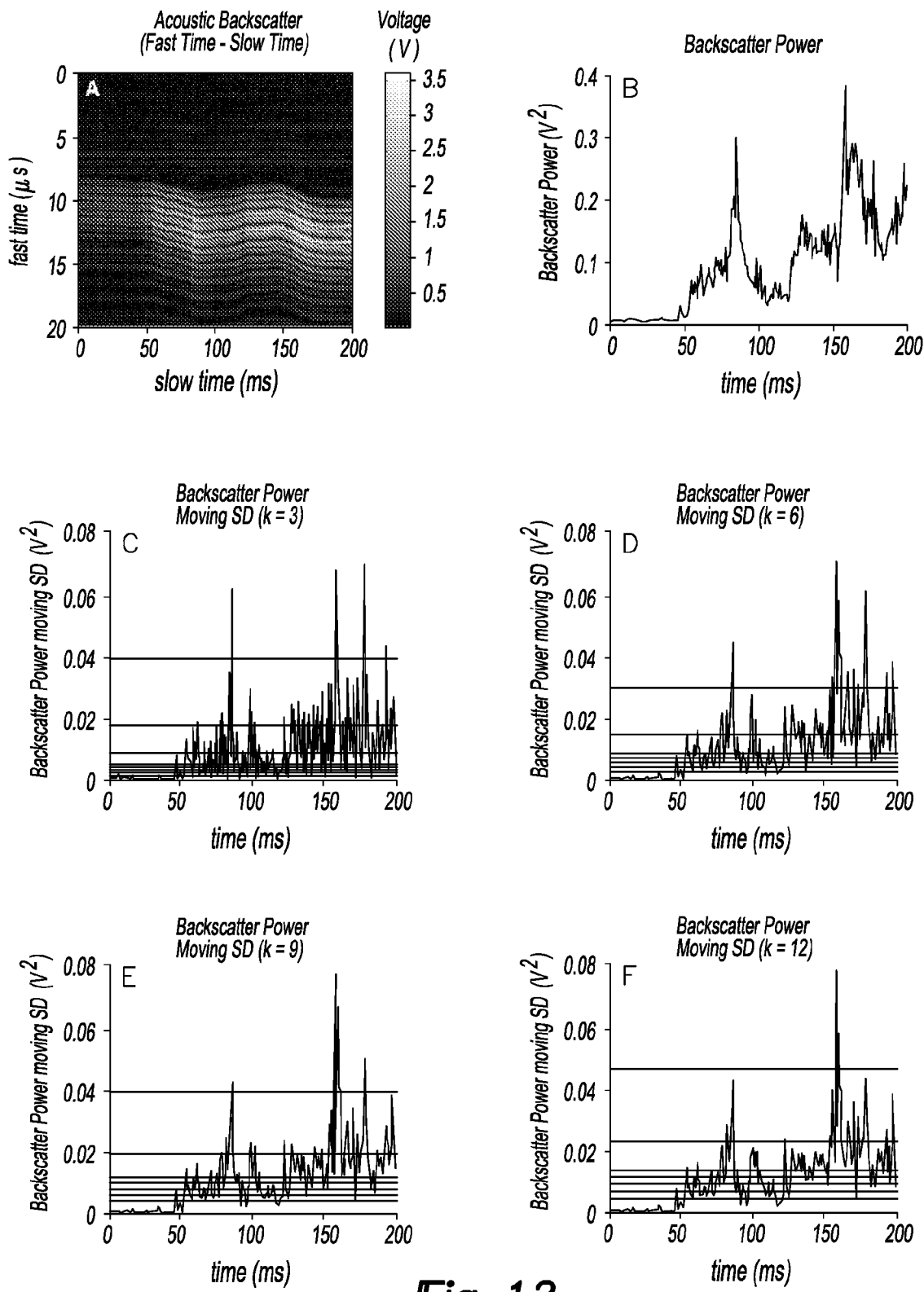

Step 2: the moving SD of backscatter power (window size=k) is calculated and initiation and extinction of the highly backscattering environment were detected based on the criteria described earlier. Initiation threshold coefficients (m) of 2, 3, 4, 5, 6, 10 and 20, and moving window sizes (k) of 3, 6, 9 and 12 were tested. FIG. 12 demonstrates the process of detecting initiation of the variable acoustic backscatter using different values of m and k. The acoustic backscatter and the corresponding erosion data collected from other experiments described herein were employed for the following analysis. A total of 95 ultrasound treatments with a pulse duration of 3 cycles, a PRF of 20 kHz, ISPPA values of 1000-9000 W/cm2 and gas concentration ranges of 24-28%, 39-49% and 77-81% were included. All the experimental parameters tested including ISPPA values with the corresponding peak positive and negative pressures and gas concentration ranges are listed in Table 9. Erosion was observed in 61 of 95 treatments (Table 2). Erosion here is defined as the obvious tissue effects that can be distinguished from the surrounding tissue for the purpose of initiation study.

TABLE 9

Experimental parameters

| $I_{SPPA}$ (W/cm$^2$) | p$^+$ (MPa) | p$^-$ (MPa) | Gas Concentration |
|---|---|---|---|
| 1000 | 7.8 | 5.2 | 39-49% |
| 2000 | 11.7 | 6.6 | 39-49% |
| 3000 | 15.2 | 7.5 | 39-49% |
| 3500 | 16.7 | 7.9 | 39-49% |
| 4000 | 18.3 | 8.3 | 39-49% |
| 5000 | 21.4 | 9.0 | 24-28% |
| 5000 | 21.4 | 9.0 | 39-49% |
| 5000 | 21.4 | 9.0 | 77-81% |
| 7000 | 27.3 | 10.1 | 39-49% |
| 9000 | 36 | 11.6 | 39-49% |

FIG. 12 shows the process of detecting initiation of the variable backscatter using different initiation threshold coefficients and different moving window sizes. Ultrasound pulses with a PD of 3 cycles, a PRF of 20 kHz, ISPPA of 7000 W/cm2, and a gas concentration of 48% were used. Panel A shows the backscattering signals in fast time slow time display. Panel B shows the backscatter power as a function of time. Panel C, D, E and F are the backscatter power moving SD as a function of time with window size of 3, 6, 9 and 12, respectively. And the seven lines from the bottom to up demonstrate the initiation threshold calculated using coefficients m of 2, 3, 4, 5, 6, 10 and 20 respectively.

Results: As shown in Table 10, detected initiation predicted erosion or lack of erosion successfully at a rate $\geq 97.9\%$ (93 of 95 treatments), using the initiation threshold coefficient m of 3 and 4, and any of the moving window size k values tested. The successful prediction rate remains above 92% with any of m values between 2 and 10. However, it decreased to 81.1%-91.6% with the m of 20.

TABLE 10

Number of erosion observed and initiation detected using different initiation threshold coefficients (k) and different moving window sizes (m)

| k | m | Number of total treatments | No Initiation and No Erosion | Initiation and Erosion | No Initiation but Erosion | Initiation but No Erosion | Success Prediction Rate |
|---|---|---|---|---|---|---|---|
| 3 | 2 | 95 | 29 | 61 | 0 | 5 | 94.7% |
| | 3 | 95 | 33 | 61 | 0 | 1 | 98.9% |
| | 4 | 95 | 33 | 61 | 0 | 1 | 98.9% |
| | 5 | 95 | 33 | 60 | 1 | 1 | 97.9% |
| | 6 | 95 | 33 | 59 | 2 | 1 | 96.8% |
| | 10 | 95 | 34 | 57 | 4 | 0 | 95.8% |
| | 20 | 95 | 34 | 53 | 8 | 0 | 91.6% |
| 6 | 2 | 95 | 31 | 61 | 0 | 3 | 96.8% |
| | 3 | 95 | 33 | 61 | 0 | 1 | 98.9% |
| | 4 | 95 | 33 | 61 | 0 | 1 | 98.9% |

TABLE 10-continued

Number of erosion observed and initiation detected using different
initiation threshold coefficients (k) and different moving window sizes (m)

| k | m | Number of total treatments | No Initiation and No Erosion | Initiation and Erosion | No Initiation but Erosion | Initiation but No Erosion | Success Prediction Rate |
|---|---|---|---|---|---|---|---|
|   | 5  | 95 | 33 | 60 | 1  | 1 | 97.9% |
|   | 6  | 95 | 34 | 59 | 2  | 0 | 97.9% |
|   | 10 | 95 | 34 | 56 | 6  | 0 | 93.7% |
|   | 20 | 95 | 34 | 51 | 10 | 0 | 89.5% |
| 9 | 2  | 95 | 33 | 61 | 0  | 1 | 98.9% |
|   | 3  | 95 | 33 | 61 | 0  | 1 | 98.9% |
|   | 4  | 95 | 33 | 60 | 1  | 1 | 97.9% |
|   | 5  | 95 | 34 | 60 | 1  | 0 | 98.9% |
|   | 6  | 95 | 34 | 58 | 3  | 0 | 96.8% |
|   | 10 | 95 | 34 | 55 | 7  | 0 | 93.7% |
|   | 20 | 95 | 34 | 46 | 15 | 0 | 84.2% |
| 12| 2  | 95 | 33 | 61 | 0  | 1 | 98.9% |
|   | 3  | 95 | 33 | 61 | 0  | 1 | 98.9% |
|   | 4  | 95 | 34 | 59 | 2  | 0 | 97.9% |
|   | 5  | 95 | 34 | 58 | 3  | 0 | 96.8% |
|   | 6  | 95 | 34 | 58 | 3  | 0 | 96.8% |
|   | 10 | 95 | 34 | 55 | 7  | 0 | 92.6% |
|   | 20 | 95 | 34 | 43 | 18 | 0 | 81.1% |

Figure 13:
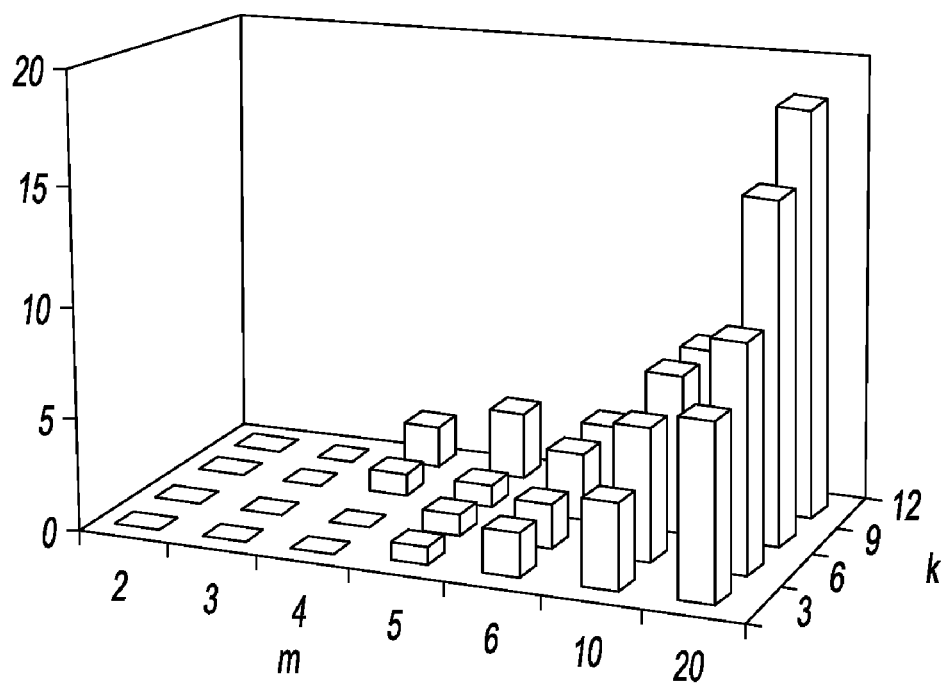

Effects of Initiation Threshold Coefficient on Initiation Detection: As shown in FIG. 13, the number of treatments when erosion occurred but no initiation was detected increased with higher m for a fixed k value. This suggests the false negative rate for initiation detection was greater with a increasing initiation threshold coefficient m. For example, with a k value of 12, the number of erosion without detected initiation was zero for an m of 2 and 18 for an m of 20 (Table 11). It should be noted that this table presents the false negative detections using different values of m and k. The total number of treatments where erosion was observed is 61 of 95 treatments.

TABLE 11

The number of treatments when erosion was observed but
no initiation was detected with different m and k values

| | k | | | |
|---|---|---|---|---|
| m | 3 | 6 | 9 | 12 |
| 2  | 0 | 0 | 0  | 0  |
| 3  | 0 | 0 | 0  | 0  |
| 4  | 0 | 0 | 1  | 2  |
| 5  | 1 | 1 | 1  | 3  |
| 6  | 2 | 2 | 3  | 3  |
| 10 | 4 | 6 | 7  | 7  |
| 20 | 8 | 10| 15 | 18 |

FIG. 13 shows the number of treatments when erosion was observed but no initiation was detected is plotted as functions of the initiation threshold coefficient m and the moving window size k. This is related to the false negative detection rate. The total number of treatments where erosion was observed is 61 of 95 treatments.

Figure 14:
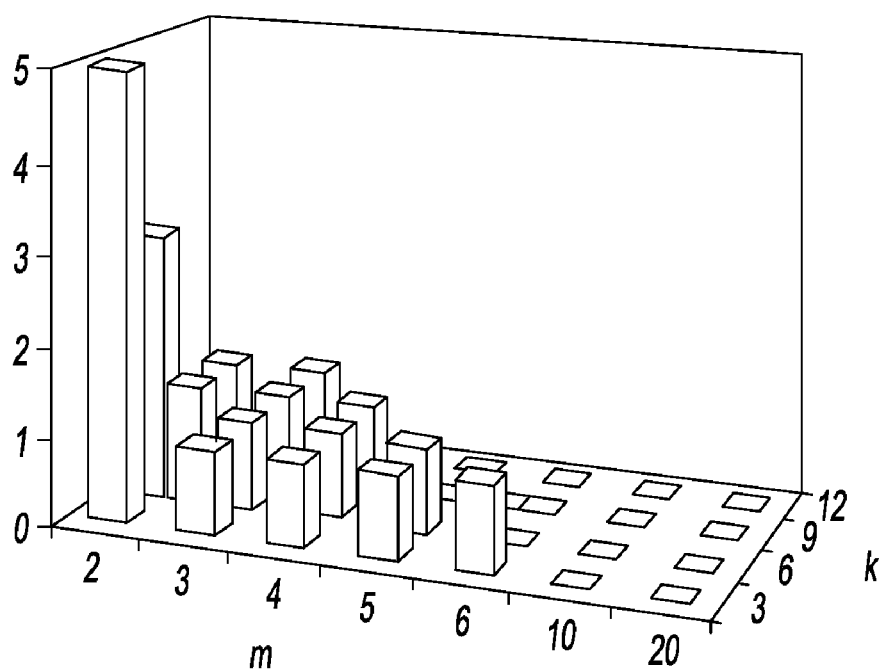

The number of treatments when no erosion was observed but initiation was detected decreased with a higher m for a fixed k value (FIG. 14). This indicates a greater false positive rate for initiation detection with increasing initiation threshold coefficient. For example, with a k value of 3, the number of treatments with detected initiation but no observed erosion was 5 for an m of 2 and zero for an m of 10 or 20 (Table 12). It should be noted that this table presents the false positive detections using different values of m and k. The total number of treatments where no erosion was observed is 34 of 95 treatments.

TABLE 12

The number of treatment when no erosion was observed but
initiation was detected with different m and k values

| | k | | | |
|---|---|---|---|---|
| m | 3 | 6 | 9 | 12 |
| 2  | 5 | 3 | 1 | 1 |
| 3  | 1 | 1 | 1 | 1 |
| 4  | 1 | 1 | 1 | 0 |
| 5  | 1 | 1 | 0 | 0 |
| 6  | 1 | 0 | 0 | 0 |
| 10 | 0 | 0 | 0 | 0 |
| 20 | 0 | 0 | 0 | 0 |

FIG. 14 shows the number of treatments when no erosion was observed but initiation was detected is plotted as functions of m and k. This is related to the false positive detection rate. The total number of treatments where no erosion was observed is 34 of 95 treatments.

Figure 15:
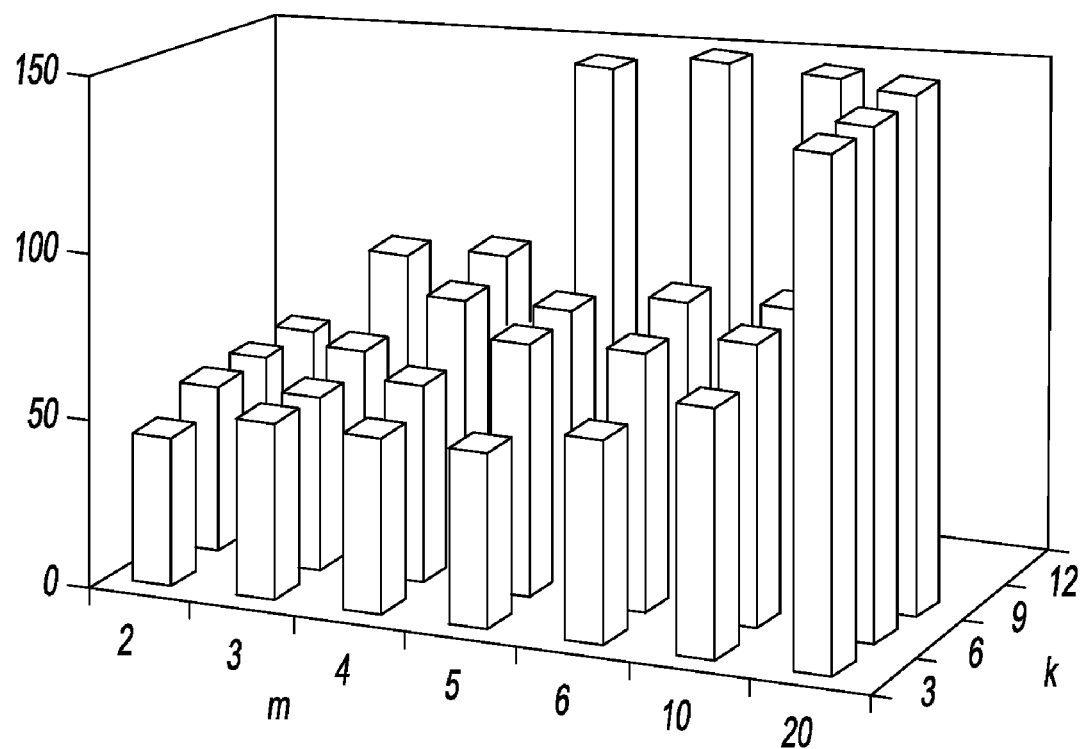

The initiation delay time is defined as the interval between the onset of the acoustic pulses and the first detected initiation of the variable backscatter. This suggests the initiation detection was sharper with a lower m. The initiation delay time detected was longer with a increasing m for a fixed k value (FIG. 15). Using the backscatter signals shown in FIG. 12 as an example, the initiation delay time detected was 46.3 ms for an m of 3 and 158.9 ms for an m of 20 both with a k value of 3, (Table 13).

FIG. 15: Using the backscatter data set shown in FIG. 13, the initiation delay time is plotted as functions of k and m. Ultrasound pulses with a PD of 3 cycles, a PRF of 20 kHz, ISPPA of 7000 W/cm2, and a gas concentration of 48% was used. k values of 3, 6, 9 and 12, and m values of 2, 3, 4, 5, 6, 10 and 20 were tested. Results show that initiation delay time detected increased with higher k and higher m.

TABLE 13

Initiation delay time detected using different k and m values

| k | m | Initiation delay time (ms) | k | m | Initiation delay time (ms) |
|---|---|---|---|---|---|
| 3 | 2 | 46.3 | 6 | 2 | 53.1 |
|   | 3 | 54.3 |   | 3 | 54.3 |
|   | 4 | 54.3 |   | 4 | 60.3 |
|   | 5 | 54.3 |   | 5 | 77.9 |
|   | 6 | 60.3 |   | 6 | 78.1 |
|   | 10 | 74.9 |   | 10 | 84.7 |
|   | 20 | 158.9 |   | 20 | 158.1 |
| 9 | 2 | 53.1 | 12 | 2 | 53.3 |
|   | 3 | 59.1 |   | 3 | 81.9 |
|   | 4 | 78.1 |   | 4 | 84.7 |
|   | 5 | 78.1 |   | 5 | 153.5 |
|   | 6 | 84.7 |   | 6 | 157.9 |
|   | 10 | 84.7 |   | 10 | 157.9 |
|   | 20 | 159.3 |   | 20 | No Initiation |

Effects of Moving Window Size on Initiation Detection: As shown in FIG. 13, the number of treatments when erosion was observed but no initiation was detected tends to increase with higher k for a fixed m value with m≧4. This suggests a higher false negative rate for initiation detection with an increasing moving window size. For example, with an m value of 10, the number of erosion without detected initiation was 4 for a k of 3 and 7 for a k of 12 (Table 11).

The number of events when initiation was detected but no erosion was observed tends to decrease with higher k for a fixed m value with m≦6 (FIG. 14). This indicates the false positive rate for initiation detection increased with a smaller moving window size. For example, with a m value of 2, the number of events with detected initiation but no observed erosion was five for k value of 3 and one for k value of 12 (Table 12).

The initiation delay time detected increased with a higher k for a fixed m value (FIG. 15), suggesting a sharper detection of initiation with a smaller moving window size. Using backscatter signals in FIG. 12 as an example, the initiation delay time detected was 54.3 ms for k value of 3 and 81.9 ms for k value of 12 both with an m value of 3.

Discussion: With appropriately chosen combinations of initiation threshold coefficient m and moving window size k (e.g., m□[3, 4] and k□[3, 6, 9, 12]), detected initiation of the variable backscatter can predict erosion or lack or erosion successfully at a rate ≧97.9% (Table 10). This prediction rate is higher than most methods that have been used to predict cavitational bioeffects (e.g., changes of tissue attenuation coefficient and sound speed in tissue, increased echogenicity). We believe that the initiation of the variable backscatter has a potential to serve as an effective predictor for cavitational bioeffects, therefore decreasing the unpredictability and variability of cavitational bioeffects.

The accuracy of our method to detect the initiation phenomenon depends on two key parameters: the initiation threshold coefficient m and the moving window size k. Here we study effects of m and k values on how accurate the detected initiation can predict erosion and how prompt the initiation can be detected. We hope to find a range of effective working parameters for initiation detection.

The initiation threshold coefficient m determines the confidence level of the initiation detection. When m value is too low, false positive prediction rate is high (i.e., the number of treatment when initiation was detected but no erosion was observed). When m value is too high, false negative prediction rate is high (i.e., the number of treatments when no initiation was detected but erosion was observed). The initiation threshold also affects the detection of initiation delay time. The higher the m value, the less prompt is the detection. If users need to take actions when initiation is detected (e.g., change acoustic parameters when initiation is detected), lower m values are recommended. Our results show that m values of 3 and 4 yield the best results (e.g., the highest successful prediction rate and more prompt initiation detection) among all values tested.

The moving window size k also plays an important role in initiation detection. With appropriately chosen m values (e.g., m=3 or 4), the successful prediction rate remains high with all k values tested. However, the initiation delay time detected was longer using higher k values for a fixed m. It is not surprising that the larger the moving window size, the less sharp the initiation detection. Therefore smaller window size (e.g. k=3 or 6) performs better if prompt initiation detection is needed.

Conclusion: In order to choose appropriate values for the initiation threshold coefficient m and the moving window size k to detect initiation of the variable backscatter, a range of m and k values are tested. The criteria for selecting the initiation threshold coefficient and the moving window size are 1) how accurate the detected initiation can predict erosion and 2) how prompt the initiation can be detected. Results show that the accuracy of prediction of erosion by detected initiation is mainly dependent on the initiation threshold coefficient. The false negative prediction rate is lower with decreasing initiation threshold coefficient; whereas the false positive prediction rate is lower with increasing initiation threshold coefficient. Moreover, the prompt detection of initiation requires a low initiation threshold coefficient and a small moving window size. To achieve high successful prediction rate of erosion and sharp detection of the initiation, initiation threshold coefficients of 3 and 4 and moving window sizes of 3 and 6 are recommended.

Example 4

Ablation of Kidney Tissue

Figure 16:
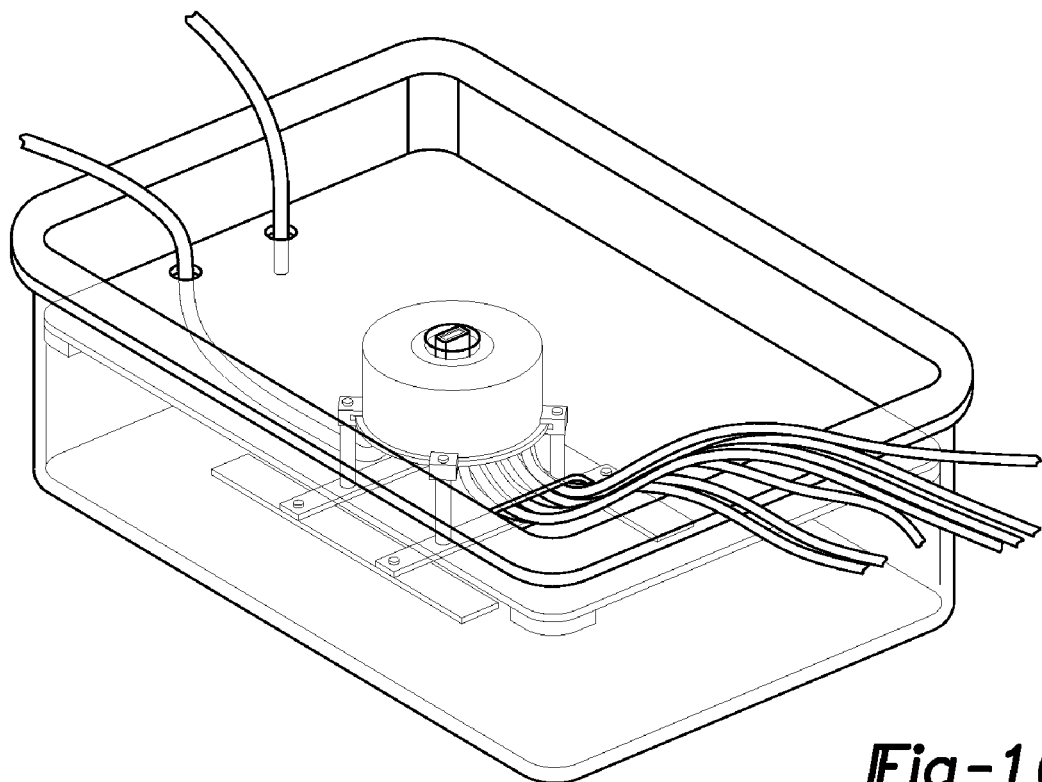
FIG. 16 is a photograph of a therapeutic ultrasound unit constructed in accordance with the teachings of the present disclosure.

Ultrasound Apparatus The therapeutic ultrasound unit, shown in FIG. 16, consisted of a large, high power annular 18 element piezo-composite phased transducer array (750 kHz, 145 mm diameter, 100 mm focal length) [Imasonic, Besançon, FR]. A commercial diagnostic 2.5 MHz imaging probe (General Electric Medical Systems, Milwaukee, Wis.) was coaxially aligned through the central hole of the phased-array and operated in a 1.8 MHz octave mode (harmonic imaging) with a nominally 30 Hz frame rate. The imaging probe was offset from the back of the therapeutic transducer by 40 mm resulting in an imaging distance of 60 mm. This provided sufficient image quality without substantially blocking the path of the therapeutic transducer. The transducer system was mounted on a brass frame tilted 20 degrees from vertical (to reduce reverberations from the animal skin surface) and placed at the bottom of a tank filled with degassed water. The focal pressure field could not be successfully measured at the high power output used in these experiments due to the spontaneous failure of the water. Extrapolation of the peak negative pressure in the focal zone from membrane and fiber-optic hydrophone measurements at lower power yielded a value of 25 megapascals.

Figure 17:
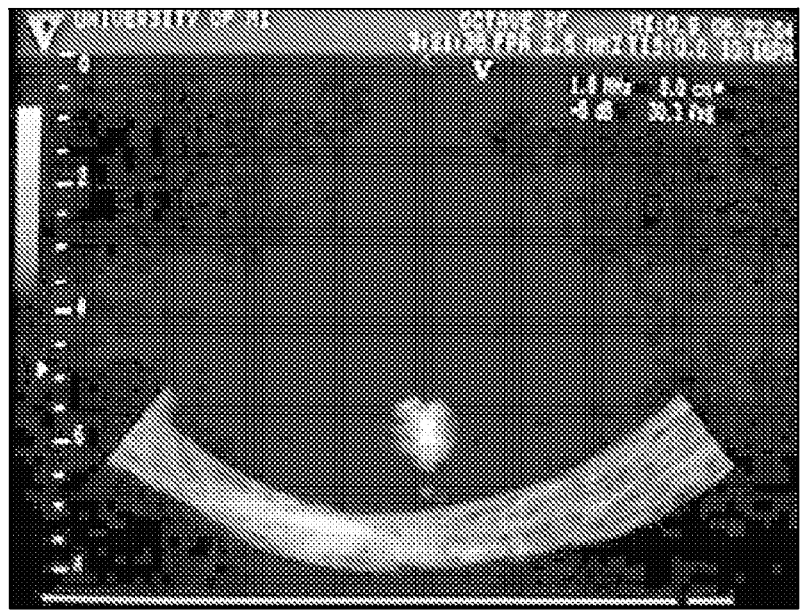
FIG. 17 is an ultrasound image of a hyper-echoic zone as a result of a bubble cloud generated by therapeutic ultrasound.

Localization of the focal zone was accomplished by delivering a single 15 cycle pulse from the therapeutic transducer at 1 Hz pulse repetition frequency. Each pulse created a brief hyper-echoic zone on the ultrasound image of the empty water tank and was used to mark the expected therapeutic transducer focal location on the B-scan ultrasound image, as shown in FIG. 17.

Rabbit Preparation: New Zealand white rabbits, weighing 3-4 kg were pre-medicated and anesthetized with intramuscular injections of 35 mg/kg ketamine and 5 mg/kg xylocalne. The abdomen was shaved and a depilatory cream was applied. Following endotrachial intubation, anesthetic effect was maintained with forced ventilation of 1-2% Isoflurane. Vital signs (heart rate, SpO2, respiratory rate, and temperature) were monitored with a veterinary monitoring system (Heska Corp., Fort Collins, Colo.).

Figure 18:
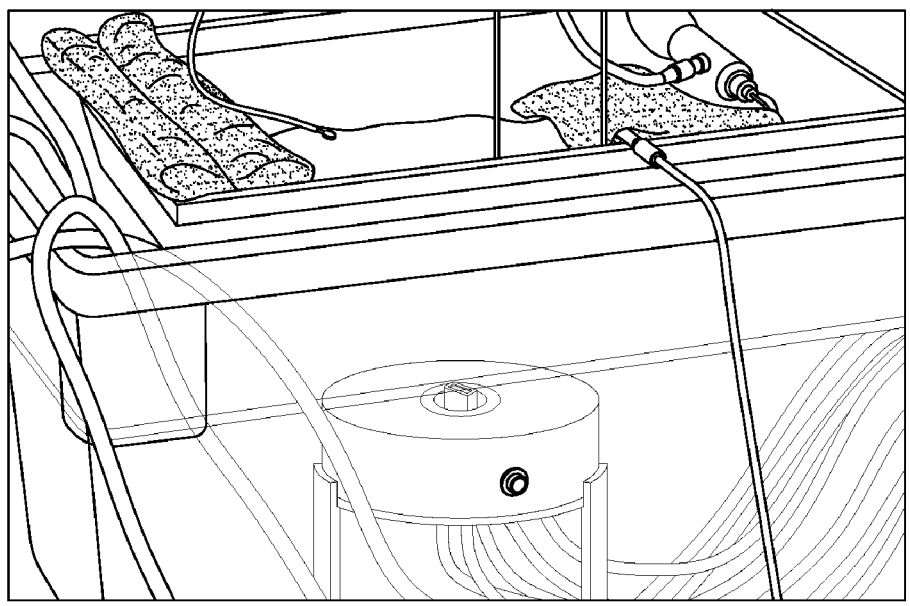
FIG. 18 is a photograph of a positioning frame and three-axis positioning system for a therapeutic ultrasound unit constructed in accordance with the teachings of the present disclosure.

Rabbit Positioning: Each rabbit was first placed on its left side on a thin plastic membrane attached to an aluminum and plastic carrier frame. The carrier was suspended on a three axis positioning system (Parker-Hannifin Corp., Daedal Division, Irwin, Pa.). A small amount of degassed water was applied between the skin and plastic membrane to ensure good coupling. A 10 MHz linear ultrasound probe (General Electric Medical Systems, Milwaukee, Wis.) was hand scanned on the plastic membrane to locate the kidney and the approximate position marked with a felt tip pen. The carrier was then partially submerged in the tank of degassed, deionized water, as shown in FIG. 18. The kidney was re-located with the imaging probe coaxially positioned within the therapy unit and positional adjustments were made with the carrier positioning system to target renal parenchyma.

Ultrasound Treatment: Energy was delivered in the form of short pulses consisting of 15 cycles of high energy ultrasound waves. A representative graph of 11 cycles is shown in FIG. 19. Sequences of 10, 100, 1000, and 10000 pulses were applied at a pulse repetition frequency of 100 Hz to the lower and upper poles of the left kidney and the lower pole of the right kidney. These pulse sequences corresponded to total treatment times of 0.1, 1, 10, and 200 seconds respectively. For treatments of 10 seconds and less, the ventilator was paused (breath hold) to ensure that all pulses were delivered in the absence of respiratory motion. To deliver 10000 pulses, energy was delivered in bursts of 500 pulses (5 seconds) during the end expiratory phase of the respiratory cycle. This was followed by a 5 second pause as a breath was delivered via the ventilator. In this fashion, delivery of 10000 pulses required a total time of 200 seconds.

Euthanasia and Specimen Preparation: Immediately after completion of the experiments, each rabbit was euthanized with intravenous administration of 100 mg/kg Pentobarbitol. Death was confirmed by loss of heart rate on the monitor and decrease in oxygen saturation. Bilateral pneumothoraces were created. All procedures described were approved by the University of Michigan Committee on Use and Care of Animals prior to this study.

Kidneys were harvested through an open flank incision. The perinephric tissues as well as tissue in the path of the ultrasound energy were inspected closely for signs of hemorrhage and injury. The renal vein, artery and ureter were transected and the entire kidney removed. For initial experiments, the specimen was finely sliced to identify the created lesions and allow immediate gross examination. With later experiments, the entire kidney was placed in formalin for fixation and then processed for hematoxylin and eosin staining.

Results: Pulsed cavitational ultrasound energy was successfully delivered to the targeted zone of the kidneys in 10 rabbits resulting in an immediate hyperechoic region 174 on real-time ultrasound imaging, as shown in FIG. 20. This hyperechoic region was confined to the expected location of the ultrasound focus and was highly transient in nature. The appearance on diagnostic ultrasound images likely represents acoustic reflection from gas bubbles generated within the focal zone by cavitational mechanisms.

Delivery of only 10 pulses produced scattered focal hemorrhagic zones within a 3×10 mm ellipsoid region corresponding to the focal zone. Histological analysis confirmed multiple hemorrhagic zones containing some cellular debris. Immediately surrounding the hemorrhage a zone of architecturally intact, though mortally injured cells with absent or pyknotic nuclei were noted. This zone spanned a distance of approximately 100 microns. Beyond this zone a ring of less severe cellular damage was present also spanning approximately 100 microns, as shown in FIG. 21. When 100 pulses were delivered a greater number of hemorrhagic areas of larger size were noted within the same sized ellipsoid region. Surrounding each area of hemorrhage, the same two tiered pattern of cellular injury was noted, with each ring again spanning only 100 microns.

Gross examination of the target volume after 1000 to 10000 pulses revealed an elliptical cavity also measured to be 3×10 mm with smooth boundaries and a liquefied core. Histological analysis was notable for large confluent areas of hemorrhage and acellular material thought to represent cytoplasm and homogenized cellular material. The few islands of recognizable parenchymal structure within the large confluent areas contained only mortally damaged cells. The same pattern of damage ringing these large acellular regions was evident as seen in the treatments with 10 or 100 pulses. With 10000 pulses, the boundary of the confluent acellular region appears to be more uniform with a narrower zone of peripheral damage, as shown in FIG. 21.

Gross examination of the perinephric tissues, muscle, and skin in the path of the ultrasound beam revealed no evidence of significant collateral injury. Following two treatments with 10000 pulses, the skin overlying the targeted volume exhibited several very small petechia that had resolved when examined 30 minutes later.

This embodiment demonstrates that mechanical (cavitational based) subdivision/destruction of tissue can be accomplished by delivery of short, high intensity ultrasound pulses without thermal effects. Furthermore, transcutaneous delivery of energy can be used to ablate regions of normal rabbit kidney without collateral damage and skin injury.

Mechanical (cavitational) destruction of tissue without thermal effects can be accomplished by delivery of short, high intensity ultrasound pulses. As demonstrated in these experiments, transcutaneous delivery of energy to ablate regions of normal rabbit kidney is possible without collateral damage and skin injury. The present teachings provide unique non-invasive, non-thermal ablative therapy for treatment of small renal masses.

Example 5

Imaging Feedback in Histotripsy of Liver Tissue

High intensity pulsed ultrasound was used to disrupt liver tissue through cavitation while monitoring with 8 MHz ultrasound imaging. The apparatus 176 is shown in FIG. 22. Freshly harvested liver samples 178 (less than 6 hours) were placed in degassed saline and then vacuum sealed in thin plastic bags. The samples 178 were placed in the nominal focus of a 1 MHz 512 channel therapeutic array transducer 180 (Imasonic, Besançon, France). An 8 MHz linear imaging transducer 182 (Siemens Elegra) was placed opposite to the therapeutic transducer 180 close to the liver sample 178 in order to monitor ultrasound treatments. The transducers 180, 182 are coupled to a computer control and data collection device 184 (coupling of therapeutic transducer 180 not shown).

Ultrasound treatment consisted of scanning the therapeutic transducer focus electronically over 42 locations to define a one centimeter square grid 186, as shown in FIG. 23, perpendicular to the imaging axis. In each location, one high intensity (>18 MPa peak negative pressure) 25 cycle burst was delivered before moving to the next location. The wait time between locations was 25 milliseconds and the entire set was repeated 2000 times. This yielded an effective duty cycle of 0.1% and a long treatment time of 28 minutes. The intention in using such a low duty cycle was to isolate non-thermal effects of cavitation. Previous experiments with an embedded thermocouple had determined that this protocol yielded a temperature rise of 3 degrees or less. The low duty cycle also allowed unsynchronized real-time B-scan imaging with only a few scan lines showing interference for each frame through out the treatment.

During treatment, the targeted region appeared as an area of highly transient hyperechogenicity on B-scan ultrasound images (differing from the quasi-static hyperechogenicity typically observed during high intensity thermal therapy). At the end of treatment, this hyperechogenicity rapidly faded leaving a substantial decrease in speckle amplitude. B-scan RF image data was stored from before and after treatment. Histogram distributions of dB scaled speckle amplitude were generated for this area and the corresponding area before treatment. The median, 10th, and 90th percentile speckle amplitudes were recorded for each distribution, as shown in FIG. 24. Amplitude distributions are plotted before treatment 188 and after treatment 190.

Liver samples were fixed in formalin and sliced for evaluation. Slides were prepared from selected samples.

Pulsed ultrasound at high intensities and low duty cycle is effective at creating precise regions consisting of liquefied tissue. These areas appear as highly transient hyperechoic spots during treatment and then fade rapidly leaving substantially reduced imaging speckle amplitude. This is thought to be caused by mechanical homogenization through cavitation on a very fine scale resulting in a loss of effective ultrasound scatters at 8 MHz. Significant changes in speckle amplitude are easily detected with standard diagnostic ultrasound imaging and can be used for non-invasive feedback on treatment efficacy in ultrasound surgery using cavitation. Application of 2000 pulses (sufficient to liquefy the target tissue) resulted in an average 22.4 dB reduction in speckle amplitude. These experiments demonstrate effective feedback monitoring during ultrasound surgery using cavitation.

Example 6

Feedback and Monitoring Using Ultrasound Imaging of Backscatter Reduction

Methods: Freshly harvested (less than 6 hours post-mortem) porcine liver obtained from a local slaughter house was sectioned into samples approximately 10×5×3 cm and placed in degassed saline for 30 minutes in a vacuum chamber to purge surface bubbles. After being vacuum sealed in thin plastic bags (FoodSaver VAC300, Tilia International Inc, San Francisco, Calif.), the samples 192 were then placed in the geometric focus of a 1 MHz, 513 channel therapeutic array transducer 194 (Imasonic, Besançon, FR), as shown in FIG. 25. The therapeutic transducer 194 had a diameter and geometric focal distance of 15 cm. An 8 MHz linear imaging transducer 196 (Siemens Elegra) was placed opposite the therapeutic transducer 194 very close to the liver sample 192 in order to monitor ultrasound treatments.

Ultrasound treatment consisted of scanning the therapeutic transducer 194 focus electronically over 42 locations to define a one centimeter square grid, as shown in FIG. 26, perpendicular to the imaging axis. In each location, one high amplitude (25 MPa peak negative pressure) 25 cycle burst was delivered before moving to the next location. The delay time between ultrasound exposures at each location was 25 milliseconds and the entire set was repeated 2000 times. This yielded an effective duty cycle of 0.1% and a total treatment time of 28 minutes. The intention in using such a low duty cycle was to isolate non-thermal effects of cavitation. Experiments with an embedded thermocouple had determined that this protocol yielded a temperature rise of 3 degrees or less within the treatment volume. The low duty cycle also allowed unsynchronized real-time B-scan imaging for monitoring with only a few scan lines in each imaging frame corrupted by interference throughout the treatment.

FIG. 26 shows the planned treatment grid (left) and sample cross-section (right) after treatment. The treatment grid covers approximately one square centimeter. Tissue was fixed in formalin prior to slicing. Note the disruption of functional unit structure within the grid area, sharp margins, and close match to the planned treatment grid.

FIG. 27 shows a representative pressure waveform from the therapeutic transducer at the focus measured with a fiber optic probe hydrophone system. The first four cycles of a highly shocked five cycle pressure waveform at high amplitude from the therapeutic transducer measured with a fiber optic hydrophone are shown. Operation at this intensity resulted in rapid failure of the fiber optic probe tip (after about 25 bursts). All measurements were made in degassed 20° C. water. Peak positive pressures are extremely high due to non-linear propagation and are likely limited by the photo-detector bandwidth of 50 MHz. Negative pressure measurements do not require high detector bandwidths for accuracy and have been shown to be related to cavitation activity. For this reason, the peak negative pressures are reported here. At the low duty cycle used in these experiments, very large peak negative pressures were required to generate spontaneous inertial cavitation adequate for the desired therapeutic effect. At pressure levels in excess of about 15 MPa peak negative, single ultrasound pulses of 25 cycle length caused cavitation at the tip of the glass fiber. Measurements could not be made because the glass-vapor interface caused a substantial temporary increase in the reflection signal saturating the photo detector. Additionally, the brittle glass fiber would fracture after several cavitation events requiring re-cleaving before continuing calibration. At lower drive levels, the peak negative pressure was observed to be achieved by the fourth cycle of a pulse with additional cycles yielding the same value. Measurements were possible for pulse lengths of five cycles or less at higher pressures than for 25 cycles. Therefore, a five cycle pulse was used at higher pressure levels assuming the peak negative pressure would be the same as for a 25 cycle pulse. Using a five cycle pulse, the measured peak negative pressure was 25 MPa for the voltage setting used for ultrasound treatments on liver tissue. Peak positive pressures of 190 MPa were measured despite the 50 MHz bandwidth of the photo-detector as mentioned.

Ultrasound B-scan RF image frames (256 scan lines, 36 MHz sampling rate) were stored from before and after treatment. The scanner was set for its maximum dynamic range of 70 dB and gain adjusted for a moderately bright image without saturation at the start of each experiment and then not changed. The scanner operated asynchronously from the therapeutic system at a frame rate of 14 Hz throughout the experiments. The treatment region was co-registered with the B-scan from observing with the aligned imaging transducer the cavitation cloud generated by exciting the therapeutic transducer in water before the tissue sample was introduced. By imaging perpendicular to the treatment grid, the extent of the treated volume was ensured to be greater than the imaging plane thickness for maximum contrast between the treatment volume and surrounding tissue. Additionally, the imaging distance from the treatment volume was only 10-20 mm to minimize absorption and aberration for the highest quality ultrasound images. Histogram distributions of dB scaled backscatter amplitude were generated for the treatment region from before and after treatment. These distributions were expected to be "Rayleigh-like" (subject to limitations of sampling discretization and the dynamic range of the system), however, to avoid prejudicing toward a particular distribution, the median, 10th, and 90th percentile were recorded to characterize simply the distributions and test the hypothesis of a shift toward lower backscatter after treatment, as shown in FIG. 28.

FIG. 28 shows the comparison of sample B-scan images before and after treatment and corresponding histograms for the treatment area ROI indicated by the square 198. B-scan images are displayed on a 60 dB dynamic range scale. The significant echogenicity change is caused by a shift in the backscatter amplitude distribution. Note that the B-scan images are perpendicular to the treatment grid and slice planes in FIGS. 26 and 30.

After treatment, liver samples were fixed whole in 10% formalin and later sliced for evaluation. Whole mount histological slides were prepared from selected samples (H&E stain, 5 µm thickness, 1 mm intervals) for closer inspection.

Results: Because of the very low duty cycle, it was possible to observe in real time effects during treatment with only a few ultrasound B-scan lines corrupted by interference. The targeted region appeared as an area of highly transient hyperechogenicity. This refers to a spot of variable brightness changing in appearance ("twinkling") much faster than once a second. This is in contrast to the quasi-static hyperechogenicity typically observed during high intensity thermal therapy (thought to be due to boiling or out-gassing) where appearances change slowly over several seconds to minutes. At the end of treatment, the hyperechogenicity rapidly faded leaving a substantial decrease in image amplitude.

On B-scan ultrasound images from before and after treatment, the treatment region (ROI) appeared as a significantly hypoechoic area compared to before treatment or to surrounding areas (FIG. 28). The image amplitude distribution in the ROI shifted −22.4, 2.3 dB (mean shift in the median of each distribution from before to after treatment). The mean width of the distributions ($10^{th}$ to $90^{th}$ percentile range) did not change significantly from before: 18.3, 1.3 dB to after: 19.5, 2.3 dB treatment. Distributions from before and after treatment were highly separable with no overlap from the $10^{th}$ to $90^{th}$ percentiles for each experiment, as shown in FIG. 29. Comparable size regions 10 mm away from the ROI (to the side) did not change significantly (0.1, 1.1 dB shift in median).

FIG. 29 shows the spread of distributions for each of eight experiments. Lines represent the range from 10% to 90% for a distribution. Circles/dots represent the medians. For all eight experiments, the 10% to 90% ranges do not overlap for before and after treatment and distribution medians shift by about 20 dB.

On gross examination after slicing, the treatment region appeared as a square of disrupted tissue structure with sharp borders (FIGS. 26 and 30). Representative histological slides showed complete loss of recognizable tissue structure within the treatment volume at low and high magnification. Tissue areas adjacent to the treatment area appeared intact. The border of the treatment area showed a transition zone with islands of disruption. The transition zone from all cells intact to all cells disrupted was about 1 mm wide.

The observed changes suggest a highly localized reduction in backscatter for the treatment volume. Backscatter speckle in ultrasound images is produced by interference in the backscatter waves reflecting off of numerous acoustic discontinuities. In tissue, these discontinuities arise from the particular microstructure arrangement of tissue components with varying acoustic impedances. For the imaging frequency used here (8 MHz), the acoustic wavelength is about 200 µm. The sources of backscatter include hepatocytes, extracellular matrix (note the fibrous bands surrounding functional units in FIG. 30) which are more prominent in porcine than healthy human liver), and networks of small arterioles and capillaries. Cavitational collapse of bubbles is known to be able to generate highly localized extreme temperatures and reactive molecules. The relative contributions of these effects as well as direct mechanical forces (micro-streaming, jetting, radiation force) and the release of chemically active molecules from subcellular compartments to the overall mechanical disruption of tissue is not known. An extensive discussion of these mechanisms interacting with cells in vitro is found in M. W. Miller, D. L. Miller, A. A. Brayman, "A review of in vitro bioeffects of inertial ultrasonic cavitation from a mechanistic perspective", Ultrasound in Medicine and Biology, vol. 22, pp. 1131-1154. One possible explanation for the observed backscatter decrease is that the breakdown and mixing of tissue structure caused by mechanical disruption through cavitation yields a more homogeneous distribution of acoustic discontinuities with reduced backscattering cross-sectional area.

FIG. 30 shows photomicrographs of selected histology samples (H & E stain) from a lesion created through histotripsy. Low magnification image A shows a square region of disruption. Magnified image B of the location marked on image A shows the border of the lesion with a transition zone of partial disruption about 1 mm in width. Further magnification in images C and D, where marked, show normal appearing hepatocytes in the area outside the disrupted region (C) and a complete loss of cellular structure within the disrupted zone (D).

The histotripsy process produces very finely subdivided tissue with the bulk of fragments apparently less than 1 um. These structural changes are convenient for ultrasound therapy feedback because they are physical changes that can be directly imaged and are likely to be correlated with clinical outcomes. Using real time ultrasound imaging, the therapeutic process can be monitored until complete disruption has been achieved. Although the appearance of this structural change is unknown for other imaging modalities, it is persistent (unlike temperature elevation, for example) so that post treatment imaging could be applied in a standard clinical setting rather than in the operating room. This would permit more extensive evaluation of treatment effectiveness with multiple imaging modalities capable of detecting the structural changes.

High intensity ultrasound can be used to mechanically break down tissue to a very fine degree through cavitation. Disrupted tissue can be easily detected with standard B-scan ultrasound imaging as a substantial reduction in backscatter amplitude appearing as a hypoechoic zone. Backscatter reduction should be useful as direct feedback for ultrasound therapy using cavitation.

The examples and other embodiments described herein are exemplary and not intended to be limiting in describing the full scope of compositions and methods of this technology. Equivalent changes, modifications and variations of specific embodiments, materials, compositions and methods may be made within the scope of the present technology, with substantially similar results.

What is claimed is:

1. A method for controlled mechanical sub-division of soft tissue comprising:
   de-initiating a non-treatment portion of the soft tissue to increase a cavitation threshold from a first threshold to a second threshold in said non-treatment portion of the soft tissue, wherein said de-initiating said non-treatment portion of the soft tissue comprises de-initiating said non-treatment portion of the soft tissue using a deleting pulse sequence at a pulse intensity less than said first threshold;
   using a transducer outputting an initiation pulse sequence at a treatment portion of the soft tissue, wherein said de-initiating a non-treatment portion of the soft tissue and said outputting an initiation pulse sequence are performed simultaneously;
   detecting initiation of a bubble cloud in said treatment portion of the soft tissue in response to said initiation pulse sequence;
   outputting a bubble cloud maintenance and sustaining pulse sequence at said treatment portion; and
   outputting a therapy pulse sequence which generates and interacts with said bubble cloud to at least partially fractionate the soft tissue in said treatment portion.

2. The method according to claim 1, further comprising: detecting cessation of said bubble cloud.

3. The method according to claim 2, further comprising: re-outputting said initiation pulse sequence in response to said cessation of said bubble cloud.

4. The method according to claim 2, further comprising: re-outputting said bubble cloud sustaining pulse sequence prior to said cessation of said bubble cloud.

5. The method according to claim 1 wherein said outputting an initiation pulse sequence comprises outputting an initiation pulse sequence at a frequency equal to a frequency of at least one of said bubble cloud sustaining pulse sequence and said therapy pulse sequence.

6. The method according to claim 1 wherein said outputting an initiation pulse sequence comprises outputting an initiation pulse sequence operable to create at least one of a vapor cloud or a plasma cloud.

7. The method according to claim 1 wherein said outputting an initiation pulse sequence comprises outputting an initiation pulse sequence causing an ionizing radiation bubble chamber effect.

8. The method according to claim 1 wherein said outputting an initiation pulse sequence comprises mechanically injecting cavitation nuclei.

9. The method according to claim 8 wherein said mechanically injecting cavitation nuclei comprises mechanically injecting cavitation nuclei intravascularly.

10. The method according to claim 8 wherein said mechanically injecting cavitation nuclei comprises mechanically injecting cavitation nuclei into a therapy volume.

11. The method according to claim 1, further comprising:
    targeting a therapeutic substance at a predetermined location in the soft tissue to enhance enucleation of dissolved gases in the soft tissue.

12. The method according to claim 11 wherein said targeting a therapeutic substance comprises targeting a therapeutic substance selected from the group consisting essentially of enzymes, proteins, and proto-bubble droplets.

13. The method according to claim 1 wherein said outputting an initiation pulse sequence comprises mechanically stimulating the soft tissue to generate cavitation nuclei.

14. The method according to claim 1 wherein said outputting an initiation pulse sequence comprises thermally stimulating the soft tissue to generate vapor nuclei.

15. The method according to claim 1, further comprising:
    interleaving said bubble cloud sustaining pulse sequence and said therapy pulse sequence.

16. The method according to claim 1 wherein said outputting a bubble cloud sustaining pulse sequence comprises optically stimulating said bubble cloud to generally maintain said bubble cloud.

17. The method according to claim 1 wherein said outputting a bubble cloud sustaining pulse sequence comprises stimulating said bubble cloud via ionizing radiation to generally maintain said bubble cloud.

18. The method according to claim 1 wherein said outputting a bubble cloud sustaining pulse sequence comprises mechanically stimulating said bubble cloud to generally maintain said bubble cloud.

19. The method according to claim 1 wherein said outputting a bubble cloud sustaining pulse sequence comprises thermally stimulating said bubble cloud to generally maintain said bubble cloud.

* * * * *